(12) United States Patent
Bolling et al.

(10) Patent No.: US 10,713,925 B2
(45) Date of Patent: *Jul. 14, 2020

(54) HAND CLEANLINESS

(71) Applicant: BioVigil Hygiene Technologies, LLC, Ann Arbor, MI (US)

(72) Inventors: Steven F. Bolling, Ann Arbor, MI (US); Brian Sheahan, Santa Rosa, CA (US); Joseph M. Madden, Los Gatos, CA (US); Shimon Gersten, San Diego, CA (US)

(73) Assignee: BioVigil Hygiene Technologies, LLC, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/959,653

(22) Filed: Aug. 5, 2013

(65) Prior Publication Data
US 2014/0049391 A1    Feb. 20, 2014

Related U.S. Application Data

(63) Continuation of application No. 12/877,596, filed on Sep. 8, 2010, now Pat. No. 8,502,681, which is a
(Continued)

(51) Int. Cl.
*G08B 21/02* (2006.01)
*G08B 21/24* (2006.01)
*G16H 40/20* (2018.01)

(52) U.S. Cl.
CPC .......... *G08B 21/245* (2013.01); *G16H 40/20* (2018.01)

(58) Field of Classification Search
CPC ....... A61B 5/6806; A61B 8/13; A61B 8/4209; A61B 8/4227; A61B 8/4455; A63G 21/18;
(Continued)

(56) References Cited

U.S. PATENT DOCUMENTS

| 4,354,292 A | 10/1982 | Telestad et al. |
| 4,370,983 A | 2/1983 | Lichtenstein |

(Continued)

FOREIGN PATENT DOCUMENTS

| EP | 0 429 414 | 5/1991 |
| EP | 1 455 177 | 9/2004 |

(Continued)

OTHER PUBLICATIONS

Berry et al., "The Business Case for Better Buildings," *Front Health Service Management*, 1-29 (2004).
(Continued)

*Primary Examiner* — Daniel Previl
(74) *Attorney, Agent, or Firm* — Fish & Richardson P.C.

(57) ABSTRACT

Among other things, systems to encourage compliance with hand washing procedures can include: an infrared emitter that projects a first infrared beam with a transverse cross-section having a first axis and a second axis that is shorter than the first axis, the transverse cross-section having a maximum length along the first axis, the infrared emitter modulating the first infrared beam to transmit a first identification signal; wherein the infrared emitter projecting the first infrared beam is placed such that the first axis of the transverse cross-section of the first infrared beam is substantially parallel to a boundary.

10 Claims, 61 Drawing Sheets

Related U.S. Application Data continuation-in-part of application No. 11/415,687, filed on May 1, 2006, now Pat. No. 7,936,275, which is a continuation-in-part of application No. 11/353,746, filed on Feb. 14, 2006, now Pat. No. 7,616,122, which is a continuation-in-part of application No. 11/157,094, filed on Jun. 20, 2005, now Pat. No. 7,286,057.

(60) Provisional application No. 61/240,622, filed on Sep. 8, 2009.

(58) Field of Classification Search
CPC ...... A63G 27/00; A63G 31/007; A63G 31/16; A63G 3/02; B65G 43/00; G01S 5/0072; G01S 13/878; G01S 15/8936; G01S 19/14
USPC ....... 340/539.13, 573.1, 573.4, 573.5, 539.1, 340/691.1, 568.1, 572.1–572.9, 309.7, 340/693.1
See application file for complete search history.

(56) References Cited

U.S. PATENT DOCUMENTS

| | | |
|---|---|---|
| 4,606,085 A | 8/1986 | Davies |
| 4,706,493 A | 11/1987 | Chang et al. |
| 4,782,334 A | 11/1988 | Meaney |
| 5,202,666 A | 4/1993 | Knippscheer |
| 5,366,896 A | 11/1994 | Margrey et al. |
| 5,373,852 A | 12/1994 | Harrison et al. |
| 5,412,816 A | 5/1995 | Paterson et al. |
| 5,428,213 A | 6/1995 | Kurihara |
| 5,441,047 A | 8/1995 | David et al. |
| 5,544,649 A | 8/1996 | David et al. |
| 5,606,159 A | 2/1997 | Kurihara |
| 5,610,589 A | 3/1997 | Evans et al. |
| 5,670,945 A | 9/1997 | Applonie |
| 5,685,262 A | 11/1997 | Stevenson |
| 5,771,925 A | 6/1998 | Lewandowski |
| 5,793,653 A | 8/1998 | Segal |
| 5,808,553 A | 9/1998 | Cunningham |
| 5,812,059 A | 9/1998 | Shaw et al. |
| 5,870,015 A | 2/1999 | Hinkel |
| 5,900,067 A | 5/1999 | Jones |
| 5,900,801 A | 5/1999 | Heagle et al. |
| 5,914,247 A | 6/1999 | Casey et al. |
| 5,939,974 A | 8/1999 | Heagle et al. |
| 5,943,713 A | 8/1999 | Paterson et al. |
| 5,945,910 A | 8/1999 | Gorra |
| 5,952,924 A | 9/1999 | Evans et al. |
| 5,954,069 A | 9/1999 | Foster |
| 5,966,753 A | 10/1999 | Gauthier et al. |
| 5,992,430 A | 11/1999 | Chardack et al. |
| 6,001,127 A | 12/1999 | Schoon et al. |
| 6,009,333 A | 12/1999 | Chaco |
| 6,029,293 A | 2/2000 | Patterson et al. |
| 6,029,600 A | 2/2000 | Davis |
| 6,032,071 A | 2/2000 | Binder |
| 6,038,331 A | 3/2000 | Johnson |
| 6,125,482 A | 10/2000 | Foster |
| 6,131,587 A | 10/2000 | Chardack et al. |
| 6,190,326 B1 | 2/2001 | McKinnon et al. |
| 6,236,317 B1 | 5/2001 | Cohen et al. |
| 6,236,953 B1 | 5/2001 | Segal |
| 6,245,206 B1 | 6/2001 | Anderson et al. |
| 6,246,330 B1 | 6/2001 | Nielsen |
| 6,278,372 B1 | 8/2001 | Velasco et al. |
| 6,347,724 B1 | 2/2002 | Chen et al. |
| 6,355,030 B1 | 3/2002 | Aldrich et al. |
| 6,375,038 B1 | 4/2002 | Daansen et al. |
| 6,392,546 B1 | 5/2002 | Smith |
| 6,404,837 B1 | 6/2002 | Thompson et al. |
| 6,417,773 B1 | 7/2002 | Vlahos et al. |
| 6,426,225 B1 | 7/2002 | Lewis et al. |
| 6,426,701 B1 | 7/2002 | Levy et al. |
| 6,431,400 B1 | 8/2002 | O'Maley et al. |
| 6,468,800 B1 | 10/2002 | Stylli et al. |
| 6,471,087 B1 | 10/2002 | Shusterman |
| 6,542,568 B1 | 4/2003 | Howes, Jr. et al. |
| 6,547,130 B1 | 4/2003 | Shen |
| 6,572,564 B2 | 6/2003 | Ito et al. |
| 6,592,822 B1 | 7/2003 | Chandler |
| 6,605,038 B1 | 8/2003 | Teller et al. |
| 6,633,772 B2 | 10/2003 | Ford et al. |
| 6,687,190 B2 | 2/2004 | Momich et al. |
| 6,702,826 B2 | 3/2004 | Liddicoat et al. |
| 6,727,818 B1 | 4/2004 | Wildman et al. |
| 6,748,281 B2 | 6/2004 | Alsio |
| 6,757,898 B1 | 6/2004 | Ilsen et al. |
| 6,776,791 B1 | 8/2004 | Stallings et al. |
| 6,790,231 B2 | 9/2004 | Liddicoat et al. |
| 6,814,816 B2 | 11/2004 | Achar et al. |
| 6,847,913 B2 | 1/2005 | Wigley et al. |
| 6,867,698 B2 | 3/2005 | Herbert et al. |
| 6,882,273 B2 | 4/2005 | Kano |
| 6,882,278 B2 | 4/2005 | Winings et al. |
| 6,883,563 B2 | 4/2005 | Smith |
| 6,895,338 B2 | 5/2005 | Hsuing et al. |
| 6,913,608 B2 | 7/2005 | Liddicoat et al. |
| 6,929,607 B2 | 8/2005 | Lipman |
| 6,942,694 B2 | 9/2005 | Liddicoat et al. |
| 6,943,678 B2 | 9/2005 | Muirhead |
| 6,964,638 B2 | 11/2005 | Theodoracopulos et al. |
| 6,965,312 B2 | 11/2005 | Lerg |
| 6,967,576 B2 | 11/2005 | Hayes et al. |
| 6,975,231 B2 | 12/2005 | Lane et al. |
| 7,007,698 B2 | 3/2006 | Thornton |
| 7,015,816 B2 | 3/2006 | Wildman et al. |
| 7,020,508 B2 | 3/2006 | Stivoric et al. |
| 7,024,236 B2 | 4/2006 | Ford et al. |
| 7,034,677 B2 | 4/2006 | Steinthal et al. |
| 7,034,691 B1 | 4/2006 | Rapaport et al. |
| 7,045,673 B1 | 5/2006 | Batich et al. |
| 7,063,722 B2 | 6/2006 | Marquez |
| 7,069,444 B2 | 6/2006 | Lowensohn et al. |
| 7,074,183 B2 | 7/2006 | Castellanos |
| 7,081,131 B2 | 7/2006 | Thornton |
| 7,087,015 B1 | 8/2006 | Comrie et al. |
| 7,095,501 B2 | 8/2006 | Lambert et al. |
| 7,098,793 B2 | 8/2006 | Chung |
| 7,107,631 B2 | 9/2006 | Lang et al. |
| 7,122,005 B2 | 10/2006 | Shusterman |
| 7,132,940 B2 | 11/2006 | Ehben et al. |
| 7,191,097 B1 | 3/2007 | Lee et al. |
| 7,228,874 B2 | 6/2007 | Bolderheij et al. |
| 7,236,097 B1 | 6/2007 | Cunningham |
| 7,242,306 B2 | 7/2007 | Wildman et al. |
| 7,242,307 B1 | 7/2007 | LeBlond et al. |
| 7,267,798 B2 | 9/2007 | Chandler |
| 7,271,728 B2 | 9/2007 | Taylor et al. |
| 7,286,057 B2 | 10/2007 | Bolling |
| 7,293,645 B2 | 11/2007 | Harper et al. |
| 7,482,936 B2 | 1/2009 | Bolling |
| 7,616,122 B2 | 11/2009 | Bolling |
| 7,755,494 B2 | 7/2010 | Melker et al. |
| 7,936,275 B2 | 5/2011 | Bolling |
| 7,978,083 B2 | 7/2011 | Melker et al. |
| 7,982,619 B2 | 7/2011 | Bolling |
| 8,279,063 B2 | 10/2012 | Wohltjen |
| 8,502,681 B2 * | 8/2013 | Bolling .................. G16H 40/20 340/573.1 |
| 8,525,666 B2 | 9/2013 | Melker et al. |
| 9,478,118 B2 | 10/2016 | Keown et al. |
| 2002/0000449 A1 | 1/2002 | Armstrong |
| 2002/0019586 A1 | 2/2002 | Teller et al. |
| 2002/0082177 A1 | 6/2002 | Tabaac |
| 2002/0095073 A1 | 7/2002 | Jacobs et al. |
| 2002/0132214 A1 | 9/2002 | Mattson et al. |
| 2002/0135486 A1 | 9/2002 | Brohagen et al. |
| 2002/0180605 A1 | 12/2002 | Ozguz et al. |
| 2003/0019536 A1 | 1/2003 | Smith |
| 2003/0026549 A1 | 2/2003 | Ellis et al. |

(56) References Cited

U.S. PATENT DOCUMENTS

| | | | |
|---|---|---|---|
| 2003/0030562 A1* | 2/2003 | Lane | G16H 40/20 340/573.4 |
| 2003/0130567 A1 | 7/2003 | Mault et al. | |
| 2003/0147925 A1 | 8/2003 | Sawan et al. | |
| 2003/0164456 A1 | 9/2003 | Petrich et al. | |
| 2003/0179224 A1 | 9/2003 | Alsio | |
| 2003/0220215 A1 | 11/2003 | Manske | |
| 2004/0034289 A1 | 2/2004 | Teller et al. | |
| 2004/0041788 A1* | 3/2004 | Ternullo | G06F 3/011 345/158 |
| 2004/0067544 A1 | 4/2004 | Vogel et al. | |
| 2004/0090333 A1* | 5/2004 | Wildman | G06F 19/3418 340/573.1 |
| 2004/0092965 A1 | 5/2004 | Parihar | |
| 2004/0148019 A1 | 7/2004 | Vidlund et al. | |
| 2004/0148020 A1 | 7/2004 | Vidlund et al. | |
| 2004/0150527 A1 | 8/2004 | Harper et al. | |
| 2004/0155772 A1 | 8/2004 | Medema et al. | |
| 2004/0172063 A1 | 9/2004 | Li et al. | |
| 2004/0186565 A1 | 9/2004 | Schreck | |
| 2004/0193261 A1 | 9/2004 | Berreklouw | |
| 2004/0230809 A1* | 11/2004 | Lowensohn | G06F 21/35 713/186 |
| 2004/0243104 A1 | 12/2004 | Seddon | |
| 2004/0243230 A1 | 12/2004 | Navia et al. | |
| 2005/0004665 A1 | 1/2005 | Aklog | |
| 2005/0004668 A1 | 1/2005 | Aklog et al. | |
| 2005/0006559 A1 | 1/2005 | Smith | |
| 2005/0035862 A1 | 2/2005 | Wildman et al. | |
| 2005/0038741 A1 | 2/2005 | Bonalle et al. | |
| 2005/0049157 A1 | 3/2005 | MacDonald et al. | |
| 2005/0079637 A1 | 4/2005 | Wilhelm et al. | |
| 2005/0088299 A1 | 4/2005 | Bandy et al. | |
| 2005/0090414 A1 | 4/2005 | Rich | |
| 2005/0134465 A1 | 6/2005 | Rice et al. | |
| 2005/0191326 A1 | 9/2005 | Melker | |
| 2005/0227880 A1 | 10/2005 | Shiloach et al. | |
| 2005/0231373 A1 | 10/2005 | Lynn et al. | |
| 2005/0233918 A1 | 10/2005 | Rich | |
| 2005/0233919 A1 | 10/2005 | Rich | |
| 2006/0025855 A1 | 2/2006 | Lashinski et al. | |
| 2006/0067545 A1 | 3/2006 | Lewis et al. | |
| 2006/0071799 A1* | 4/2006 | Verdiramo | G08B 21/245 340/573.5 |
| 2006/0111620 A1 | 5/2006 | Squilla et al. | |
| 2006/0132316 A1 | 6/2006 | Wildman et al. | |
| 2006/0184240 A1 | 8/2006 | Jimenez et al. | |
| 2006/0184241 A1 | 8/2006 | Marquez | |
| 2006/0214000 A1 | 9/2006 | Lapstun et al. | |
| 2006/0240397 A1 | 10/2006 | Lynn et al. | |
| 2006/0272361 A1 | 12/2006 | Snodgrass | |
| 2006/0273915 A1 | 12/2006 | Snodgrass | |
| 2007/0005129 A1 | 1/2007 | Damm et al. | |
| 2007/0008146 A1 | 1/2007 | Taylor et al. | |
| 2007/0080801 A1 | 4/2007 | Weismiller et al. | |
| 2008/0031838 A1 | 2/2008 | Bolling | |
| 2012/0062378 A1 | 3/2012 | Bolling | |
| 2012/0068843 A1 | 3/2012 | Bolling | |

FOREIGN PATENT DOCUMENTS

| | | |
|---|---|---|
| EP | 1 480 413 | 11/2004 |
| EP | 1 510 987 | 3/2005 |
| EP | 1 095 190 | 4/2005 |
| EP | 1 555 351 | 7/2005 |
| FR | 2 805 162 | 8/2001 |
| GB | 2 324 397 A | 10/1998 |
| JP | 2000-505576 | 5/2000 |
| JP | 2002-511923 | 4/2002 |
| JP | 2003-525655 | 9/2003 |
| JP | 3497079 | 11/2003 |
| WO | WO 93/15690 | 8/1993 |
| WO | WO 97/12565 | 4/1997 |
| WO | WO 97/20524 | 6/1997 |
| WO | WO 98/24386 | 6/1998 |
| WO | WO 98/36258 | 8/1998 |
| WO | WO 99/29269 | 6/1999 |
| WO | WO 99/49816 | 10/1999 |
| WO | WO 99/66138 | 12/1999 |
| WO | WO 00/44311 | 8/2000 |
| WO | WO 00/62715 | 10/2000 |
| WO | WO 00/67805 | 11/2000 |
| WO | WO 01/89440 | 11/2001 |
| WO | WO 02/059701 A1 | 1/2002 |
| WO | WO 03/080150 | 10/2003 |
| WO | WO 03/105670 | 12/2003 |
| WO | WO 03/105730 | 12/2003 |
| WO | WO 04/014282 | 2/2004 |
| WO | WO 04/030569 | 4/2004 |
| WO | WO 04/031717 | 4/2004 |
| WO | WO 04/073498 | 9/2004 |
| WO | WO 04/090760 | 10/2004 |
| WO | WO 04/090761 | 10/2004 |
| WO | WO 04/090796 | 10/2004 |
| WO | WO 04/090798 | 10/2004 |
| WO | WO 04/090803 | 10/2004 |
| WO | WO 04/103223 | 12/2004 |
| WO | WO 05/002424 | 1/2005 |
| WO | WO 05/007037 | 1/2005 |
| WO | WO 05/025963 | 3/2005 |
| WO | WO 05/046488 | 5/2005 |
| WO | WO 05/055046 | 6/2005 |
| WO | WO 06/086434 | 8/2006 |
| WO | WO 2007/001866 | 1/2007 |
| WO | WO 2011/031774 | 3/2011 |

OTHER PUBLICATIONS

Buergy et al., "Wearable Computers: An Interface between Humans and Smart Infrastructure Systems," *Carnegie Mellon University*, 1-13 (2002).

Cites and Abstracts from Search Results, 12 pages (Jun. 17, 2005).

Dunn et al., "Recommended Standards for Newborn ICU Design," *Report of the Sixth Census Conference on Newborn ICU Design*, Clearwater Beach, Florida, (Feb. 1, 2007).

Dunn et al., "Recommended Standards for Newborn ICU Design," *Report of the Sixth Census Conference on Newborn ICU Design*, Orlando, Florida (Jan. 25-27, 2006).

Echt et al., "Automated Abrasive Blasting Equipment for Use on Steel Structures," Taylor and Francis Ltd. Pub., *Applied Occupation and Environmental Hygiene*, 15(10) (Oct. 2000).

Figaro USA Inc., Technical Information for TGS2620, pp. 1-11 (Rev. 10/00).

Katz, "Hand Washing and Hand Disinfection: More Than Your Mother Taught You," *Anesthesiology Clinics of North America*, 22:457-471 (2004).

Patent Prior Art Search Results (US Only), 188 pages (Mar. 4, 2005).

Search Results, Cites and Abstracts (Oct. 14, 2005).

Search Results, Patent Keyword Search (Mar. 10, 2005).

Supplemental European Search Report for Application Serial No. EP 06 77 3178, dated Apr. 20, 2010, 4 pages.

U.S. Patent Prior Art Search by Assignee, "Ultraclenz Engineering Group", pp. 1-3 (May 16, 2006).

U.S. Search Results, Cites and Abstracts From Accession No. Retrieval, pp. 1-12 (Mar. 11, 2005).

Australian Office Action for App. Ser. No. 2006262524, dated Jan. 27, 2010, 1 page.

Australian Office Action for App. Ser. No. 2011240297, dated Jun. 22, 2012, 2 pages.

Canadian Office Action for App. Ser. No. 2,612,748, dated Sep. 25, 2012, 2 pages.

Chinese Office Action for App. Ser. No. 200680030305.0, dated Apr. 13, 2010, 4 pages.

Chinese Office Action for App. Ser. No. 200680030305.0, dated Oct. 26, 2011, 25 pages.

Chinese Office Action for App. Ser. No. 200680030305.0, dated Jun. 4, 2012, 34 pages (with English translation).

(56) References Cited

OTHER PUBLICATIONS

Chinese Office Action for App. Ser. No. 200680030305.0, dated Jan. 11, 2013, 4 pages (with English translation).
Japanese Office Action for App. Ser. No. 2008-518244, dated Jan. 17, 2012, 5 pages.
Japanese Office Action for App. Ser. No. 2008-518244, dated Sep. 4, 2012, 5 pages (with English translation).
International Search Report for Application Serial No. PCT/US06/23204, dated May 8, 2007, 16 pages.
International Search Report for Application Serial No. PCT/US06/23204, dated Nov. 30, 2007, 16 pages.
International Preliminary Report on Patentability for Application Serial No. PCT/US06/23204, dated Aug. 16, 2007, 10 pages.
International Preliminary Report for Application Serial PCT/US06/023204, dated Apr. 2, 2009, 11 pages.
International Search Report for Application Serial No. PCT/US08/50224, dated Jul. 1, 2008 (13 pages).
International Preliminary Report on Patentability for Application Serial No. PCT/US07/72625, dated Feb. 3, 2009, 7 pages.
International Search Report for Application Serial No. PCT/US07/72625, dated Dec. 18, 2007, 11 pages.
International Search Report and Written Opinion for App. Ser. No. PCT/US2010/048150, dated Dec. 6, 2010, 11 pages.
International Preliminary Report on Patentability for App. Ser. No. PCT/US2010/048150, dated Mar. 13, 2012, 6 pages.
U.S. Appl. No. 11/876,267, filed Oct. 22, 2007, including application as filed, pending claims, and transaction history. (now U.S. Pat. No. 7,482,936).
U.S. Appl. No. 11/353,746, filed Feb. 14, 2006, including application as filed, pending claims, and transaction history. (now U.S. Pat. No. 7,616,122).
U.S. Appl. No. 11/415,687, filed May 1, 2006, including application as filed, pending claims, and transaction history (now U.S. Pat. No. 7,936,275).
U.S. Appl. No. 11/498,465, filed Aug. 3, 2006, including application as filed, pending claims, and transaction history (published as 2008/0031838).
U.S. Appl. No. 11/157,094, filed Jun. 20, 2005 (now U.S. Pat. No. 7,286,057), including patent and transaction history.
U.S. Appl. No. 12/614,822, filed Nov. 9, 2009, including pending claims and transaction history (now U.S. Pat. No. 7,982,619).
U.S. Appl. No. 12/877,596, filed Sep. 8, 2010 (published) (U.S. 2011/0206378).
U.S. Appl. No. 13/184,988, filed Jul. 18, 2011.
U.S. Appl. No. 13/099,207, filed May 2, 2011.
Office Action for Canadian App. Ser. No. 2612748, dated Oct. 17, 2013, 3 pages.
Notification concerning Transmittal of International Preliminary Report on Patentability for App. Ser. No. PCT/US2012/041371, dated Dec. 27, 2013 (10 pages).
Japan Patent Office, "Notification of Reasons for Rejection," JP Application No. 2008-518244, dated Dec. 3, 2013 (5 pages).

* cited by examiner

BioVigil

View Badges
View Users
View Locations
View Badge Events

Create a Badge
Create a Sensor Location
Create a User
Create a Report

Today's Badge Events
Today's Event Count: 87
Clean Percentages: 66%

| Badge | Badge User | Location | Trigger Type | Hand Status | Event Time |
|---|---|---|---|---|---|
| B0001 | Bill Simpson | G0001 – ER 1 | Location Trigger | Clean | 01-29-2009 20:47:32 |
| B0002 | Mary Hanford | G0003 – Pediatrics 3 | Location Trigger | Clean | 01-29-2009 20:36:14 |
| B0003 | Jan Schremp | G0005 – Pediatrics | Location Trigger | Clean | 01-29-2009 20:27:52 |
| B0004 | Joel Stevens | G0002 – OR 5 | Location Trigger | Dirty | 01-29-2009 20:26:14 |
| B0001 | Bill Simpson | G0001 = ER 1 | Location Trigger | Clean | 01-29-2009 20:21:37 |
| B0003 | Jan Schremp | G0005 – Maternity 4 | Location Trigger | Clean | 01-29-2009 20:16:45 |
| B0005 | Greg Hooper | G0008 – ICU 6 | Location Trigger | Dirty | 01-29-2009 20:02:13 |
| B0006 | Karen White | G0009 – Pediatrics 3 | Location Trigger | Clean | 01-29-2009 19:56:24 |

Badges

| Badge ID | Name |
|---|---|
| B0001 | Bill Simpson |
| B0002 | Mary Hanford |
| B0003 | Jan Schremp |
| B0004 | Joel Stevens |
| B005 | Grag Hooper |
| B0006 | Karen White |

FIG. 21

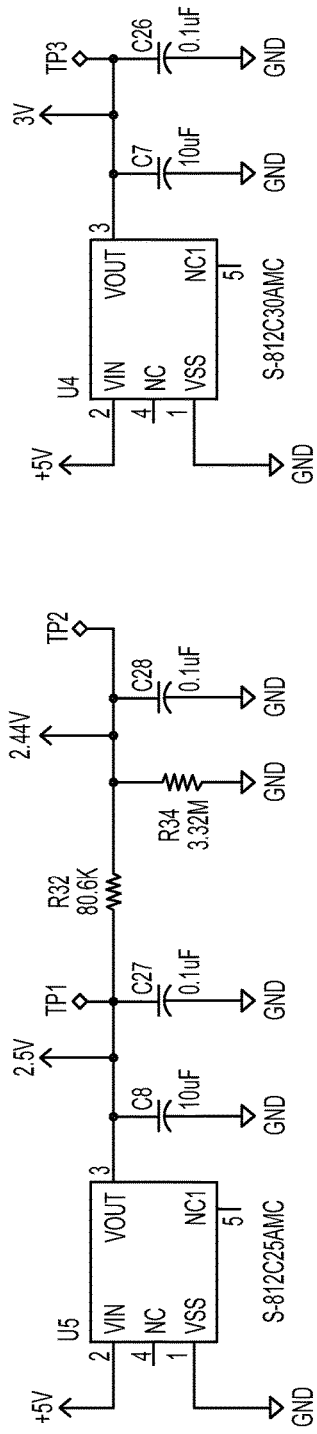
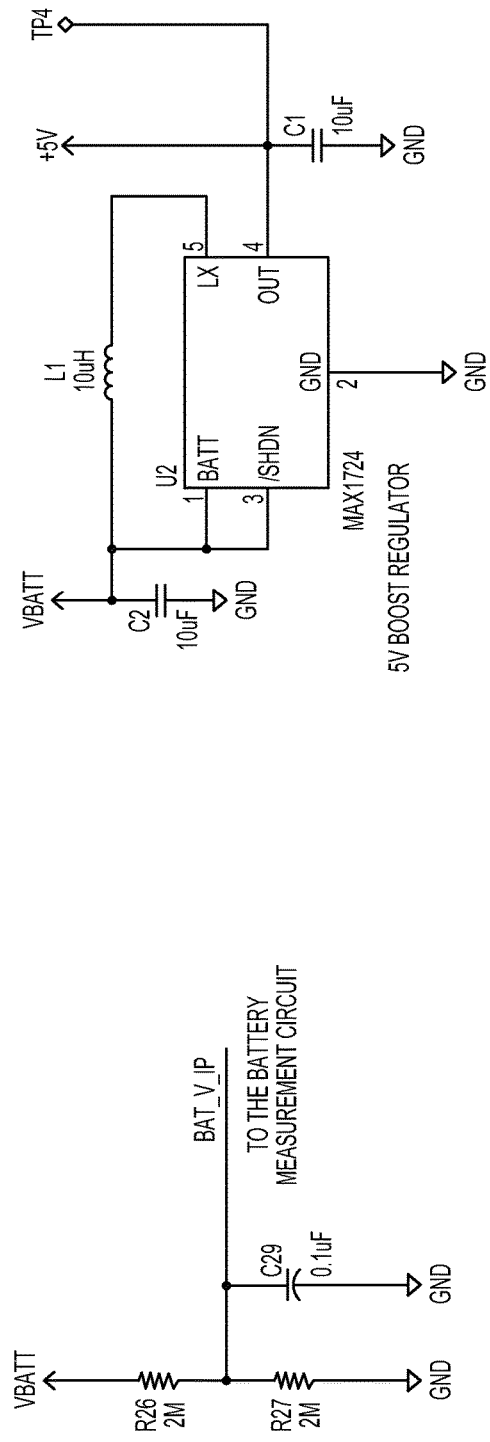
FIG. 25A

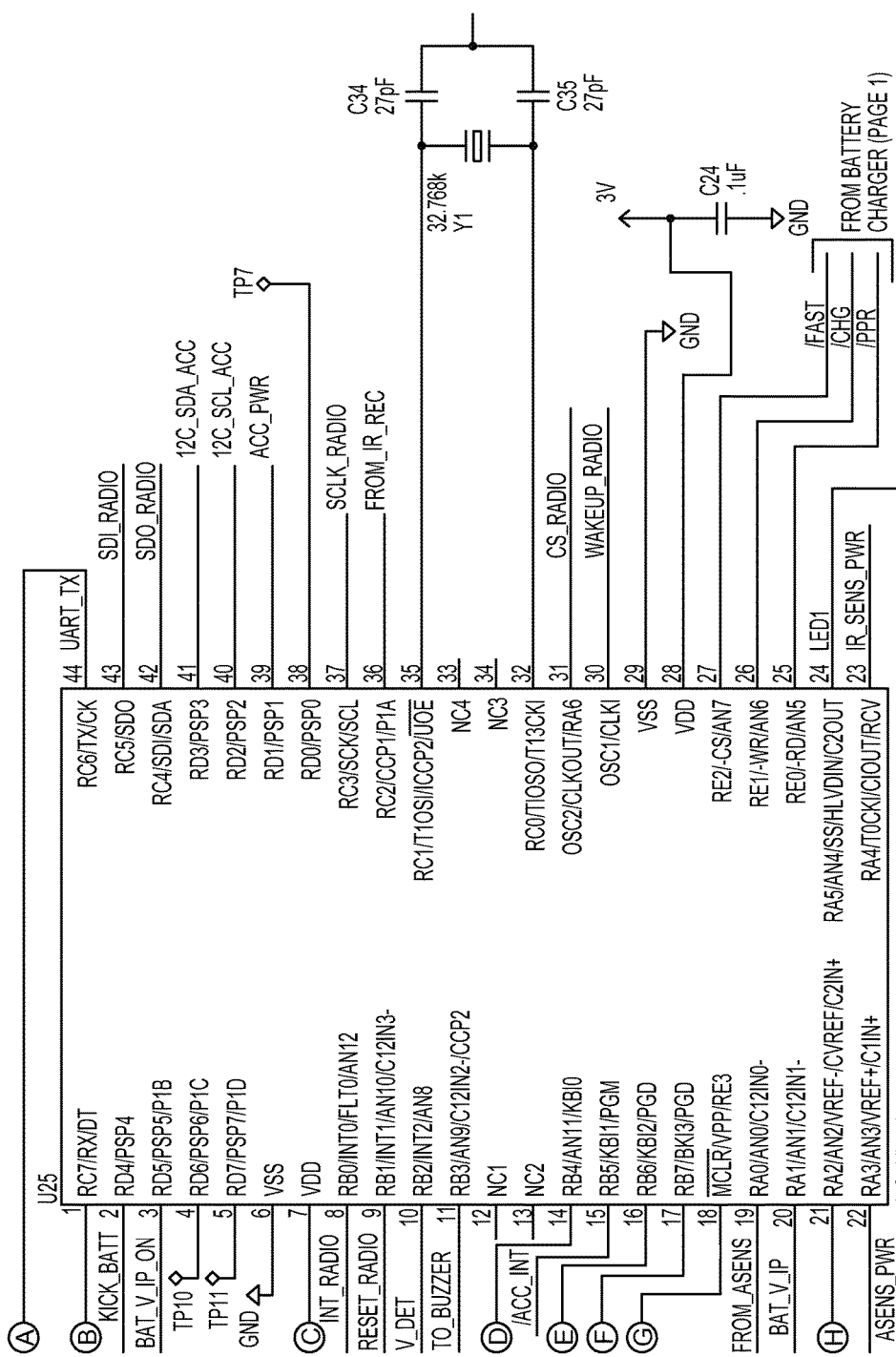

HAND CLEANLINESS

This application is a continuation of and claims the benefit of U.S. application Ser. No. 12/877,596, entitled Hand Cleanliness, filed Sep. 8, 2010, to be issued U.S. Pat. No. 8,502,681 on Aug. 6, 2013, which claims benefit to U.S. provisional patent application Ser. 61/240,622, filed Sep. 8, 2009, which is a continuation-in-part of U.S. patent application Ser. No. 11/415,687, entitled Hand Cleanliness, filed May 1, 2006, which is a continuation-in-part of U.S. patent application Ser. No. 11/353,746, entitled Hand Cleanliness, filed Feb. 14, 2006, which is a continuation-in-part of U.S. patent application Ser. No. 11/157,094, entitled Hand Cleanliness, filed Jun. 20, 2005, the contents of all of which are incorporated here by reference.

BACKGROUND

This description relates to boundary identification and hand cleanliness.

Health care workers, food handlers, and others ought to clean their hands frequently and thoroughly, but they often don't. Better hand cleaning habits can be promoted by governmental regulations, company rules, social pressure, and technology. Techniques that have been proposed for improving cleaning habits include the use of special cleaning agents as well as mechanisms and electronic devices to regulate, monitor, and report on how frequently and how effectively people clean their hands.

SUMMARY

In general, the systems and methods described can be used for monitoring when devices (e.g., wearable badges, equipment tags, theft prevention tags) cross monitored boundaries such as doorways in a hospital. Each boundary can be delineated by pairs of emitters one of which is associated with a first side of the boundary and the other of which is associated with an opposite second side of the boundary. For example, a pair of emitters can be associated with a specific doorway. One emitter can have a signal indicating that the emitter is located "outside" the doorway (e.g., in a hallway). The other emitter can have a signal indicating that the emitter is located "inside" the doorway (e.g., in a room entered from the hallway). The systems and methods described can provide a high-level of reliability in indicating when devices (e.g., wearable badges, equipment tags) cross monitored boundary while limiting emissions in areas spaced apart from the boundary (e.g., the patient care portion of a hospital).

In some embodiments, the systems and methods described can be implemented using infrared (IR) emitters. In some cases, the devices (e.g., wearable badges, equipment tags) being used to track movement, for example, of people and/or equipment can include onboard emitters used to transmit information from the devices to external receiving equipment. The onboard emitters can be switched from a default inactive state to an active state to transmit information upon receipt of a specific signal associated with the external receiving equipment. This approach can limit emissions (e.g., radio frequency emissions) from the devices except when devices are triggered to download information to the external receiving equipment. For example, it can be desirable to limit emissions and the patient care portion of a hospital room.

In an aspect, in systems to encourage compliance with hand washing procedures, the systems include: an infrared emitter that projects a first infrared beam with a transverse cross-section having a first axis and a second axis that is shorter than the first axis, the transverse cross-section having a maximum length along the first axis, the infrared emitter modulating the first infrared beam to transmit a first identification signal; wherein the infrared emitter projecting the first infrared beam is placed such that the first axis of the transverse cross-section of the first infrared beam is substantially parallel to a boundary. Implementations may include one or more of the following features.

In some embodiments, systems include an infrared emitter that projects a second infrared beam with a transverse cross-section having a first axis and a second axis that is shorter than the first axis, the transverse cross-section having a maximum length along the first axis, the infrared emitter modulating the second infrared beam to transmit a second identification signal; wherein the infrared emitter projecting the second infrared beam is placed such that the first axis of the transverse cross-section of the second infrared beam is substantially parallel to the boundary on an opposite side of the boundary from the first infrared beam. In some cases, the infrared emitter that projects the first infrared beam is a first infrared emitter and the infrared emitter that projects the second infrared beam is a second infrared emitter. The boundary can be defined by a doorway though a wall and the first infrared emitter can be attached to the wall on one side of the doorway and the second infrared emitter can be attached to the wall on an opposite side of the doorway.

In some embodiments, systems include a wearable device comprising: an infrared receiver; an indicator operable to indicate a cleanliness state of a user's hands; and a control unit operable to control the indicator of hand cleanliness based at least on part based input from the infrared receiver. In some cases, the controller of the wearable device comprises logic operable, on receiving the infrared receiver, to evaluate whether wearable device is crossing the boundary.

In some embodiments, the infrared emitter projecting the first infrared beam has elements to attach it to a wall and the boundary is implied by the wall.

In some embodiments, a ratio of a length of the first axis of the first infrared beam to a length of the second axis of the first infrared beam is at least 3:1.

In some embodiments, the infrared emitter projects the first infrared beam downwards towards a floor and an average length of the first axis of the first infrared beam is between about 20 and 28 inches. In some cases, an average length of the second axis of the first infrared beam is between about 6 and 10 inches.

In some embodiments, systems include a plurality of emitters and each emitter is operable to transmit an identity signal that includes information identifying the transmitting emitter.

In general, in an aspect, methods include: receiving, on a wearable device, a first signal representative of a first location; evaluating whether the first wearable device is crossing a boundary associated with the first signal; controlling a cleanliness state of the wearable device based on results of the evaluation. Implementations may include one or more of the following features.

In some embodiments, evaluating whether the wearable device is entering or leaving a location associated with the first signal comprises comparing the first signal with a previously stored signal. In some cases, methods include evaluating whether the wearable device is entering or leaving a location associated with the first signal if the previously stored location signal is the same as the first signal. In some cases, controlling the cleanliness state comprises controlling the wearable device to an un-sanitized state if the first signal is different than a most recently stored signal.

In some embodiments, receiving the signal comprises receiving an infrared signal.

In general, in an aspect, in systems to encourage compliance with hand washing procedures, the systems include: an emitter that projects a first beam with a transverse cross-section having a first axis and a second axis that is shorter than the first axis, the transverse cross-section having a maximum length along the first axis, the infrared emitter modulating the first beam to transmit a first identification signal; wherein the emitter projecting the first beam is placed such that the first axis of the transverse cross-section of the first beam is substantially parallel to a boundary. Implementations may include one or more of the following features.

In some embodiments, the emitter is a radiofrequency transmitter. In some cases, the emitter comprises shielding configured to limit lateral transmission of a radiofrequency signal emitted by the radiofrequency transmitter.

In some embodiments, the emitter comprises an infrared emitter.

In some embodiments, the emitter is configured to project the first beam in response to a signal from a motion detector.

In general, in an aspect, in systems to encourage compliance with hand washing procedures, the systems include: a first infrared emitter that projects a first infrared beam with a transverse cross-section having a first axis and a second axis that is shorter than the first axis, the transverse cross-section having a maximum length along the first axis, the first infrared emitter modulating the first infrared beam to transmit a first identification signal; a second infrared emitter that projects a second infrared beam with a transverse cross-section having a first axis and a second axis that is shorter than the first axis, the transverse cross-section having a maximum length along the first axis, the second infrared emitter modulating the second infrared beam to transmit a second identification signal; wherein the first infrared emitter is placed such that the first axis of the transverse cross-section of the first infrared beam is substantially parallel to a boundary; and wherein the second infrared emitter projecting the second infrared beam is placed such that the first axis of the transverse cross-section of the second infrared beam is substantially parallel to the boundary. Implementations may include one or more of the following features.

In some embodiments, the systems include a wearable device including: an infrared receiver; an indicator operable to indicate a cleanliness state of a user's hands; and a control unit operable to control the indicator of hand cleanliness based at least on part based input from the infrared receiver.

In some embodiments, the first and second infrared emitters have elements to attach the first and second infrared emitters to a wall and the boundary is implied by the wall.

In some embodiments, the systems include a plurality of emitters and each emitter is operable to transmit an identity signal that includes information identifying the transmitting emitter.

In some embodiments, the first infrared beam carries information indicative of which one of two sides of the boundary the first emitter is on.

In general, in an aspect, methods in which information is communicated wirelessly about a location of a boundary in a space that is traversed by people whose hands need to be clean, the wireless communication being communicated in such a way that a device worn by the person can determine in which direction the person has traversed the boundary.

In general, in an aspect, methods in which a device worn by a person can determine from received wireless communications the direction in which the person has traversed a boundary of a space in which the person is walking or traversing.

Implementations may include one or more of the following features.

In some embodiments, the methods include receiving, on the device worn by the person, a first signal representative of a location of an emitter; evaluating whether the device worn by the person is crossing a boundary associated with the first signal; and controlling a cleanliness state of the wearable device based on results of the evaluation. In some cases, evaluating whether the device worn by the person is entering or leaving a location associated with the first signal comprises comparing the first signal with a previously stored signal. Determining the device worn by the person is entering or leaving a location associated with the first signal if the previously stored location signal is not the same as the first signal. In some cases, controlling the cleanliness state comprises controlling the wearable device to an un-sanitized state if the first signal is different than a most recently stored signal.

In some embodiments, receiving the signal comprises receiving an infrared signal.

In general, in an aspect, apparatuses include: a first wearable device including: a controller operable, on receiving a signal from a sentinel, to evaluate whether wearable device is crossing a threshold monitored by the sentinel; an indicator coupled to the controller, the indicator operable to indicate a cleanliness state of a user's hands; and a wireless communication element coupled to the controller, the wireless communication element operable to receive the wireless signal transmitted by the emitter; wherein the controller is configured to set the indicator to a not-disinfected state in response to the wireless signal transmitted by the emitter. Implementations may include one or more of the following features.

In some embodiments, the controller of the first wearable device comprises logic operable, on receiving the signal from the sentinel unit, to compare relative signal strengths of signals received from the sentinel unit at different times.

In some embodiments, the controller of the first wearable device comprises logic operable, on receiving the signal from the sentinel unit, to compare the identity signal with a stored identity signal.

In some embodiments, the wearable device comprises a motion sensing device coupled to the controller, the motion sensing device operable to send information to the controller about motion of the wearable device; and the controller is configured to shut down the controller, the sensor, and the motion sensing device when the information from the motion sensing device has not indicated motion for a set period of time.

In some embodiments, the systems and methods described can provide a high-level of reliability in indicating when devices (e.g., wearable badges, equipment tags) cross monitored boundary while limiting emissions in areas spaced apart from the boundary (e.g., the patient care portion of a hospital room). In some cases, selective activation of onboard emitters (e.g., upon receipt of a specific signal associated with external receiving equipment) can further limit emissions (e.g., radio frequency emissions) from the devices except when devices are triggered to download information to the external receiving equipment at locations spaced apart from, for example, the patient care portion of a hospital room.

Other advantages and features will become apparent from the following description and from the claims.

DESCRIPTION

FIG. 1 is a perspective view of a badge.

FIGS. 2, 3, and 4 are schematic plan views of three layers of the badge.

FIG. 21 illustrates a graphical user interface.

The system described here can be used for monitoring, encouraging, and managing the hand cleanliness of people who work or are otherwise present in places where hand cleanliness is important, for example, to reduce the spread of disease or to reduce contamination of products that are being manufactured or for other purposes. Important purposes of the system include encouraging or even enforcing hand cleanliness, reporting compliance with institutional or governmental requirements for hand cleanliness, and permitting the central and institutional control and management of hand cleanliness enforcement and reporting.

Figure 1:
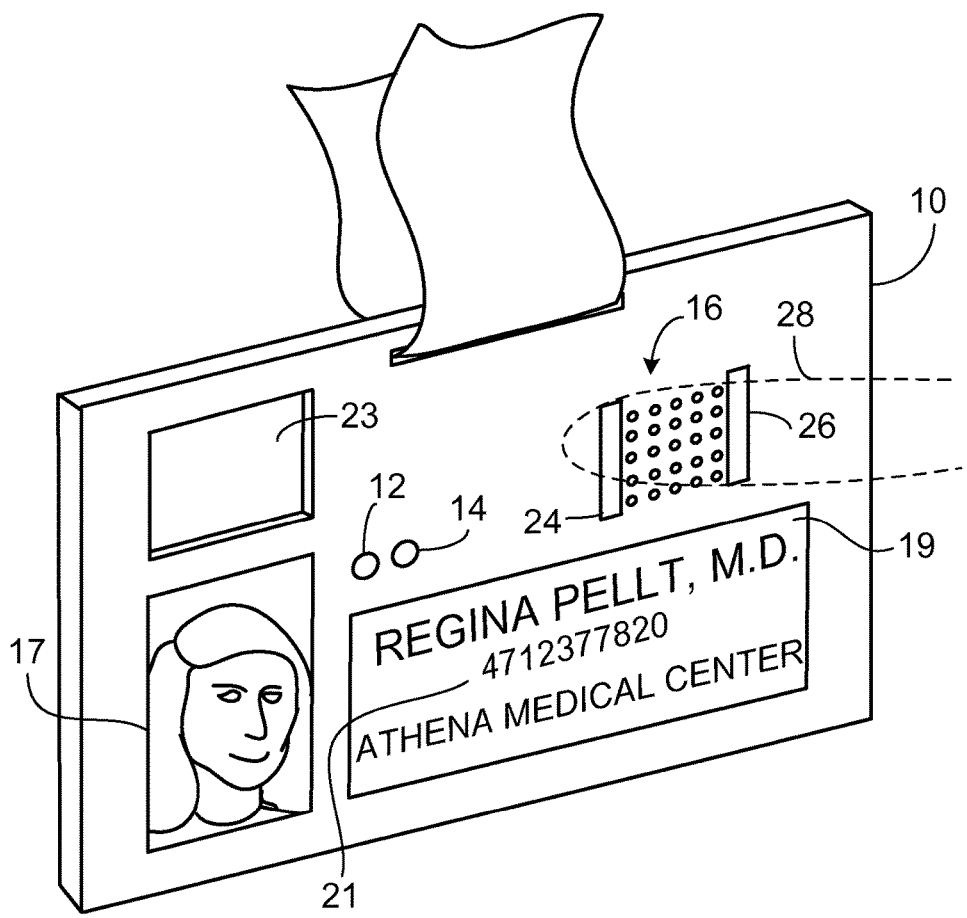

As shown in FIG. 1, in some examples, an identification badge 10 worn by a doctor has red and green lights 12, 14, that indicate that her hands are likely to be respectively in a clean (e.g., disinfected, green light) condition or in a not clean (e.g., not disinfected, red light) condition. The two lights are controlled by a control circuit (not shown in FIG. 1) based on (a) information derived from an alcohol (e.g., ethanol) sensor 16 in the badge, (b) signals from a timer (also not shown in FIG. 1) that tracks the passage of time after the circuit has determined that the hands are likely to be in a disinfected condition, and (c) the state of the logic implemented by the control circuit (also not shown). An LCD display 23 provides displayed information that can include the status of the badge, the control circuit, or the sensor; the time; the status of the cleanliness of the doctor's hands; and other information.

In addition to providing the disinfection determining function, the badge 10 can be of a shape and form and can display information sufficient to serve a conventional function of complying with government and institution regulations that require health care workers to carry visible identification. For example, the badge includes a photograph 17 of the doctor, and other information including the doctor's name 19 and identification number 21. A typical badge could be approximately credit-card size.

Because health care workers are required to carry such badges for other reasons, providing the disinfection determining function within the same badge make it more likely that the worker will use that function than if the function were provided in a separate device that the worker was expected to carry separately. In addition, because the badge worn by a worker must be visible to others in the health care environment, the feature of the badge that indicates whether the user's hands are clean or unclean will naturally be visible to others. Thus, the worker, merely by having to wear the badge, will be subjected to social pressure of peers, patients, and managers with respect to the cleanliness of the worker's hands. This makes the use of the disinfection determining feature of the badge and the improvement of cleanliness habits self-enforcing. The institution by whom the worker is employed need only provide badges that include those features without directly managing or monitoring their use.

A pair of electrodes 24, 26 on either side of the sensor is used to determine when a finger 28 or other part of the hand or other skin has been placed against or near the sensor. When skin of a finger or other part of the hand touches both electrodes, the resistance between them will decline. By measuring that resistance the control circuit can detect the presence of a finger.

The badge is used by the doctor in conjunction with disinfecting her hands using cleaners of the kind that include ethanol (for example, the liquid known by the name Purell available from GOJO Industries, Akron, Ohio, and which contains 62% ethyl alcohol). Such cleaners are considered to be more effective than soaps and detergents in killing bacteria and viruses and are widely used in health care and other environments. When the ethanol-based cleaner is rubbed on the skin of the hands, the ethanol kills the bacteria and viruses. The effect will last for several hours but eventually wears off. Ethanol is volatile and eventually evaporates from the skin, leaving the possibility (which increases over time) that live bacteria and viruses will again contaminate the skin from the air and from objects that are touched, for example.

The concentration of ethanol on the skin and the decay of that concentration from evaporation tend to determine the onset of subsequent contamination. In turn, the concentration of ethanol on the skin can be inferred by the concentration of ethanol vapor near the skin. By placing the skin near an ethanol detector for a short period of time, it is possible to determine the vapor concentration of ethanol and thus to infer the ethanol concentration on the skin and the disinfected state of the skin. When the current inferred concentration is above a threshold, it is possible to make an assumption about how long the hands will remain disinfected.

The badge can be used in the following way to improve the hand cleaning habits of the user.

In some simple examples, the badge can be configured to determine and display two different states: disinfected and not disinfected.

Except when the badge has recently enough (say within two or three hours) entered the disinfected state due to a measurement cycle in which an adequate concentration of ethanol vapor had been sensed, the badge will assume a default state of the user's skin of not disinfected. Thus, when the badge is first powered on, or reset, or the permitted time since a prior successful measurement has elapsed, the state becomes not disinfected. When the state is not disinfected the red light is lit and the word re-test is displayed on the LCD.

In some implementations, the badge can be made to switch from the not disinfected state to the disinfected state only by a successful ethanol measurement cycle. A successful cycle is one in which a finger or other part of the body is held in position over the sensor (touching both of the electrodes) for a period that is at least as long as a required measurement cycle (e.g., 30 seconds or 45 seconds or 60 seconds depending on the design of the circuit), and the concentration of ethanol vapor that passes from the skin into a measurement chamber of the sensor is high enough to permit an inference that the skin is disinfected.

Thus, when the doctor wipes her hands with the cleaner to disinfect them, she can then press one of her clean fingers against the sensor 16 and the two electrodes 24, 26, for, say, 60 seconds.

Touching of both of the electrodes simultaneously by the finger is detected by the control circuit which then begins the measurement cycle. The control circuit could start the red and green lamps to flash alternately and to continue to do so as an indication to the user that the electrodes are both being touched and that the measurement cycle is proceeding. At the end of the sensing cycle, the control circuit determines a level of concentration of ethanol and uses the level to determine whether the finger, and by inference, the hand of the doctor is disinfected. Each time a measurement cycle has been fully completed, the red and green lights may both be flashed briefly to signal that the cycle has ended and the finger may be removed.

The control circuit continually monitors the electrodes to determine when a finger or other skin is touching both of the electrodes. When that event is detected, a measurement cycle count down timer (which is initialized for the number of seconds needed to complete a measurement) is started. At the beginning of a cycle, a voltage is applied to the heater to begin to heat the sensor element. Initially the heater voltage may be set to a higher than normal value in order to shorten the initial action period described below. Then the heater voltage is reduced. At the end of the measurement cycle, a measurement voltage is applied across the series connection of the measurement cell and the series resistor, and the voltage across the series resistor is detected and compared to a threshold to determine whether the state should be set to disinfected or not disinfected.

When the control circuit determines that the hand is disinfected, the control circuit switches to the disinfected state, lights the green lamp (and turns off the red lamp), and displays the word clean on the LCD. In addition, upon the initiation of the disinfected state, the control circuit starts a re-test count down timer that is initially set to the period during which the skin is expected to remain disinfected (for example two hours).

If the control circuit is in the disinfected state and the user voluntarily performs another successful measurement cycle (for example, if, during the two hours after the prior successful measurement, she disinfects her hands again), the re-test count down timer is reset.

Anyone in the vicinity of the doctor who can see the lights or LCD is made aware of whether, according to the doctor's use of the badge, the doctor's hands are disinfected or not. People who find troubling the indication that a person's hands are not disinfected can complain to the person or to the employer, for example.

During the sensing cycle the doctor must keep her finger against the sensor for at least a certain period of time, say 60 seconds, to give the sensor and the control circuit time to obtain a good reading. If the doctor removes her finger before the end of the period, the control circuit remains in or switches to the not disinfected state and displays the word re-test on the LCD display.

If the doctor holds her finger against the sensor long enough to complete the sensing cycle, the results of the sensing cycle are displayed on the LCD and by lighting either the red light or the green light.

If the sensing cycle ends with a determination that the finger is not disinfected, the doctor can try again to apply enough of the cleaner to her hands to satisfy the circuit and can test the ethanol concentration again. And the cycle can be repeated until the disinfected state is determined.

In addition to causing the green light to be illuminated and the LCD to show clean, successfully completing an ethanol test also causes the control circuit to reset a count down timer (not shown in FIG. 1) to a predetermined period (say, two hours) after which it is assumed that the benefit of the ethanol treatment has worn off and the doctor's hands are no longer disinfected. When the timer times out at the end of the predetermined period, the control circuit turns off the green light, lights the red light, and changes the displayed word from clean to re-test. The red light stays on and the word re-test continues to be displayed until a successful ethanol test is performed by the doctor.

Figure 2:
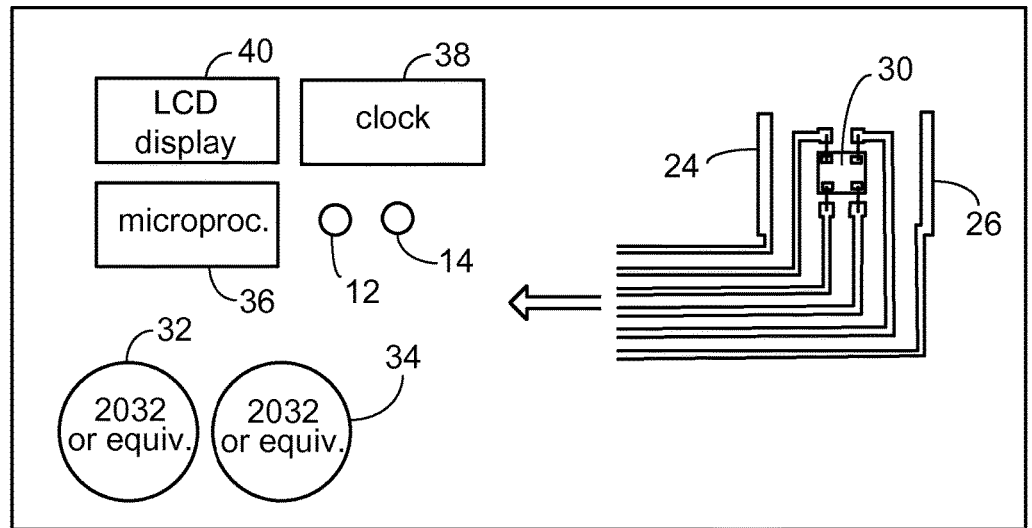
Figure 3:
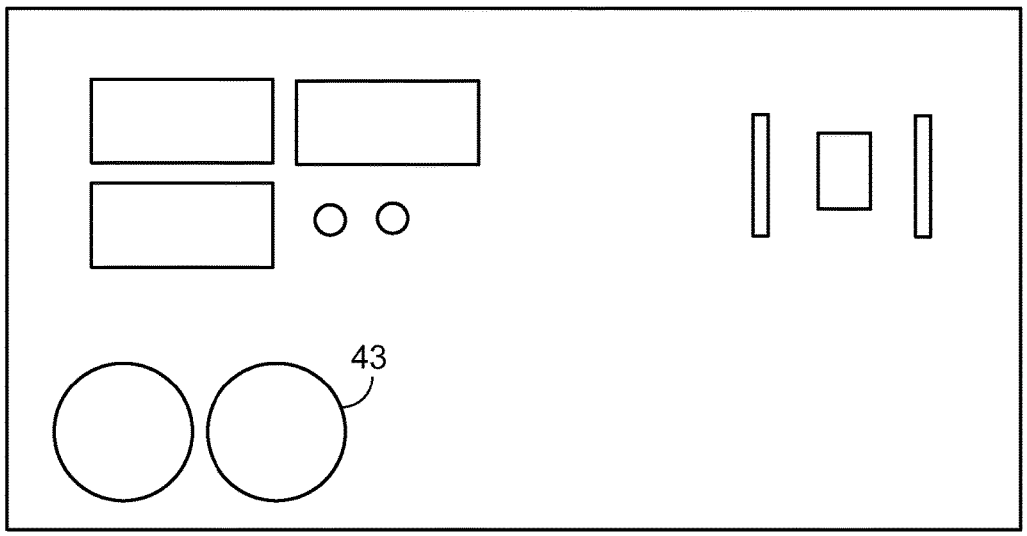
Figure 4:
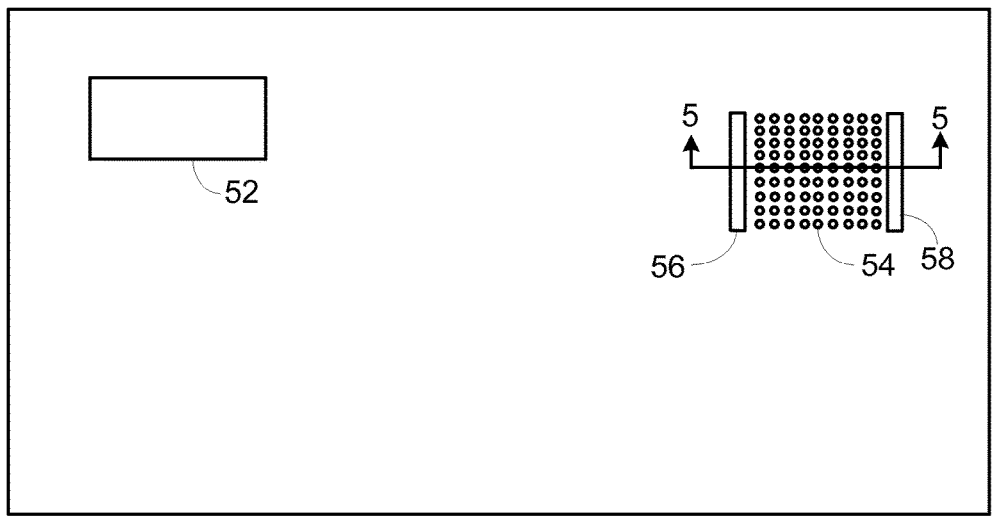

As shown in FIGS. 2, 3, and 4, the badge 10 can be fabricated by assembling three layers.

A bottom layer 29 (shown schematically in FIG. 2) contains a printed circuit 31 and components mounted on the circuit. The components include the sensor element 30 of the sensor, two thin batteries 32, 34, a microprocessor 36 (an example of the control circuit mentioned earlier), a clock 38 (an example of the timer circuit mentioned earlier that can be used both for the measurement count-down timer and for the re-test count-down timer), the two LED lamps 12, 14, and an LCD display device 40. The detailed interconnections of the devices mounted on the bottom layer are not shown in FIG. 2. The control circuit could be, for example, a PIC microcontroller available from Microchip Technology, Inc. of Chandler, Ariz.

A middle layer (shown schematically in FIG. 3) is thicker than the bottom and top layer and provides physical relief for the components mounted on the bottom layer. The patterns shown in FIG. 3 represent cutouts 43 or perforations in the middle layer.

A top layer 50 (shown schematically in FIG. 4) includes a non-perforated and non-printed clear region 52 to permit viewing of the LCD display. Space is left for adding a photograph and other information as show in FIG. 1. A perforated region 54 provides openings for passage of ethanol vapors into the badge and two perforations 56, 58 on opposite sides of the perforated region 54 accept the conductive electrodes that are used to detect the presence of a finger.

Figure 5:
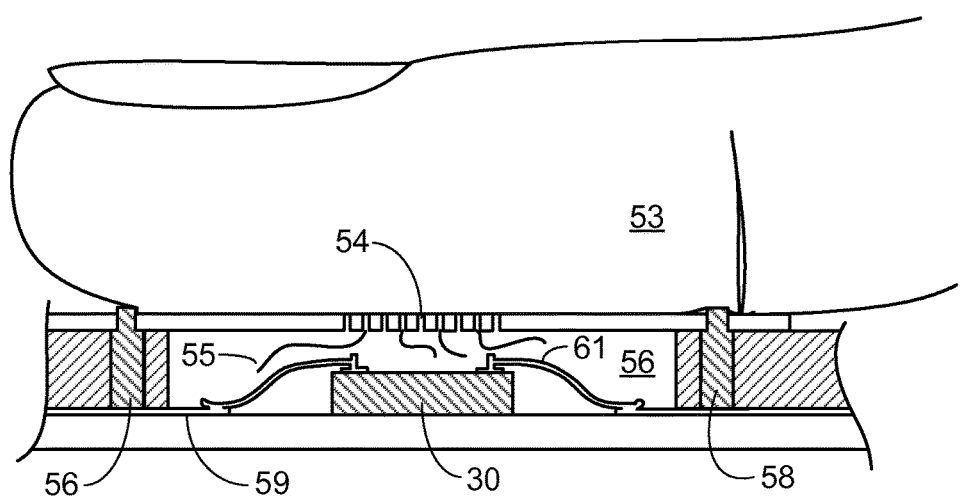
FIG. 5 is a sectional side view of a chamber at 5-5 in FIG. 4.

As shown in FIG. 5, the arrangement of the three layers in the vicinity of the sensor provides a sensing chamber 56. Ethanol vapors 55 pass from the finger 53 through the holes in perforated region 54 (which is shown as narrower than in FIG. 4) and into the chamber. Within the chamber is a tin oxide sensor element 30 (which includes an integral heater). The sensor element is connected by wire bonded connections 61 to circuit runs 59 on the bottom layer of the badge. The heater heats the vapors within the chamber and sensor element measures the concentration of ethanol.

Tin oxide sensors are small, low cost, and relatively low in power requirements. An example of a tin oxide ethanol sensor is the Model TGS 2620-M available from Figaro USA Inc. of Glenview, Ill., although other sensors available from other vendors could be used.

The sensor includes an integral heater and four connections, two for the sensor element, and two for the heater. By wiring a resistor in series with the element and measuring the voltage drop across the resistor, the control circuit can determine the amount of current flowing in the element and hence the resistance of the element which will vary with ethanol concentration.

Tin oxide sensors with heaters are subject to a so-called initial action that occurs when the sensors are not energized for a period and then are energized. The resistance of the sensor drops sharply during an initial period of energization, whether gases are present in the surrounding air or not. The longer the period of unenergized storage (up to about 30 days), the longer the period of the initial action. Therefore using tin oxide sensors in the badges requires a trade off between powering their operation for a period longer than the initial action but not so long that the energy drain caused by measurement cycles reduces the lifetime of the battery to an unacceptably short period. Experiments suggest that if the user keeps her finger in contact with the sensor for at least 20 or 30 seconds, the sensing of ethanol then begins to dominate the initial action and permits detection of the ethanol concentration. Other approaches may provide a shorter initial action (such as applying a larger voltage for the first few seconds of operation and then the normal voltage after that).

The badge provides a simple, effective, portable, and inexpensive way to confirm that the ethanol treatment has occurred no longer than, say, two hours ago, which likely means that the hands remain disinfected. No other external equipment is needed. The disinfection condition is apparent to anyone in the vicinity of the doctor, including patients, supervisors, regulators, and peers. The social pressure associated with being identified easily as not having disinfected hands is an effective way to improve the frequency and thoroughness of cleaning. The system does not force the doctor to comply. Compliance with cleaning rules and policies may remain less than perfect using the badges, yet it is likely that the compliance will improve significantly. Any degree of improvement translates into reduced costs and injuries now associated with hands that have not been disinfected.

Although we sometimes have referred to use of the system by a doctor, it is also useful for a wide variety of other people, including other health care workers, clean room workers, and guests, consumers, vendors, employees, and other parties involved in any kind activity in which cleanliness of the hands or other parts of the body is important.

For example, although a simple matching of a measured ethanol concentration against a threshold can be used to determine simply whether the state should be disinfected or not disinfected, it is also possible to provide a more complicated analysis of measured concentration over time and a comparison of the measured concentration against dynamically selected thresholds.

More than two states would be possible, for example, to denote different levels of disinfection or to denote that longer periods of time may elapse before another measurement is required.

The length of time before a first measurement is considered stale and another measurement is required need not be based on an estimate of how long the ethanol on the skin will be effective, but can be based on an arbitrary period such as every hour.

The degree of accuracy and repeatability of the measurement of ethanol concentration may be traded with the cost and complexity of the circuitry needed to do the measurements. In some examples, the goal need not be to assure that the user's hands are thoroughly disinfected at all times. Rather, if the system encourages more frequent and more thorough cleaning to any noticeable degree, great benefits will result. Thus a very simple system may be quite useful and effective even though it may allow some users to cheat and may fail to determine the state accurately at all times.

Additional lights and displayed words may be used for a variety of purposes. The approach of the end of the disinfected period could be indicated by a yellow light to alert the user that a cleaning would soon be needed.

The lights and LCD display could be supplemented with or replaced by audible alerts for all functions or some of them.

In some examples, not all of the circuitry need be mounted in a single badge. Some of the circuitry could be located in a different piece of equipment. For example, a sensor used in common by many people may be mounted on a wall and convey (say by wireless communication) the measured concentration of ethanol to the badge, which would then determine the state and indicate that state through lights and on the LCD. By separating the two, the badge could be lower cost, the sensor could be more complex and accurate, and the sensor could be located at places where the disinfectant solution is dispensed. Fewer sensors would be needed.

Each badge could itself be split into two components that communicate with each other wirelessly or by wire. For example, a sensor module could be located in the user's pocket, while the badge contains only the logic circuitry.

The cleaning agent that is being measured need not be limited to ethanol but could include combinations of ethanol with other materials or other materials in the absence of ethanol; an appropriate sensor for the other materials would be used.

The badge could include clips, hook and loop fasteners, chains, pins, ribbons, and belt loops, and other devices to hold the badge on the user.

The device need not take the form of a badge but could be an ID device that attaches to a belt, a lapel, any other article of clothing, and other parts of the body including an arm, a leg, or a neck.

Figure 8:
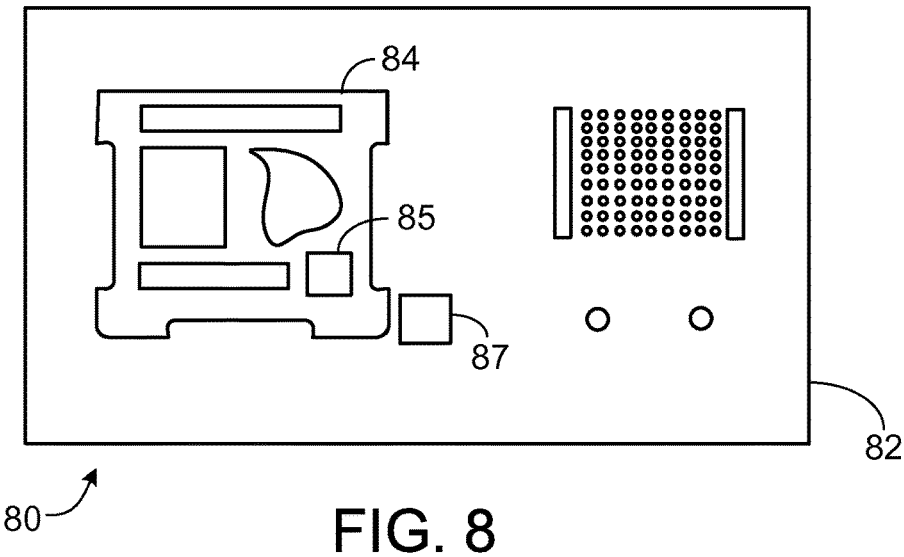
FIG. 8 shows a badge in a badge holder.

Instead of integrating the badge, sensor, and indicators in one unit, the badge could be an already existing badge of the kind used in hospitals, for example, to identify employees. Such badges often include names, photographs, and magnetic stripes or bar codes that can be swiped on readers. A shown in FIG. 8, the device 80 could take the form of a holder 82 in which the existing badge 84 could be held. The device would then contain all of the other elements except those that appear on the badge. Arranging for a separate badge and badge holder has a number of advantages. The badge can be removed and used and swiped independently of the device. The badge can be replaced separately without requiring a replacement of the device electronics. Existing badge equipment and technology can continue to be used. In some examples, the badge could be designed to couple electronically to the holder using, for example, RFID technology with an RFID element 85 in the badge and an RFID transceiver 87 in the holder. When the badge is placed in the holder, the holder recognizes the identification of the user and other information.

In some examples, the badge, the holder, and the RFID transceiver 87 could be arranged differently. For example, the RFID transceiver could be located on a different device worn by the user while the badge could remain mounted on the holder.

The badge could be powered by photovoltaic cells using ambient light instead of a battery.

Although two different lights could be used to indicate the disinfected and not disinfected conditions, a single light that can change color could also be used, saving cost and space.

Because the ethanol sensor has a lifetime that is limited by the number of test cycles, the badge can include a circuit that counts the number of tests performed and illuminates a warning light or provides some other indicator when the sensor is reaching the end of its useful life.

Other types of ethanol sensors can be used. One such sensor comprises a ceramic chip but is considerably more expensive than the sensors described earlier.

Although ethanol and an ethanol sensor form the basis of some of the examples described here, other disinfectants (for example, trichlosan) may also be used provided that effective sensors are available for them.

In general, in addition to triggering a change in state of the badge after a period elapses, it is also useful to maintain a count of the number of times a person has run a test (sometimes called the number of taps) using the sensor in a given period of time. The badge can contain a counter that keeps track of the number of taps and determines the count per 24 hours. This number can then be reported to the person's employer or to regulatory agencies as evidence of good cleanliness practices in an institution. For reporting purposes, the number of counts can be communicated to a reader by RFID technology, or any other communication technique.

The sensor and indicators need not be associated with identification information but could be provided in a device the sole purpose of which is to measure the concentration and provide an indication of it.

The device can be used in non-health care environments in which hand cleanliness is important or expected.

In a health-care environment, the device could be used by anyone who is providing services as well as by patients and their families or friends.

Information about the frequency, timing, and results of measurements performed historically by the user can be stored on the badge.

Many additional functions could be added to the badge by increasing the capacity of its processor, memory, displaying, communications ability, and user inputs features.

In other examples of a cleanliness sensing badge 200, as shown in FIGS. 10, 11, 12, 13, and 14, a battery 202, a circuit board 204, a sensor 206, a multi-color LED 207, a two-dimensional display 209, and a momentary on switch 208 are mounted within two halves 210, 212 of a housing. To reduce the chance of contamination of or damage to the components on the inside of the housing, sealing elements can be provided along the seam between the two halves and at the openings in the two halves through which each of the LED, the switch, and the display are mounted.

Figure 14:
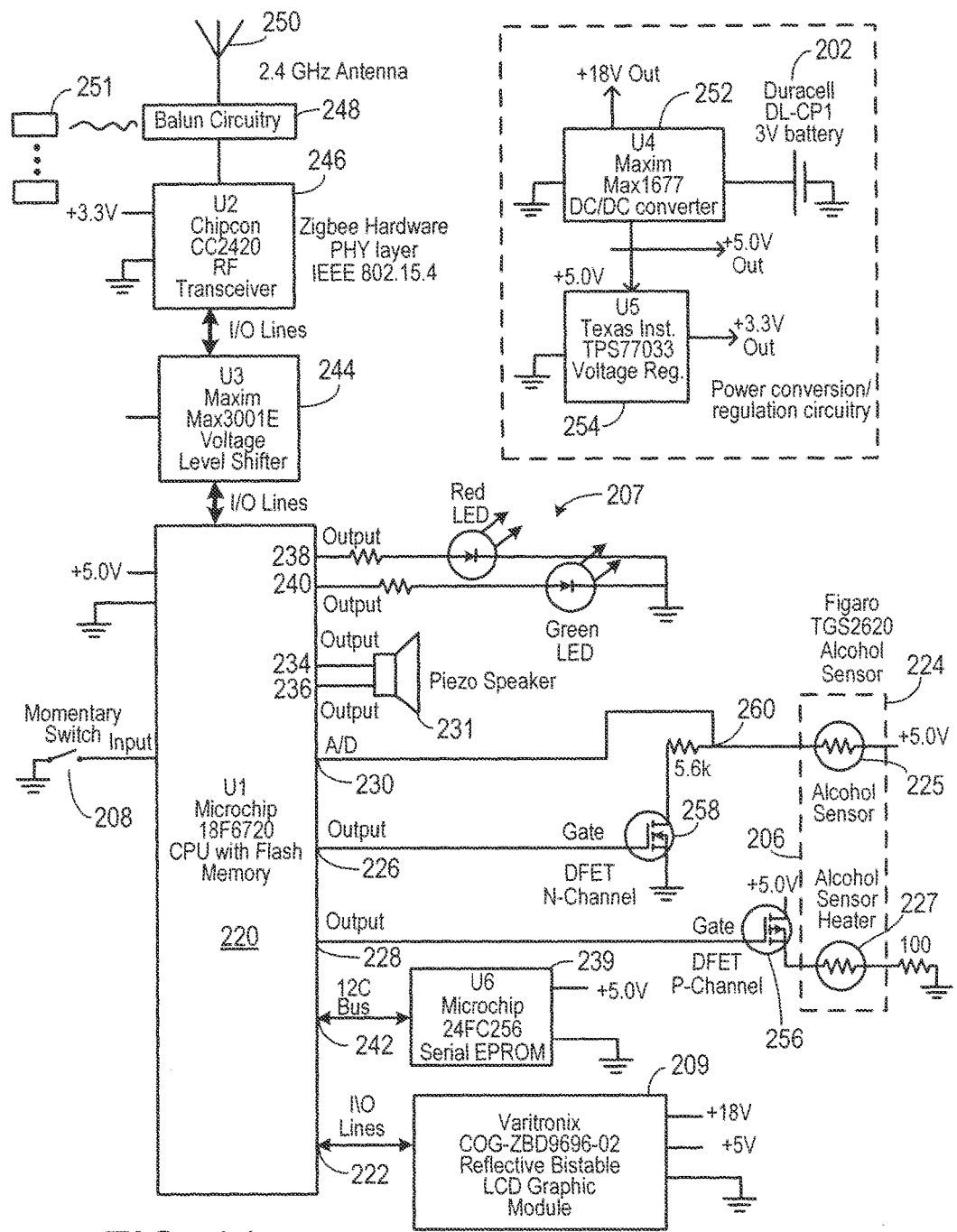
FIG. 14 is a schematic diagram of a badge.

As shown in FIG. 14, the components of the sensing badge include a CPU 220 having a flash memory (Microchip part 18F6720) to control (a) the display 209 (Varitronix part COG-ZBD9696-02) through I/O lines 222, (b) an alcohol sensor 224 (Figaro part TGS2620) through control outputs 226, 228, and A/D input 230, (c) a piezo speaker 231 through outputs 234, 236, (d) the two-color LED 207 through outputs 238, 240, and (e) an external EPROM (Microchip part 24FC256) 239 through an I/O bus 242. The CPU 220 also receives information from the switch 208 and communicates bidirectionally through a voltage level shifter 244 (Maxim part Max3001E), an RF transceiver 246 (Chipcon part CC2420), a balun circuit 248, and an antenna 250 with transponders, base stations, and possibly other external devices 251. The voltage level shifter shifts the DC voltage level of signals sent back and forth to the CPU from the 5.0 volts level used by the CPU to the 3.3 volts level used by the transceiver, saving power.

Power for the circuitry is provided by the battery 202 through a DC/DC converter 252 (Maxim part Max1677) and a voltage regulator 254 (Texas Instruments part TPS77033).

The alcohol sensor 224 includes a sensor element 225 and a heater 227. The resistance of the sensor element changes in the presence of alcohol vapor by an amount that relates to the concentration of the vapor. By permitting alcohol vapor from a person's finger to reach the sensor and by using an appropriate test protocol, the relationship of the concentration of the vapor to a threshold can be determined and used to establish a disinfected or not disinfected state of a user's hands. The resistance of the sensor element 225 is measured as an analog voltage at the A/D input of the CPU. If the sensor element remains dry, the resistance of the element in the absence of alcohol will be subject to very little drift. However, if the sensor element is exposed to water or water vapor, the resistance will change substantially. For this reason, in a typical use of the sensor element 225, the heater is energized for a period to dry the sensor element before a measurement is taken. Thus, a time delay must occur from the time when a measurement is desired until the time when the measurement is completed.

To eliminate the time required to heat the sensor element at the time when a test is to be started, the resistance of the sensor element is continually monitored. If the drift in the resistance of the element occurs more slowly than a background drift rate, indicating that the sensor element has remained dry, no action is taken and the sensor element is considered to be in a standby mode. Conversely, if the resistance drift is comparable to what would be expected when water vapor is present at the sensor element, the CPU drives the heater in a heating mode to dry out the sensor element. As soon as the resistance has returned to the expected dry value, the heater is turned off and the system returns to the standby mode.

When the sensor element is in the presence of alcohol vapor, such as when a person with disinfected hands places a finger near the monitor, the resistance of the dry sensor element shifts substantially, indicating a presence of alcohol vapor. This causes the CPU to enter a test mode in which a determination is made whether the concentration of the vapor exceeds a threshold that indicates disinfected hands. Once the test is completed and related actions are taken by the CPU in response to the result, the CPU returns to the dry mode. The heater is driven by the CPU output through the gate of a transistor 256. To detect the resistance of the sensor element, the CPU drives the sensor element through the gate of a transistor 258 and the voltage level at a node 260 is the analog input to the CPU.

In this way, the sensor is always available for a test measurement without requiring a heating cycle and the user can perform a test simply by putting her finger near the sensor element without requiring an on switch to be activated. Nevertheless, in some implementations, a switch can be provided that can be pressed by the user to initiate the test mode.

The program used by the CPU to operate in the standby mode, the heating mode, and the test mode, is stored in the CPUs flash memory, while data needed to operate in those modes, data derived from measurements of the resistance of the sensor element, and other information can reside in RAM or external non-volatile EPROM.

The data can be stored in and retrieved from the EPROM by the CPU on behalf of itself and on behalf of external transponders, base stations, and other devices for a wide variety of purposes. Data can be stored at the time of manufacture, at the time of registration of a user, during operation of the monitor, or at any later time.

The data in the EPROM can include calibration information about the empirical relationship of the resistance of the sensor element to the presence of different concentrations of water vapor, and of different concentrations of alcohol.

The data contained in the EPROM includes calibration data, threshold values, and other data useful in the operation of the alcohol sensor, data about a user of the badge, data used for the LCD display, data to drive the piezo speaker, data derived from measurements of the sensor resistance, historical data about the times and results of measurements, and information useful in communicating with external devices.

The calibration data for the alcohol sensor can include empirical data or tables that represent the expected resistance of the sensor element associated with various levels of water vapor or alcohol. The threshold values could include a threshold value for resistance that indicates the presence of water vapor, a threshold value that indicates the presence of alcohol vapor, and a threshold value that indicates that the concentration of alcohol vapor exceeds a value associated with disinfected hands. The data for the alcohol sensor can also include information about rates of change of resistance that may be associated with the introduction of water vapor or the introduction of alcohol vapor that will enable the CPU to determine when to switch modes among the standby mode, the heating mode, and the testing mode. The data stored in the EPROM may also include drift information that indicates an expected rate of drift of the resistance during standby mode over time, and expected rates of change of resistance when water vapor and alcohol vapor are present. The sensor element has a useful life that may be associated with the number of testing cycles for which it has been used. The EPROM may store information about the number of expected cycles and a counter that indicates the number of actual cycles.

During operation, data may be stored in the EPROM that includes a record for each test performed, including the starting and ending time, the starting resistance, the ending resistance, an indication of the result of the test (not disinfected, disinfected, inconclusive), whether the test result has been reported to an external device, and whether the test was initiated by pushing the on button or simply by touching the finger to the badge. The EPROM may also include data useful in perform a diagnostic test of the sensor element by applying a certain voltage and calculating the resulting resistance values over time.

The algorithm that is stored in the EPROM and run by the CPU with respect to the sensor element could include the following sequences. During initialization of the badge (e.g., when the badge is first powered up), the sensor heater may be powered up to heat the sensor element. Then the sensor element may be energized to +5 Volts and the voltage at the A/D input can be read by the CPU. The heater may be kept on until the voltage measurement from the sensor element becomes stable (slope is essentially flat), indicating that the heating mode is done, the sensor element is active and dry, and the badge may enter the standby mode. The heater and sensor element are then de-energized and the sensor element is allowed to cool to ambient temperature. Then the heater and sensor element are re-energized for a calibration test. After a predetermined test period has elapsed (say, two seconds), the voltage from the sensor element is measured and the value is saved as the calibration reference value indicative of the baseline dry state.

When the on button is pressed, the CPU energizes the heater and sensor element for a fixed test cycle period (say two seconds). If the measured voltage representing the resistance of the sensor element is a certain percentage (say 20%) higher than the baseline dry state reference value, the CPU determines the presence of enough alcohol to indicate disinfection. Otherwise the CPU determines no disinfection. In some examples, instead of de-energizing the alcohol sensor after the initial calibration, the CPU may power the sensor element continuously (or frequently but intermittently) and make continuous (or intermittent) measurements of resistance. As an alternative to pushing the on button, when a sharp shift in resistance is detected, the CPU may assume that the user has placed her finger near the sensor element and wants to initiate a test. In addition, if the resistance level changes sufficiently to indicate presence of water vapor, the CPU can initiate a heating mode.

To compensate for drift in the sensor, the CPU may periodically measure the voltage output from the sensor element using the steps described for a button press above. If the measurement reflects only a modest drift in the sensor resistance, then the CPU would substitute the current measurement for the previously stored one. If the drift were significant (perhaps more than one percent different from the previous measurement), the CPU would enter a recalibration mode using the steps described for the initial startup.

In addition to running the algorithm that controls calibration, heating, testing, and standby modes, the CPU may run a process, stored in the flash memory of the CPU, that controls communication of the badge with external devices.

The communication process may perform a wide variety of functions that are initiated either by the CPU itself or by the external device.

In one function of the communication process, the CPU continually watches for a signal from the transceiver indicating that the badge is within communication range of an external device, such as a transponder, a base station, or another device. If so, the CPU may execute a routine to fetch data from the EPROM and communicate it to the external device. The information to be fetched could include the identity of the user of the badge, the results of calibrations of the sensor, calibration values, battery life information, the number of tests performed since the prior upload, and the results of all of the tests performed in the interim, including all or selected portions of the data stored. As explained below, the CPU may have stored data in the EPROM indicating the successive locations in a building or a campus at which the badge had been recognized by external communicating devices, and the upload of data could include the data represent the successive locations. When a test has been performed at one of the locations, the association of the location with the test may also be uploaded.

The determination of what data is to be uploaded could be made by the CPU or by the external device to which the data is to be uploaded.

In addition to uploading data from the badge to the external device, in some examples, information and commands may also be downloaded from the external device to the badge. The data to be downloaded could include updated calibration values, updated threshold values, updated identifiers, information to be shown on the display of the badge, a refresh of prior test results and data, and other information. The commands could include instructions to turn the badge on, or off, to perform a test and return the results, to upload the test results from previous tests, to purge the EPROM of prior test results, to control the lighting of the LEDs or the information shown on the display, to trigger the speaker, to reconfigure the transceiver, to reboot the CPU, and other commands.

The CPU may continually maintain information about the cleanliness state of the user that is based on current and historical tests performed either on the badge or on another device (for example, the results of alcohol tests performed on a wall mounted tester could be communicated to the badge and used for that purpose). The badge will switch from the disinfected state to the non-disinfected state after a predetermined period that can be stored in the EPROM and updated based on empirical data about the duration of effectiveness of an alcohol cleaning of the hands.

In addition, the badge can be forced by a command from an external device to switch from a disinfected state to a not disinfected state when the badge is in communicating range of the external device. This feature can be used by a manager of a building, a space, or a campus, to enforce a fresh hand cleaning regimen on users at certain locations whether or not they are currently in a disinfected state.

For this purpose, external devices may be located in places where the hand cleaning regimen is to be enforced and may continually broadcast state changing commands to any badges that come within range. For example, a transponder may broadcast a "switch to not disinfected state" command constantly or at times when a badge is detected nearby. In response to receiving the command, the badge will switch states and accordingly, update whatever warning signals correspond to a disinfected state may be sent, including switching the LED from green to red, changing a message that is shown on the LCD display, and changing the sound delivered by the speaker. The change in state will strongly encourage the badge owner to wash his hands and test them in order to switch the state back to disinfected.

For example, the manager of a facility may want to enforce the cleanliness regimen at all bathrooms in the facility. External devices such as transponders can be posted at the entrances to all bathrooms (or to clean rooms in the facility, or to operating rooms), causing the badge of every person who enters the bathroom to be switched to a not disinfected state. In order to switch the badge back to disinfected, the user must wash with alcohol and successfully test her finger. The enforced regimen can be managed statically, simply by the placement of the transponders in desired locations that automatically broadcast state-switching commands. In some examples, the control of the regimen could be dynamically altered, if the external devices that cause the switching of the state are in communication with a central controller, for example, through an IP network. In such a system, the central controller could be configured at one time to cause certain selected transponders to flip states of badges and at another time to cause a different set of selected transponders to flip states of badges.

For example, a hospital administrator may wish to enforce the cleaning regimen in one wing of the hospital on one day and in another wing on another day. Or the regimen may be enforced during a night shift but not during a day shift. In some examples, the facility may decide to flip the states of all badges at all locations at one time.

The external devices may include stand alone devices such as transponders that are passive one-way transmitters of commands, do not receive any data in return and are not connected to any other devices. In some examples, the external devices could also have two-way data communications capabilities and/or could be connected to other devices that have additional capabilities. The external devices could be dedicated to functions associated with the badges or could be devices that have other functions for other purposes.

The external devices could include several kinds in one system including transponder, wall-mounted test devices, base stations that would serve multiple transponders, and central stations that would communicate multiple based stations and/or transponders. The communications among transponders, monitors, base stations, and central stations can occur wirelessly or by wired connections and by peer to peer communication or in a client server mode.

In addition to triggering state switches in the badges and communicating data about alcohol tests performed in the badges, the monitoring system can also track the locations and succession of locations of badge holders. In some examples, when badges communicate their identifier information to external devices the information is passed to a base station and/or to a central station. In this way, the central station can be aware of recent locations and the history of locations of all badge holders. The cleanliness state of the badge holders can then be associated with the locations and action can be taken if necessary. For example, if a badge holder repeatedly enters bathrooms in the course of a day but never washes, the administrator of the facility can confront the person directly. More generally, the badge state history of individuals or groups, or all badge holders can be stored and reported, and analyzed.

Studies of selected groups may be performed. For example, a study can focus on the cleanliness habits of surgeons as compared to nurses. For this purpose the party performing the study can control the flipping of states of the badges and record and study information about testing done by the badge holders over time.

The history of which badge holders were in which locations and in what cleanliness states when at those locations may be tracked and analyzed and be used to provide useful information associated with specific events. For example, suppose a patient or other person in a hospital contracts an infection that is normally thought to be transmitted by touching or close proximity. If the patient's room was a location protected, for example, by a state-switching transponder, the history of badge locations could indicate which health care workers were in proximity of the patient during a period considered to be when the infection was transmitted. This could enable identifying individuals who may be carriers of infection for corrective action, for example. Correlation of infections contracted by multiple patients with cleanliness states and locations of badge holders could facilitate identifying a carrier.

To control the operation of the monitor system, each base station and/or each central station can include a graphical user interface, for example, an interface presented in an Internet browser window.

Referring again to FIG. 14, the LCD display 209 can be of a kind that provides a stable display even when unpowered. In such a display, power is required to change the states of the pixels of the display, but once the pixels have reached a stable state, they will remain in that state even after the power has been removed. Such displays are available in as two-state "black and white" devices, and it is expected that gray scale and color LCD panels with the same unpowered stable state feature will soon be available. One advantage of such a display is that the social pressure aspect of the system can be brought to bear even if the user attempts to remove the battery or otherwise disable the device. Such a display also reduces the use of battery power significantly. Other features described here (for example, the use of a lower powered 3.3 volt transceiver and the ability to operate in a standby mode) also contribute to reduced battery load.

The information to be shown on the display could include the name, identifying number, and picture of the user of the badge (based on a stored image), the cleanliness state of the user, the history of the cleanliness state, and the state of the badge and its operation. The displayed information could be controlled by the CPU or in part by the user of the badge, or by the facilities manager.

The communication protocol in some examples is the Zigbee protocol (IEEE 802.15.4) which requires relatively low power, operates at 2.4 Gigahertz, is license-free, and operates at relatively low telemetry rates.

Referring again to FIGS. 10 through 13, the front of the badge includes a sensor access grid 300 in the form of a round configuration of linear slits that allow alcohol vapors to pass into an enclosed sensor chamber 302 formed within the housing. The sensor chamber includes a tubular channel 304 in which the cylindrical outer wall of the alcohol sensor can be held with the end face of the sensor aimed in a direction parallel to the front surface of the badge (rather than aimed in the direction of the sensor access grid). Alcohol vapors can follow the path of arrow 306 into the chamber 302 where it can touch the sensor element face of the sensor. Eventually the incoming vapor can exit at right angles through a vapor exhaust vent 308 on the back half of the housing. The intake grid and the exhaust vent are positioned and oriented so that foreign materials (water or other liquids, for example) that strike the outer faces of the housing cannot easily reach the surface of and contaminate the sensor element. Other features of the housing seal the perimeters of the two halves and the holes through which the on switch, the display, and the LED project.

In some examples, instead of (or in addition to) storing the user's identity information in the EPROM of the badge, the information (and other information about the user) can be derived using RFID technology from an RFID chip 318 that is part of an existing identification badge 316 issued by the facility to the user for other purposes. In these examples, the badge could be extended 314 at one end to accommodate the badge.

The piezo speaker can be used for a wide variety of functions. One function is to provide an audible indication of a cleanliness state of the user. By storing appropriate audio clips in the EPROM and playing them back through the speaker, a happy or upbeat sound could be played briefly when a successful test is completed and an unhappy or grumpy sound could be played when a test has failed. In the case of a failed test, the grumpy sound could be repeated at intervals (say several minutes) and the volume of the sound could be increased and the intervals decreased over time so that the social pressure to wash the hands and conduct a successful test becomes irresistible.

In addition to a display, an LED, and a speaker, the badge could include a vibration element to alert the user when the safe disinfected period is near an end or has ended, for example.

Figure 6:
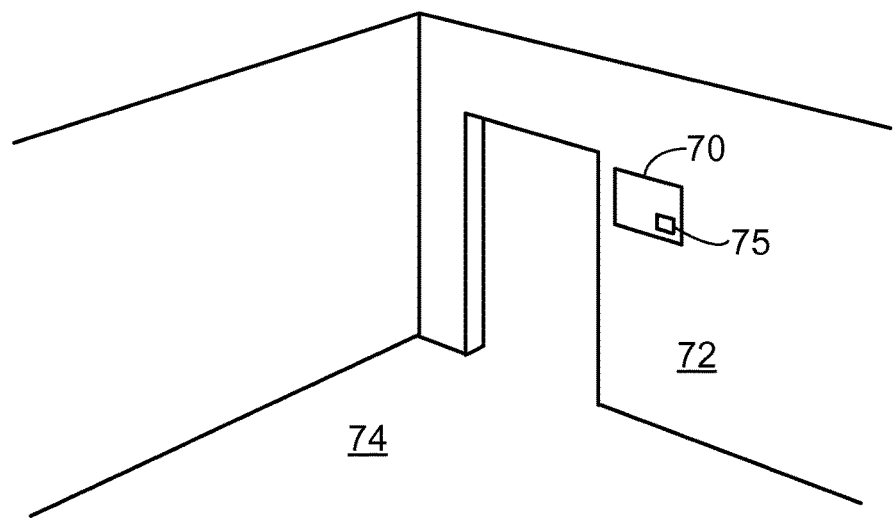
FIG. 6 is a three-dimensional view of a space.

As shown in FIG. 6, in some examples, a monitor 70 could be mounted on a wall 72 of a space 74, such as a bathroom. The monitor could contain a radio frequency transceiver 75 that would cooperate with radio frequency identification (RFID) elements contained in badges of users. Using RFID technology, when a person wearing a badge passes near to the monitor, the monitor could use RF communication to determine that the person is present and to fetch information from the badge about the person's identity (and other information as discussed later). The monitor could also send an instruction to the badge to cause the badge to reset itself to the not disinfected state. Communication technologies other than RFID could also be used to detect the presence of the user and to communicate information between the monitor and the badge or other elements worn by the user. The element worn by the user could be one that identifies the user or one that does not identify the user.

When the person wearing the badge enters the bathroom, or any other monitored space such as a patient room, or a surgical theater, the triggering device sends a signal to the badge that causes the badge to enter the not disinfected state and light the lamp that indicates that state. This triggering will encourage the user to disinfect his hands before leaving the bathroom or before proceeding further into the monitored space in order to avoid the social disapproval associated with leaving the bathroom with the red light on. In these examples, the badge's state could be forced to change to the not disinfected state regardless of how much time has passed since the most recent successful test using the badge sensor. The user's status can be reset to the disinfected state by the user cleaning his hands and testing them.

Figure 7:
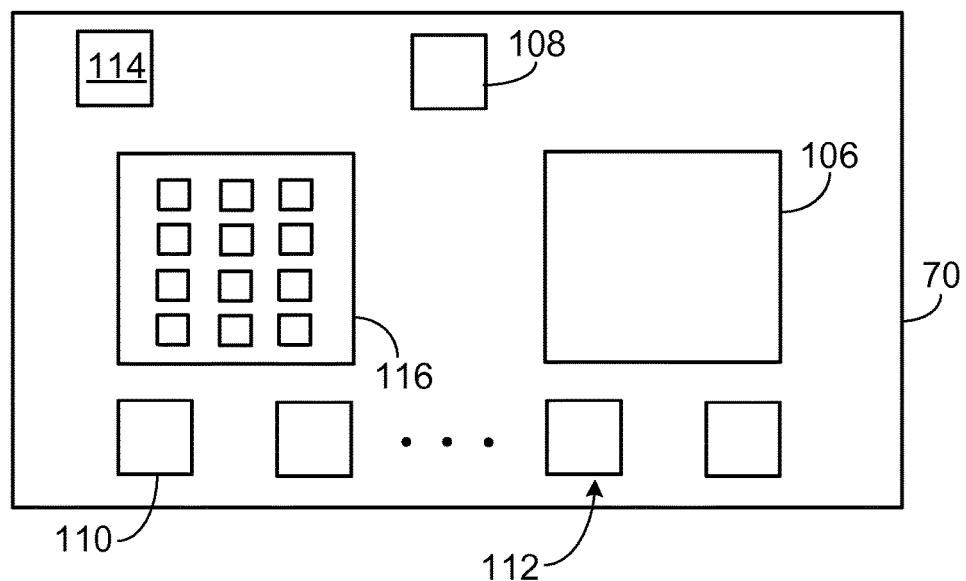
FIG. 7 shows a monitor.

As shown in FIG. 7, a hand cleanliness monitor 70 could include not only an ethanol or other sensor 106 but also a presence detector 108 and one or more indicators 110 of hand cleanliness with respect to one or more people who have entered the space. One of the indicators 112, which could be broadly visible to people in the space (for example, if it is placed on an interior wall of a room) or people outside the space (for example, if it is placed on an interior wall of a room) or both, could turn from green (indicating that all people in the space are believed to have disinfected hands) to red when a person is detected as entering the space. In that case, the red light would indicate to viewers that a person whose hand cleanliness state is unknown and assumed to be not disinfected has entered the space.

The person entering the room could cause the light to turn from red back to green by touching the sensor (assuming his hands bear enough ethanol to imply a disinfected condition) or by first cleaning his hands and then touching the sensor.

In some examples, the monitor could be placed on in interior wall of a patient's room. Whenever anyone enters the room, including health care workers, the patient, or guests, the monitor would indicate a possibly not disinfected condition until someone touches the sensor and causes the red light to turn green. Social pressure of people in the room, who would observe the red light would help to enforce good cleanliness habits on every person entering the room.

The parts of the monitor need not be included in a single integrated wall unit. For example, a portion of the monitor that detects that a person has entered or left a space could be a separate system, including an existing system, that would exchange the information with the monitor as needed. The indicators could also be located separately from the monitor to make the lights visible to many people even though the monitor is located near an entrance to or exit from a monitored space. The sensor, too, could be located separately from the monitor. For example, the badge sensors could provide the re-test information to the monitor.

In some examples, an entire building could be monitored by providing monitors on the walls at all entrances to the building. In addition to the social pressure associated with public display of the not disinfected condition, an employee or automated gate at each entrance could require that the person entering either prove that his hands are disinfected by using the sensor either upon entry or after using a disinfectant available at the entrance.

A variety of spaces could be monitored, including bathrooms (or other locations where disinfecting is especially important) and changing areas in hospitals or food processing facilities, for example.

In some examples, the monitor could include circuitry that would detect, in other ways than described above) a presence of one or more people within a space (whether or not the people have entered or left the space), would determine a cleanliness state of hands of the people detected as present, would include circuitry to report the cleanliness state.

A publicly viewable monitor used to indicate the disinfected condition for people within a space can facilitate social pressure being applied by people in a room to people who enter the room even without the monitor having any information about the identity of a person entering the room. In addition, the monitor may include or be part of a system that includes devices to determine who has entered a space and to correlate that information with a person who then uses the sensor to indicate that his hands have been disinfected.

For example, the person entering the room may carry a badge (of the kind issued by a health care facility) that uniquely identifies him and includes a bar code, a magnetic stripe, an RFID element, or another device that can be read by a reader 114 (for example, the RF transceiver 75 in FIG. 6) that is on the monitor or mounted separately on the wall. Depending on the technology, the user's badge could be read from a distance or be swiped on a reader. When the person enters the room, his presence and identity are detected. At the time when he successfully completes a measurement by the sensor indicating that his hands have been disinfected, his identity is read again and compared with the identities of people who have entered the room and not been determined to have passed a measurement for disinfected hands. Only when all of the people who have entered the room have passed the test will the red light be switched to green.

An enterprise could issue temporary identification cards to every person who enters a building or other space and does not already have an identification badge for use with the system.

A variety of other techniques could be used to identify the person entering a space, including detection of biometric information (such as a voice print or a finger print or a facial print) or requiring a person to enter an identification code on a keypad 116 on the monitor. The person could enter the identification both upon entering the room (in some cases as a trigger for a locked door or other entry gate) and upon passing a disinfection test using the monitor. In some implementations, it may be possible to identify a person using a fingerprint detection technique at the same location on the monitor and at the same time as the disinfection test is performed. Other techniques could also be used to assure that a successful test is accurately correlated to an identifiable person.

The monitor can also include circuitry that keeps track of how many people are in the space (for example, by also detecting when someone has left the space). When the oldest successful disinfection test (among tests that number as many as there are people still in the room) occurred more than a predetermined period (say 2 hours) earlier, the monitor can time out and change the green light to red until someone in the room successfully tests his hands again.

In these examples, and others, it is possible for people to deceive the monitor, for example, by having one person in the room repeatedly test his hands positively on behalf of other people in the room. However, as indicated earlier, at least in some examples, the social pressure associated with the public display of the disinfection state of the space and the shifting of green to red in certain situations, may be sufficient to significantly improve the frequency and quality of hand cleaning among people in the space.

Other arrangements could be used to reduce the degree and nature of the deception that may be possible and to increase the ability of a monitoring system to track and report the performance of identified people or groups of people in maintaining hand cleanliness. Some such arrangements would use the unique identifiers associated with different people to track their performance.

For example, the wall monitor could include a processor and software to track individuals who enter and leave a room based on their unique identifiers and correlate the identities with tests that are performed successfully. The monitor could then control the red light and green light based on the successful testing of hand cleanliness by each individual in the space at least as often as some pre-specified time period (say every two hours). By including a small display 120 on the face of the monitor, the person whose hand cleanliness requires re-testing can be identified by name or identifier or some other indicator. In this way, each of the people in the space can be alerted from time to time of the need to re-clean, and re-test and everyone in the space can know who needs to do so.

Such a monitor could be used in conjunction and cooperation with worn badges, for example, of the kind discussed earlier. For example, using RFID or wireless or other kinds of communication capability in the monitor and at least some badges, the monitor and the badge could communicate, exchange information, control actions, and make reports, all in a wide variety of ways.

In a simple example, the monitor could cause the light on a badge to switch from red to green at the same time (or different times) as the lights are switched on the monitor, to indicate to others in the space which person in the space needs to re-clean and re-test. A successful test performed on the badge can be reported to the monitor for use, for example, in the same way that a test on the monitor would be used. Conversely, the monitor can report to a badge a successful (or unsuccessful test) performed on the monitor by the owner of the badge. More generally, the badges and monitors in one or more spaces can continually be synchronized to store common information about tests by the owner of the badge and to cause common indications of the cleanliness state of the badge owner to be given by both the monitor and the badge.

As a person moves around in a building that has more than one monitored space, the monitors and the badges will together in that way maintain current information and provide current indications of the cleanliness state of the badge owner.

Figure 9:
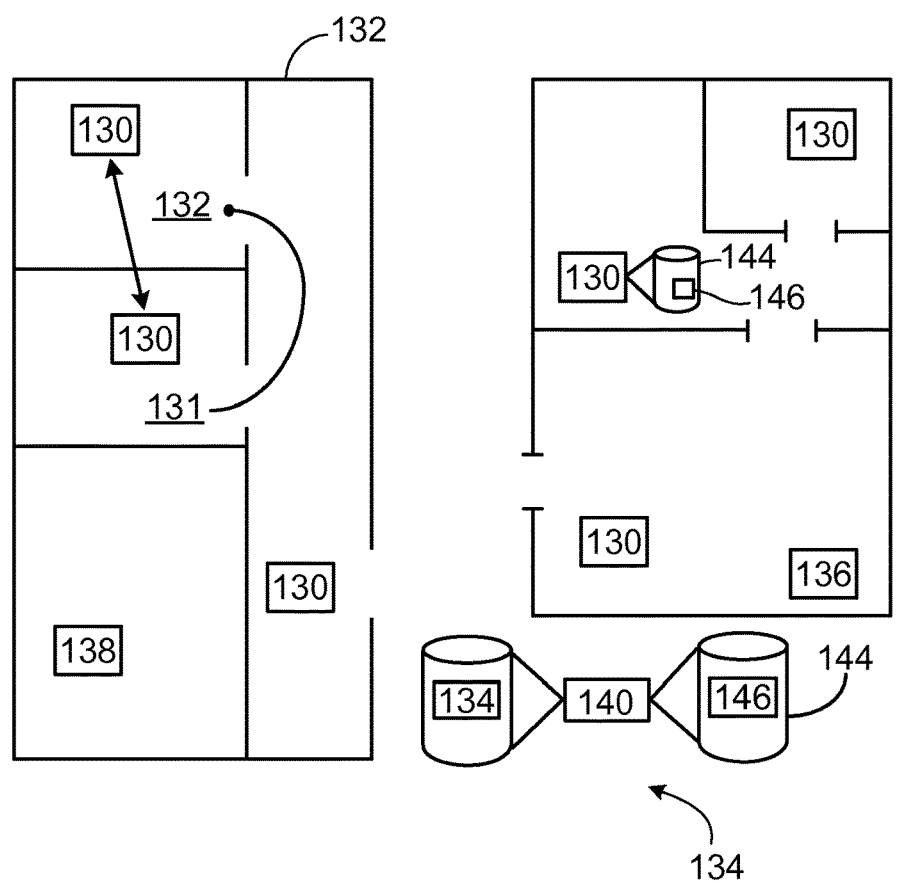
FIG. 9 is a schematic view of a campus of buildings.
Figure 10:
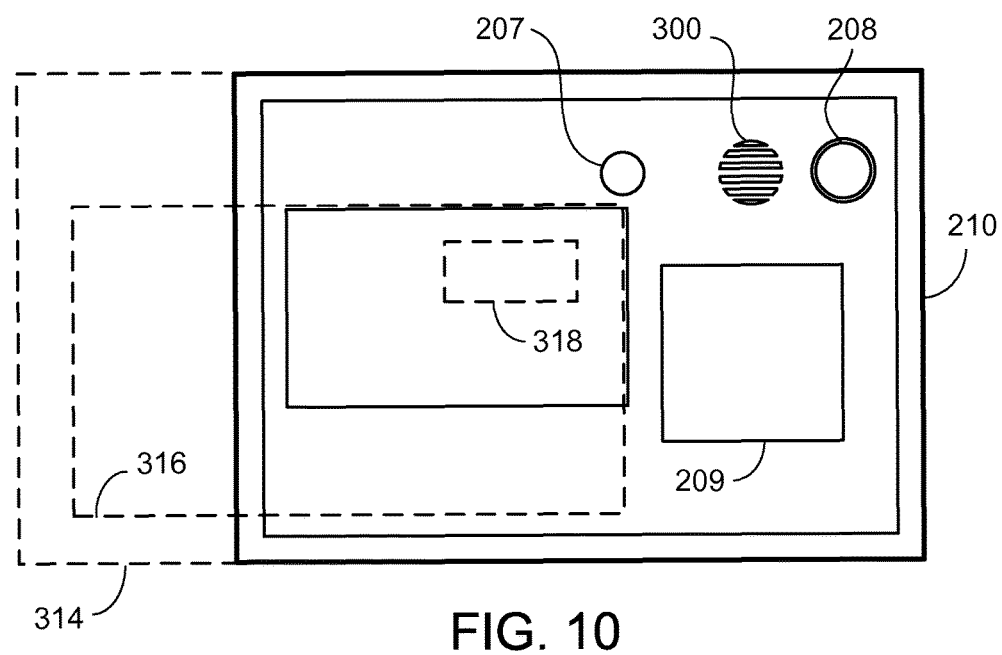
FIGS. 10 through 13 are outside front, inside front, outside back, and inside back views of a badge.
Figure 11:
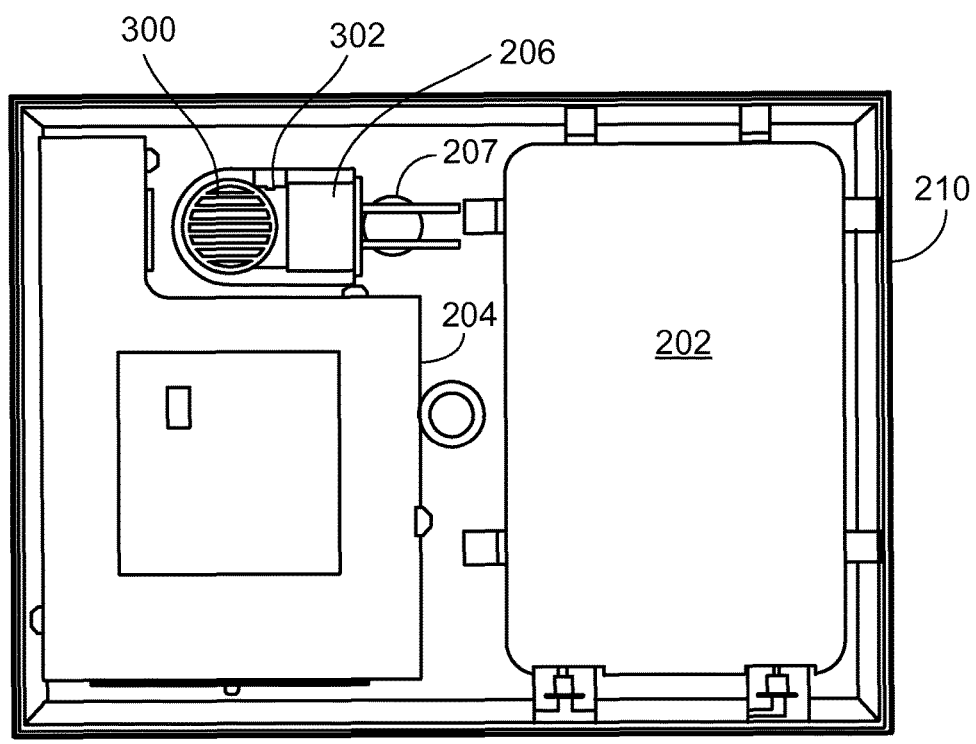
Figure 12:
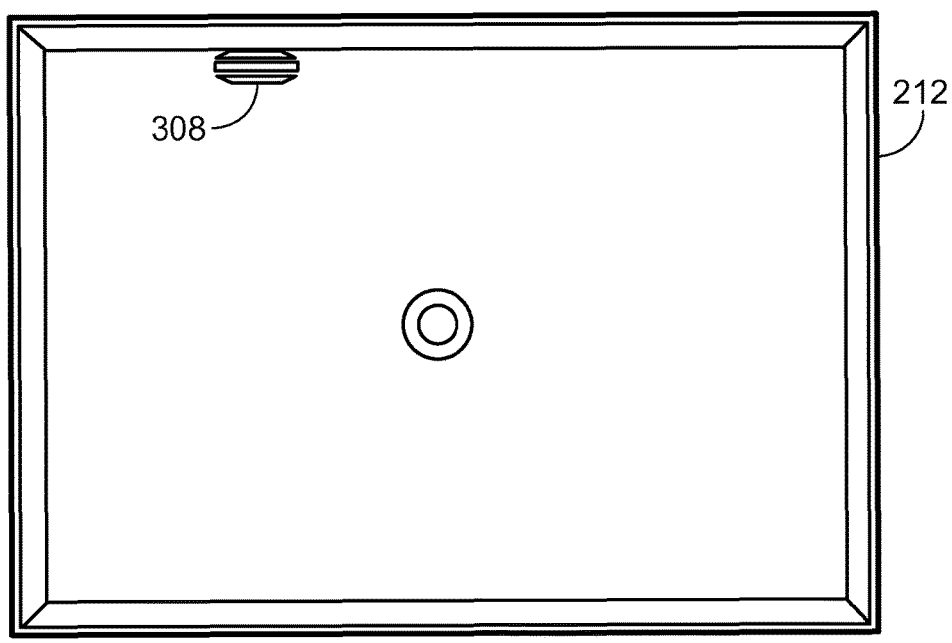
Figure 13:
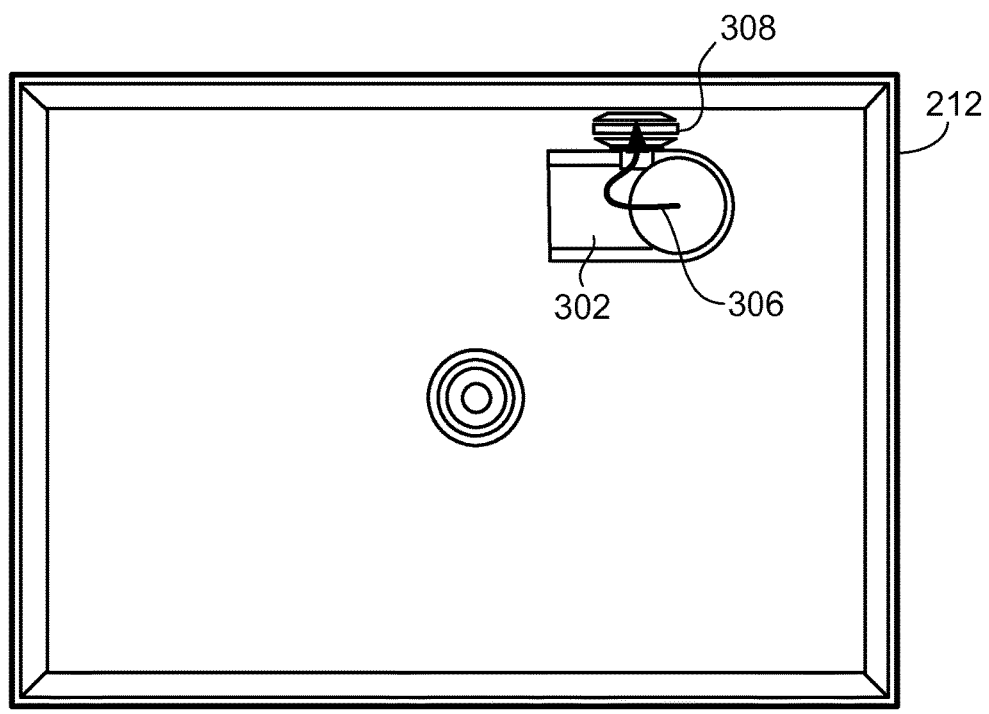

As shown in FIG. 9, although this co-operative maintenance of information and reporting can be done informally and by ad hoc action of different pairs of badges and monitors over time through a building, additional functions and better performance may be achieved by arranging for a portion or all of the monitors 130 in a building 132 or campus of buildings 134 to be interconnected by a wired or wireless communication network on a peer-to-peer basis or with the co-operation or control of a central server 136 or a distributed set of central servers 136, 138, 140. The central server or servers may be servers already used for a facility to provide communication and manage the control of other kinds of devices scattered throughout the facility or the reporting of information from other kinds of devices.

The monitors, the badges, and/or the central server or servers may include memory or mass storage 144 that contains a database 146 or other organized information about the permanently or temporarily registered people who have access to a building or space. The database can store information that is associated with individuals and information that is statistically related to groups and subgroups of the individuals.

In some implementations, an individual badge can maintain a small database of information about a complete history of an individual's cleanliness testing beginning at the time when the badge was first issued, or at some later time. Or a rolling set of data ending at the current time may be kept. The data may catalog every instance when the user tested the cleanliness of his hands, the result, the time of the test, and the parameter values that were produced by the sensor in the testing. When the badge is able to communicate with monitors in different spaces or subspaces, the badge database may also track the places in which each of the tests was performed, which other people were present in the space when the tests were performed, and other information. Information in the badge database can be uploaded to one or more monitors using the communication links to the monitors, or may be uploaded from the badges directly to a central server using special badge readers located in one or more places in the facility.

Each monitor can maintain a database of information using information from badges of people with whom the monitor has interacted and information from other monitors in other spaces (for example, contiguous spaces). The database of a monitor could track every time a person has entered a monitored space and every time she has left the space. The data could include the time of entry, the time of exit, the space in which the user was most recently monitored, the time between entry into the space and when a re-test was performed, the results of the re-test, the number of re-tests performed in the room, the identities of other people in the room at the time of re-test, and a wide variety of other information.

If a person leaves a monitored space 131 and enters a monitored space 132, the monitors in the two spaces could be arranged to communicate so that the monitor in space 132 need not require a re-test if a re-test had been done in space 131 within a pre-specified earlier period.

When the monitors and/or badges are networked with a central server, the central server can use information provided from the monitors and/or badges to track the overall cleanliness testing activity of all of the monitored people in all spaces that are networked.

The central server could maintain a database 134 that could include detailed historical information and statistical summaries of information. The information could track every time any of the monitored people enters or leaves a monitored space, the number of times and the times at which re-testing has been done, the results of each re-test, the routes of the people moving through the building or campus, whether the people are wearing their badges, whether they used their badges or the wall monitors to re-test cleanliness, and a wide variety of other information.

The central server can use software 140 running on the server or servers to analyze information stored in the central database or the databases of one or more of the badges or the monitors. The analyses can address the performance of different groups on cleanliness, the correlation of cleanliness to location, the correlation of demographics (age, gender, geographic location) with cleanliness, the impact of training, monitoring, and other actions on the cleanliness performance, and time dependent changes by individuals, groups, and subgroups of cleanliness performance.

In addition to monitoring and analyzing information about cleanliness performance the central service can provide reports that are useful to or required by the party that operates the building or campus, other institutions, liability carriers, and governmental bodies that regulate certain aspects of the performance of the party and the individuals employed by the party. For example, governmental agencies may require hospitals to assure that hospital employees are disinfecting their hands more often than a certain number of times a day and to report failures to meet that requirement. Reports may also be given to individuals being monitored to groups of individuals, to their supervisors, and to others. Reporting to individuals can be done by email. For example, a doctor who is not disinfecting his hands often enough would periodically be sent an automatic email urging him to improve his cleanliness practices.

The physical housing used for the monitor could be much smaller than the badge shown in earlier examples and could be used in other environments. For example, a badge in the form of a ring could be used for a nanny. At the end of the day, when the parents of the nanny's charge return home, the ring would immediately indicate whether the nanny had washed her hands at least every two hours during the day. In another example, the printed circuit board used to implement a badge can be a stacked printed circuit board to provide a more compact form.

Figure 15A:
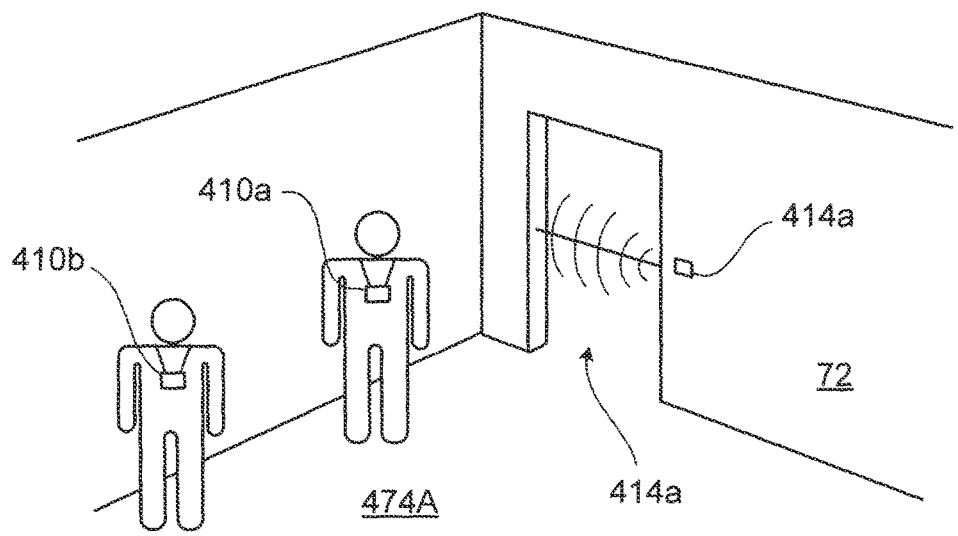
FIGS. 15A and 15B are schematic views of a cleanliness monitoring system.
Figure 15B:
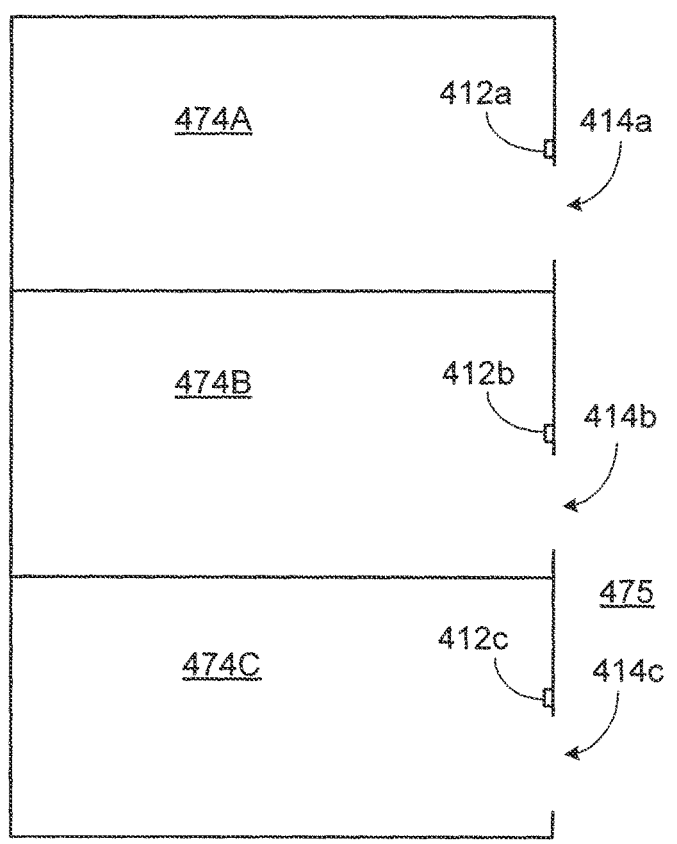

In some implementations as illustrated in FIGS. 15A and 15B, a system 400 including badges 410 and monitors 412 can be configured to prompt individuals (e.g., health-care providers) to sanitize their hands both on entering and exiting a specific space (e.g., a patient's room).

Figure 16A:
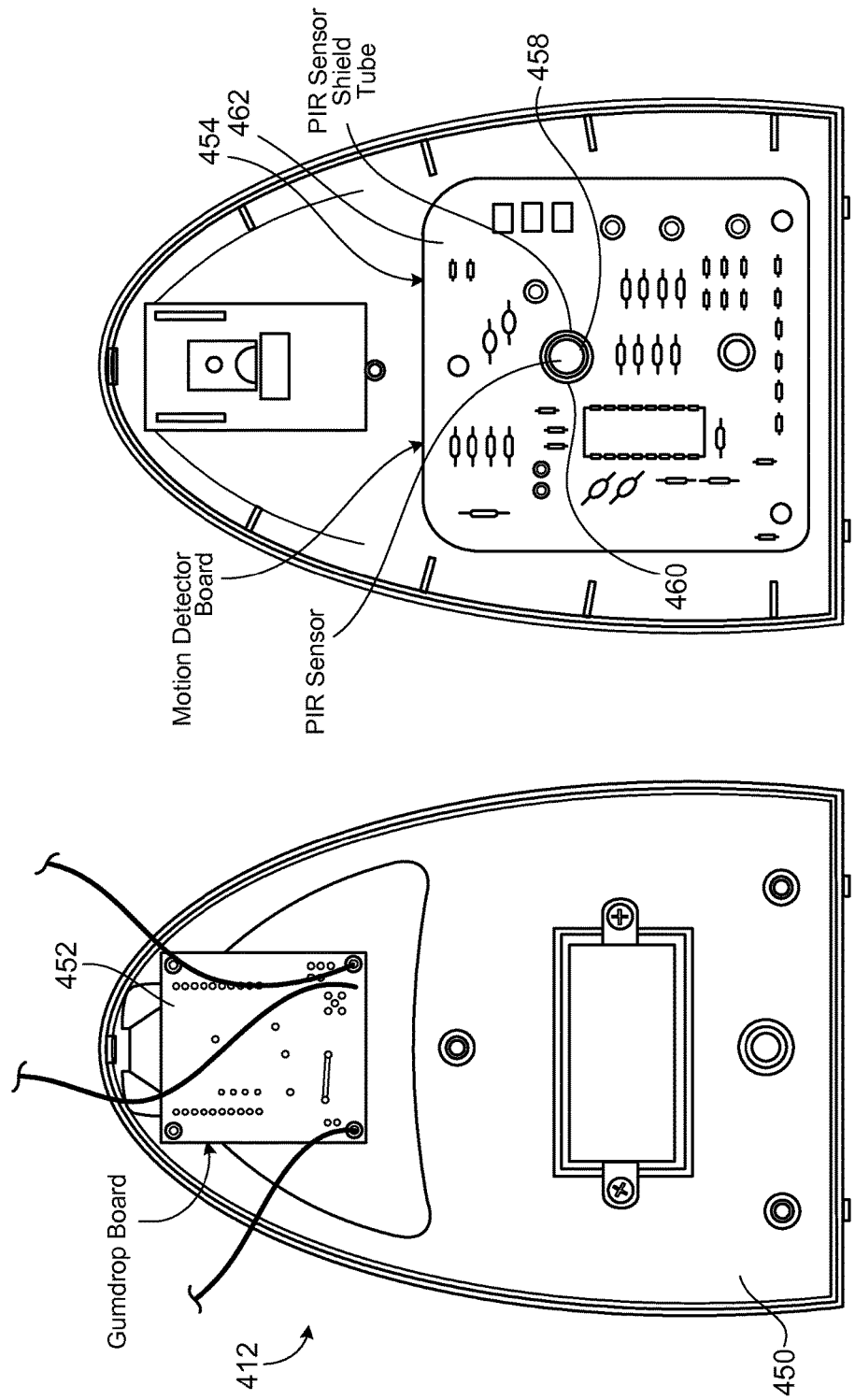
FIGS. 16A and 16B show a monitor.
Figure 16B:
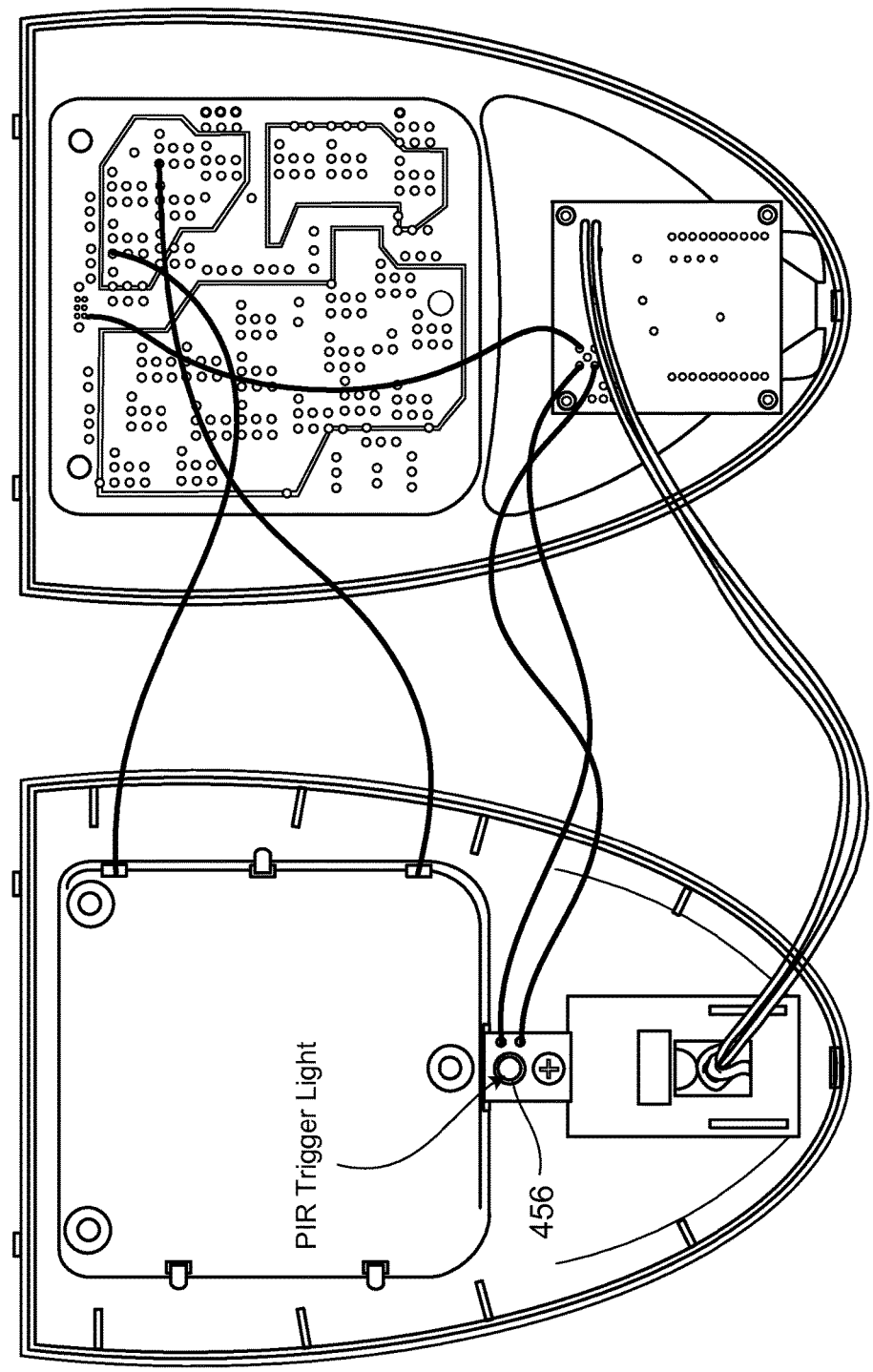

As shown in FIGS. 16A and 16B, each of the monitors 412 can include an outer casing 450. A PLC chip 452, a motion detector 454, and a transceiver 464 are disposed within the outer casing 450. As illustrated, the motion detector 454 can be a programmable infrared detector including an infrared sensor 458 mounted on a motion detector board 462 and a trigger light 456. The trigger light 456 is placed to emit infrared radiation through an opening in the outer casing 450. A sensor shield tube 460 extends from the motion detector board 462 to an opening (e.g., the same opening through which the trigger light 456 emits infrared radiation or another opening). The sensor shield tube 460 can reduce or prevent direct transmission of infrared radiation from the trigger light 456 to the infrared sensor 458. Rather, as a person or object crosses in front of the opening, some of the infrared radiation emitted by the trigger light 456 is reflected by the person or object and travels through the sensor shield tube 460 to contact the infrared sensor 458. In some embodiments, other motion detectors such as, for example, ultrasonic motion detectors can be used. The monitors can be battery-powered, can include photovoltaic cells, can be directly wired into a building's electrical system, and/or can be adapted to be plugged into standard wall sockets.

The motion detector 454 is electronically coupled to the PLC chip 452. Upon receipt of a signal from the motion detector 454 indicating that the infrared sensor 458 has detected infrared radiation, the PLC chip 452 actuates the transceiver 464 to send a signal configured to be received by badges 410. For example, the signal can include information identifying the transmitting monitor 412.

As shown in FIGS. 15A and 15B, the monitors 412 can be located near doorways 414 or other thresholds (between spaces) to be monitored. In response to motion in a doorway 414, the monitor 412 placed near that doorway 414 sends a signal including information identifying the transmitting monitor 412. The monitors 412 are positioned inside the room adjacent to the doorway so that the signal is primarily within the room and is strongest near the doorway 414.

As is discussed in more detail below, each monitor 412 is configured and placed to preferentially interact with badges near the doorway within the room where the monitor 412 is mounted. As part of this configuration, the transmission power levels of the transceiver 464 can be controlled by the PLC chip 452 of the monitor 412. For example, it has been found that monitors 412 mounted about 3-5 feet above the ground with transceivers 464 transmitting at a power level of less than about 1 milliwatts produce a signal of sufficient strength to trigger most or all badges 410 within about 3 feet of the doorway where the monitor 412 is mounted while having sufficient signal loss to have low or no signal transmission outside the room where the monitor is mounted and to have sufficient signal loss that relative signal strength can be used as an indicator of when a badge 410 is passing though the doorway being monitored. In some instances, the monitors can be mounted above the doorway.

In some embodiments, the signal strength can be increased or decreased in order to account for factors such as, for example, larger room or boundary dimensions. For example, the PLC chip can be programmed to actuate the transceiver 464 to transmit with a signal strength of between about 0.25 and 5 milliwatts (e.g., about 0.5 milliwatts, about 0.75 milliwatts, about 1.5 milliwatts, about 2.5 milliwatts).

In the illustrated embodiment, the transceiver 464 transmits on a wavelength of about 2.4 GHz.

Figure 17A:
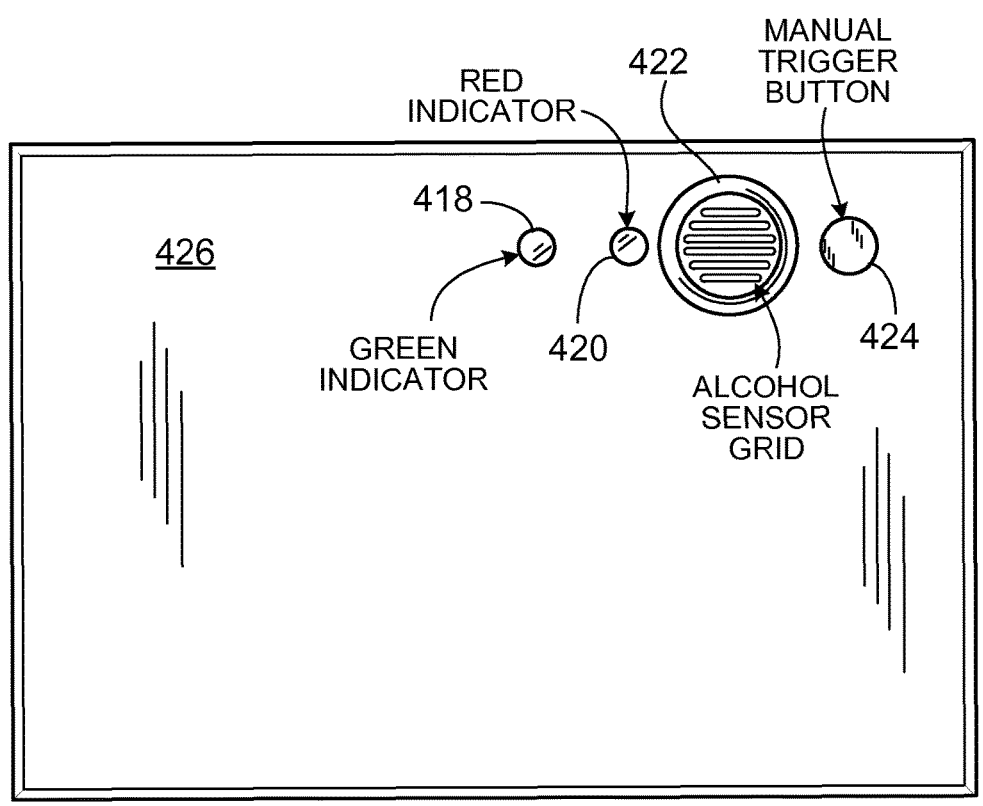
FIGS. 17A-17C show a badge.
Figure 17B:
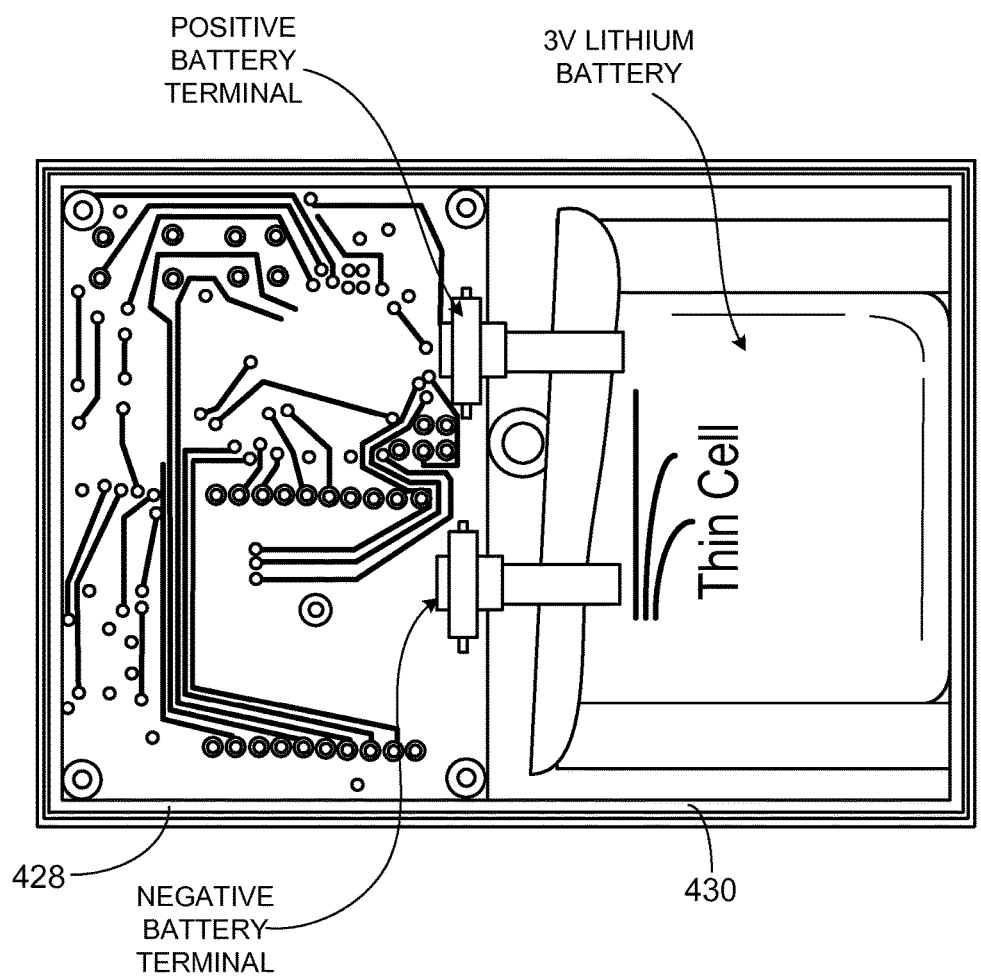
Figure 17C:
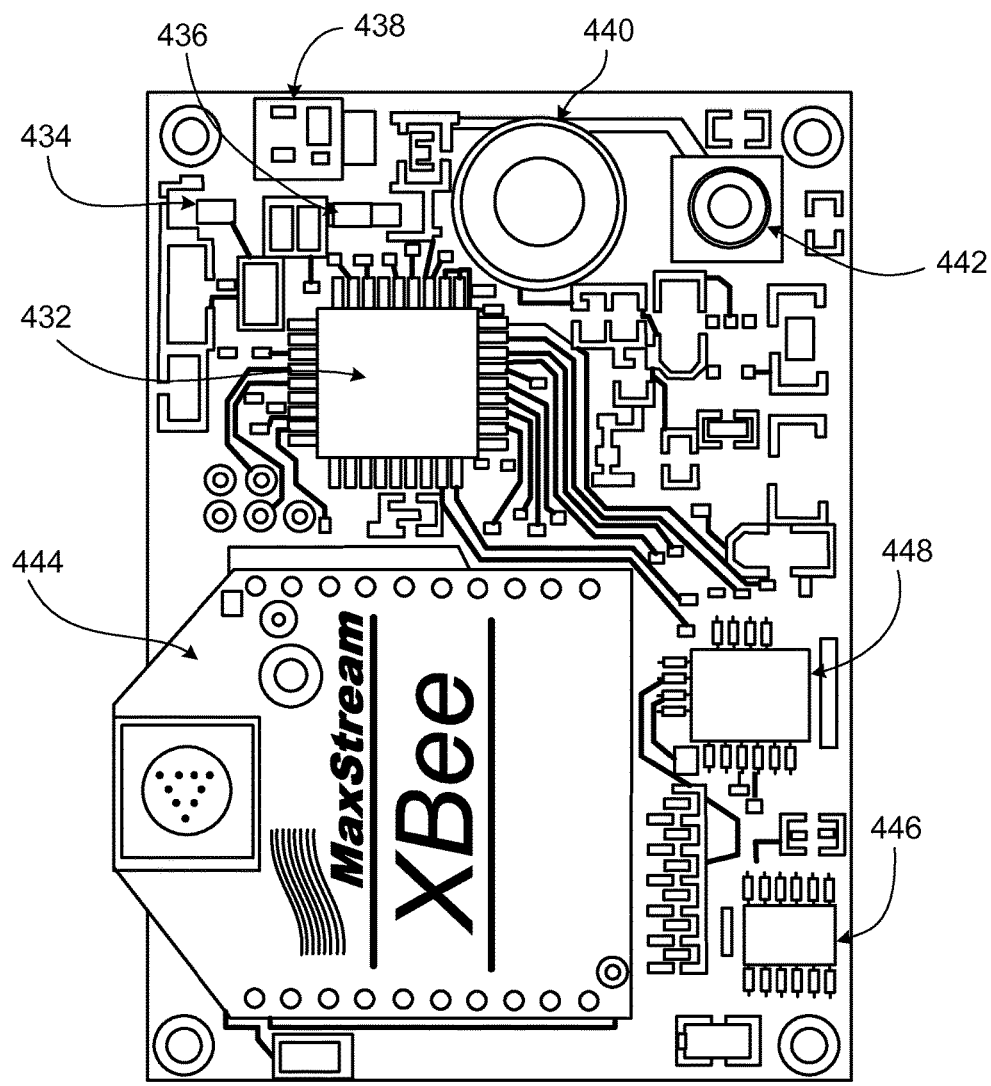

As shown in FIG. 17A, an exemplary badge 410 can include a green indicator 418, a red indicator 420, an alcohol sensor grid 422, and a manual triggering button 424 on its outer casing 426. As shown in FIGS. 17B and 17C, the badge 410 can include a badge board 428 powered by a battery 430 (e.g., a 3V lithium battery), both held within the outer casing 426. The badge board 428 includes a programmable logic controller (PLC) chip 432 coupled to a green LED 434, a red LED 436, a speaker 438, an alcohol sensor 440, and a transponder 444 which function in substantially similar fashion to the corresponding elements of the previously described badge 200. The badge 410 also includes a manual triggering switch 442, a real-time clock 446, and an accelerometer 448 coupled to the PLC chip 432. The manual triggering switch 442 is used to manually trigger a test cycle is as described in more detail below. The real-time clock 446 is used to establish the time at which various log events such as, for example, test cycles occur.

The PLC chip 432 is configured to implement a state-control logic to encourage users to follow proper sanitation protocols. For example, the state-control logic can be configured to activate a hand sanitation check both on entry to and exit from a monitored room. An exemplary state-control logic is described in more detail below.

The badge can have a sanitized state indicated by activation of the green LED 434 and an un-sanitized state indicated by activation of the red LED 436. When the badge is initially activated, the PLC chip 432 sets the badge 410 in its un-sanitized state. When the badge 410 is in an un-sanitized state, the PLC chip 432 activates the red LED 436 and shuts down other components including, for example, the alcohol sensor 440. Pressing the manual triggering button 442 can trigger a cleanliness test cycle. After a successful cleanliness check is performed, the PLC chip 432 sets the badge 410 in its sanitized state. When the badge 410 is in its sanitized state, badge components including the alcohol sensor 440 and the red LED 436 are turned off, the PLC chip 432 is in a listening mode, and the green LED 434 is turned on.

In the embodiment described above, the PLC chip 432 uses the transponder 444 to broadcast its badge identification signal upon receipt of a location signal from a monitor 412. In some embodiments, badges 410 are configured to continually broadcast their badge identification signals or are configured to broadcast their badge identification signals at preset intervals as well as upon receipt of the location signal from a monitor 412.

The battery 430 powering the badge 410 can be a disposable battery or a rechargeable battery. In the illustrated embodiment, the battery 430 is disposable battery. In some embodiments, the badge 410 can be stored in a charger when not in use to recharge the battery 430. In some embodiments, the badge 410 includes photovoltaic cells instead of or in addition to the battery 430. For example, the badge 410 can be configured to operate using photovoltaic cells for power when sufficient ambient light is available and the battery 430 as a supplementary or replacement power source when the photovoltaic cells do not provide enough power.

The accelerometer 448 (e.g., a three-axis accelerometer such the MMA7260Q Three Axis Low-g Micromachined Accelerometer commercially available from Freescale Semiconductor of Chandler, Ariz.) sends a signal to the PLC chip 432 indicating whether the badge 410 is in motion. The PLC chip 432 can be programmed to shut down the badge components after a set period of time (e.g., 10 minutes, 20 minutes, 30 minutes, or 60 minutes,) passes without the accelerometer 448 indicating that the badge 410 is in motion. For example, if the badge 410 is stored in a physician's desk when she leaves the hospital, the badge 410 will shut down to conserve the battery 430 after the set period of time passes.

Figure 18:
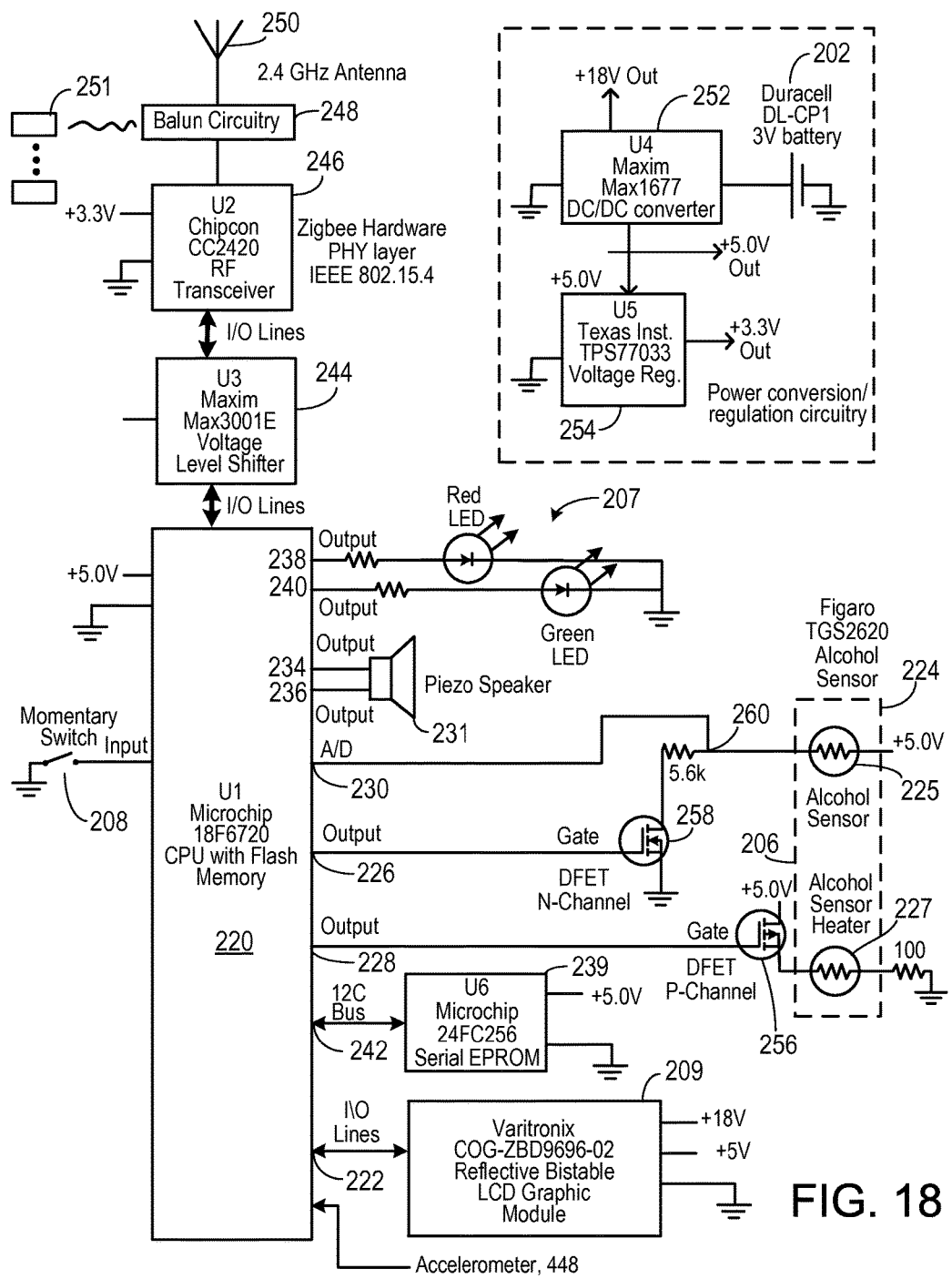
FIG. 18 is a schematic diagram of a badge.

As shown in FIG. 18, the components of the badge 410 are substantially similar to the components of the badge illustrated in FIG. 14 with the accelerometer 448 added. The accelerometer 448 is connected to the PLC chip 432.

Figure 19:
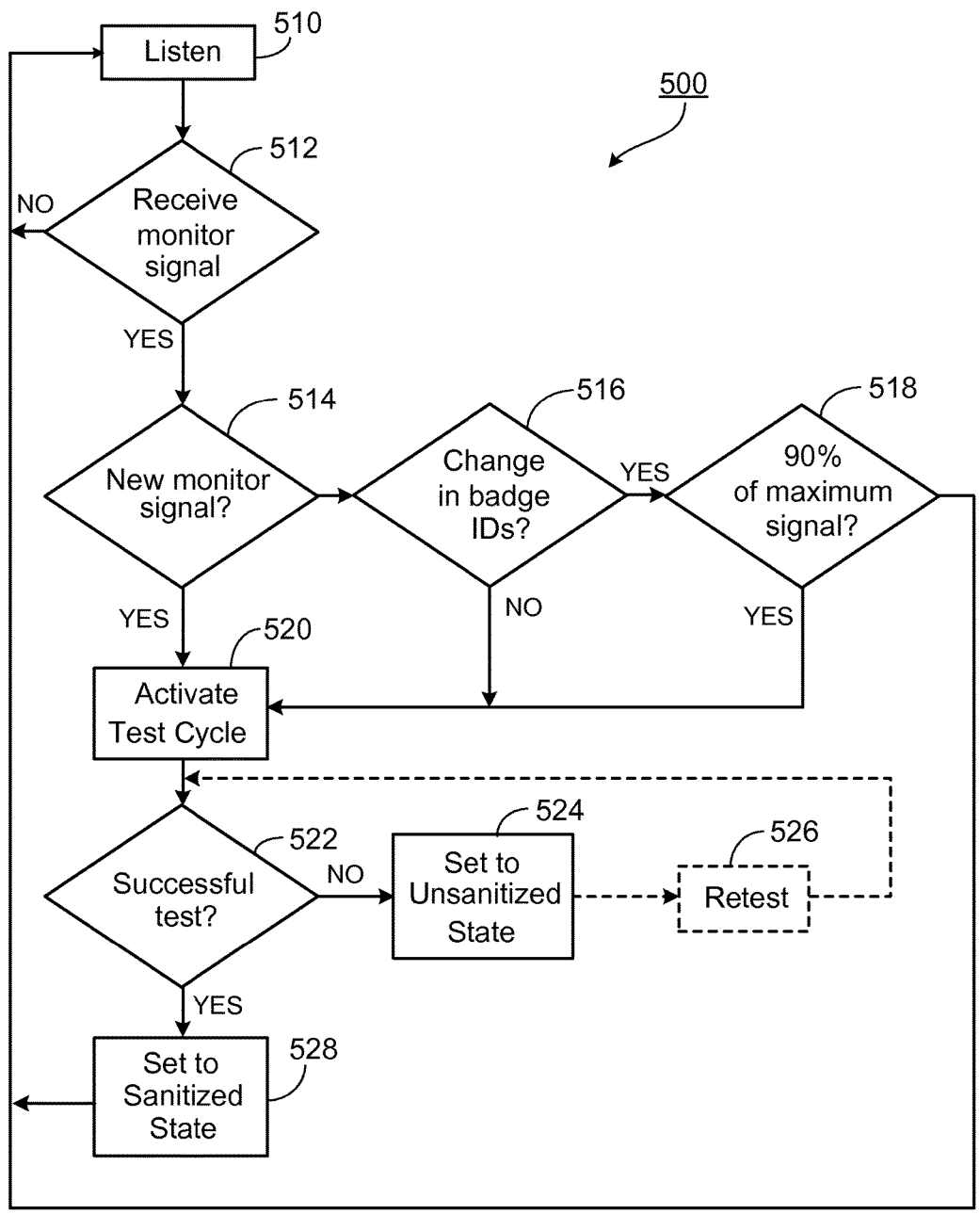
FIG. 19 is a schematic of badge logic.

FIG. 19 illustrates an exemplary state-control logic that can be implemented on PLC chips 432 of the badges 410 used as part of the system 400 illustrated in FIGS. 15A and 15B. FIG. 15B shows a system 400 with monitors 412a, 412b, 412b installed in patient rooms 474a, 474b, 474c near doorways 414a, 414b, 414c from hallway 475.

The badges 410 can be activated, for example, when a badge 410 is removed from a charger where it is being stored, when an accelerometer 448 on a "hibernating" badge 410 indicates that the badge once again being moved, or when a user manually activates a badge 410. When the badge 410 in the illustrated embodiment is initially activated, the PLC chip 432 sets the badge 410 in an un-sanitized state and a user presses the manual triggering button 442 to start a cleanliness test cycle. In some embodiments, the PLC chip 432 automatically starts a testing cycle when a badge 410 is activated.

Upon starting the cleanliness check cycle, the PLC chip 432 activates the alcohol sensor 440 and, while the alcohol sensor 440 is warming up, activates visual or audible indicators to indicate that the badge 410 is in a pre-test state. For example, the PLC chip 432 can turn the green and red LEDs 434, 436 on and off in an alternating sequence to indicate the badge is in a pre-test state. After the alcohol sensor 440 is ready to perform a test, the PLC chip 432 activates visual or audible indicators (e.g., turns the red LED 436 steadily on in an alternating sequence) to indicate that the user can perform a cleanliness check. In some embodiments, the PLC chip 432 sets the badge 410 in testing mode after a set period of time. In some embodiments, the PLC chip 432 monitors the temperature and/or other parameters of the alcohol sensor 440 to determine when the alcohol sensor 440 is ready to perform a test. If a successful cleanliness check is performed, the PLC chip 432 sets the badge 410 in a sanitized state. If a set period of time (e.g., 30 seconds) passes without a successful cleanliness check being performed, the PLC chip 432 sets the badge 410 in an un-sanitized state. To clear the indication that it is in an "un-sanitized" state, the user can press the manual trigger button which signals the PLC chip 432 to begin another cleanliness check cycle.

As described with reference to the other badge embodiments, during a cleanliness check cycle, a user places a portion of their hand against the alcohol sensor grid 422 of their badge 410 and the PLC chip 432 assesses whether there is sufficient alcohol on the user's hands to indicate that they are clean. After a successful cleanliness check is performed, the PLC chip 432 sets the badge 410 in its sanitized state. When the badge 410 is in its sanitized state, badge components including the alcohol sensor 440 and the red LED 436 are turned off, the PLC chip 432 is in a listening mode, and the green LED 434 is turned on.

In the exemplary system 400, the badges 410 are configured to prompt a user to wash his or her hands each time they enter or exit a patient's room. For example, after activating her badge 410a and performing a successful cleanliness check to set her badge 410a in its sanitized state, a doctor starts her rounds which include visiting patients in three rooms 474a, 474b, 474c shown on FIG. 15B.

As the doctor passes through the doorway 414a into a first room 474a, the motion detector 416 signals the PLC chip 452 in the monitor 412a that there has been motion in the doorway 414a. In response, the PLC chip 452 operates the transceiver 464 to send a wireless signal including identification information (e.g., a serial number) of the monitor 412a. In this embodiment, each monitor 412 includes a detector 416 (e.g., an infrared motion detector) which indicates when someone passes through doorway 414. The monitor 412 can be configured to transmit a signal only when the detector 416 indicates that someone is passing through the doorway 414. In some embodiments, the monitors 412 can be configured to transmit signals continuously.

In operation, the state of badges 410 are controlled by the state control logic 500 illustrated in FIG. 19. The state control logic 500 is designed to trigger a cleanliness test cycle when a badge 410 crosses a monitored threshold 414 (e.g., entering or exiting a patient's room) which is generally indicated by receipt of a signal from a monitor 412. The state control is also designed to assess whether a signal received from a monitor 412 was transmitted in response to someone else crossing the monitored threshold 414. It may be undesirable for the badges 410 of people already in a space who have cleaned their hands to be triggered by the entry of another person into the space.

In its sanitized state, the badge 410 displays a green light and listens for signals from monitors 412 (step 510). Until a signal is received from a monitor 412, the badge remains in listening mode. In listening mode, a cleanliness test cycle can be triggered by passage of time and/or by an override signal from a central controller as described with respect to the other embodiments. When the badge 410 receives the signal transmitted by a monitor 412 (step 512), the PLC chip 432 on the badge 410 checks whether this is a new monitor signal (step 514). For example, the PLC chip 432 can compare the received signal with a previously stored signal (e.g., the most recently stored signal in a time-ordered queue 409 of monitor signals stored in onboard memory of the badge 410). If the previously stored location signal is different than the currently received location signal, the badge 410 activates a cleanliness check cycle (step 520) based on the assumption that the person wearing the badge 410 has entered a new monitored room. The PLC chip 432 also stores information about the new signal (e.g., the identification of the transmitting monitor and the signal strength) in the time-ordered queue of monitor signals stored in onboard memory of the badge 410.

The movement of people or objects other than the person wearing a badge 410 through a doorway can cause a monitor at that doorway to transmit a monitor signal. In some embodiments, the badge 410 monitors the presence of other badges in a room to avoid being set to an un-sanitized state when this occurs. For example, if the monitor signal has the same source as a previously received signal (e.g., the same source as in the most recently stored signal information 411 in the time-ordered queue of monitor signals stored in onboard memory of the badge 410), this may imply that the person wearing the badge 410 may be remaining in a room whose monitor has transmitted a monitor signal in response to being triggered. In some embodiments, if the monitor signal has the same source as a previously received signal, the PLC chip 432 returns the badge to listening mode. In the illustrated embodiment, the PLC chip 432 is configured to receive identification signals transmitted by other badges 410 to track which badges are within a specified distance (e.g., within the same room) (step 516). In this embodiment, the PLC chip 432 can be configured to activate the cleanliness check cycle (step 520) if there has not been a change in the badges present when the monitor signal is the same as for the previously stored signal. Other approaches can also be used to identify and track the population of badges in a room and use that information is a basis for avoiding the triggering of the badges of people already in a room due to the passage of other people through the entrance of the room.

In some embodiments, if there has been a change in the badges present, indicating that another person has entered or left a space being monitored, the PLC chip 432 returns the badge to listening mode. In the illustrated embodiment, the PLC chip 432 is configured to monitor the strength of signals received. In this embodiment, the PLC chip 432 returns the badge to listening mode if the received signal strength of a monitor signal that is the same as the previously stored monitor signal is less than a certain percentage (e.g., 90%, 80%, or 70%) of the maximum signal strength recorded for a signal from that monitor (step 518). Otherwise, the PLC chip 432 can the person wearing the badge 410 is passing through a doorway and therefore activate the cleanliness check cycle (step 520). This approach assumes that the maximum signal strength for a monitor is recorded as a health care worker wearing a badge walks through the adjacent doorway.

If the cleanliness check cycle is activated (step 520), the user can operate the badge as described above to check that sufficient alcohol vapor is present to indicate that the user's hands are sanitized. If the test is successful (step 522), the PLC chip 432 can reset the badge to its sanitized state (step 528) and return to the listening mode (step 510).

Figure 20:
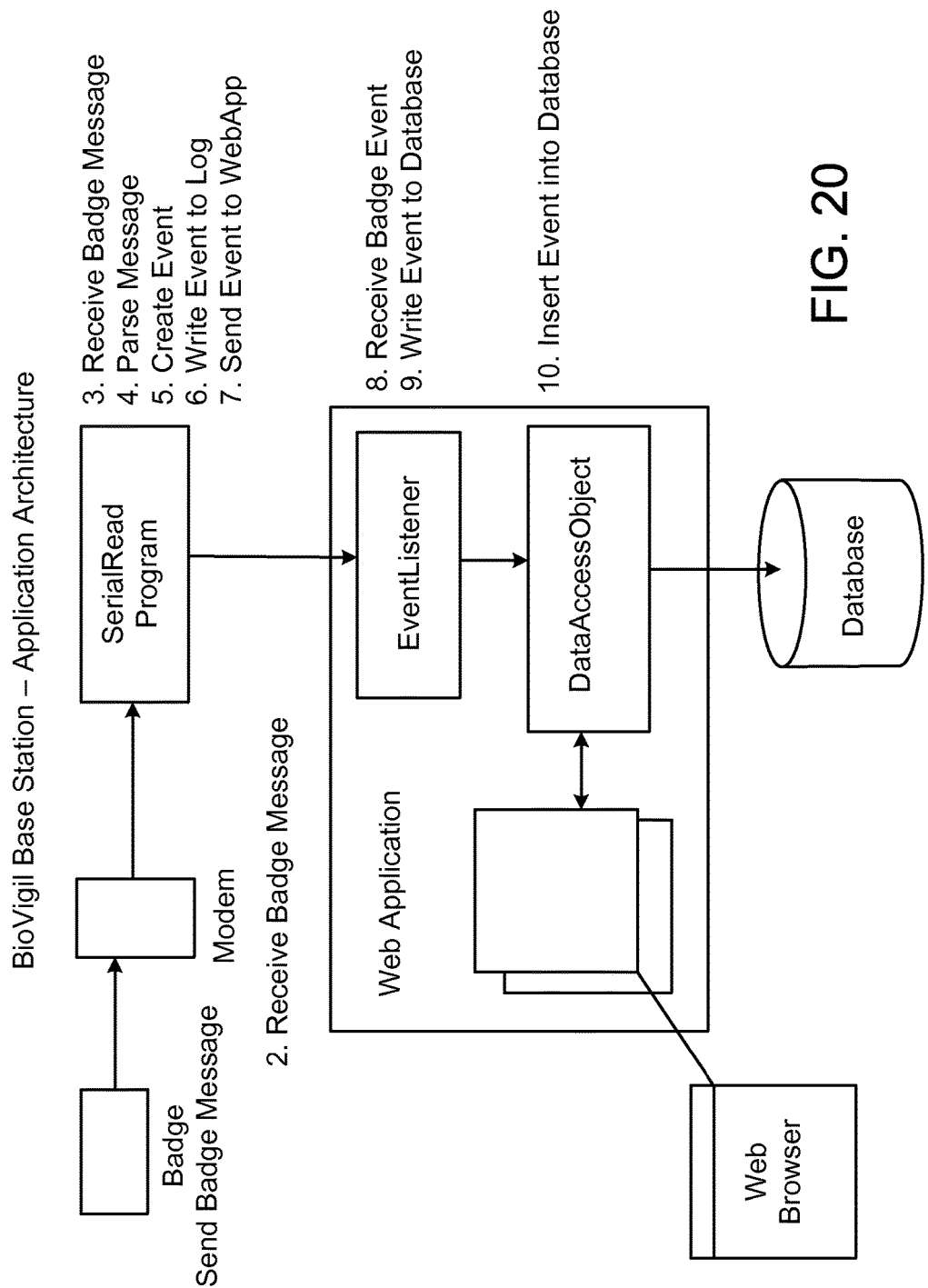
FIG. 20 shows base station application architecture.

As discussed with respect to other embodiments, the badges 410 can store cleanliness test results in onboard memory. The test results and associated data can be periodically downloaded to a base station 523. FIG. 20 illustrates the application architecture for an embodiment of the base station which receives data from the badges 410, stores the data in a database, and provides access to the data (e.g., web-based access). FIG. 21 illustrates a portion of a graphical user interface that can be used to access the data.

In some implementations, monitors 412 can be configured to continuously send badge-switching signals across a doorway or threshold 414. For example, the monitors 412 can include shielding which localizes the badge switching signal being transmitted to the doorway 414 or other threshold being monitored. The badges 410 can be programmed to switch to a non-sanitized state whenever a badge-switching signal is received based on the assumption that whenever a badge-switching signal is received the wearer is entering or exiting a room by crossing a monitored threshold.

This approach can result in "false positives" in which the system mistakenly triggers a cleanliness check cycle for person who merely passes by (rather than crosses) a threshold.

In some implementations, the monitors 412 can continuously send badge-switching signals throughout the room in which the monitors 412 are installed. The associated badges 410 switch to a non-sanitized state upon first receiving a badge-switching signal from a specific monitor 412. After the person wearing the badge 410 has cleared the non-sanitized state by running a successful test cycle, the badge 410 will ignore the badge-switching signal transmitted by the specific monitor which triggered the test cycle as long as the badge 410 remains in communication with that specific monitor. The badge interprets a loss of communication with that specific monitor as indicating that the wearer has exited the monitored space and switches to a non-sanitized state upon loss of communication. This approach does not require the monitor to include a detector but can sometimes result in the badge 410 unnecessarily switching to a non-sanitized state. For example, if a technician wearing a badge 410 moves behind a badge that blocks the signal from the monitor 412, the badge could be switched to a non-sanitized state. The badges 410 can be configured with a time-delay before the signal loss switches the badge state as a method of reducing such unnecessary switching.

As illustrated in FIGS. 22A-22D, some embodiments of a system 600 configured to prompt individuals 601 (e.g., health-care workers, only one shown) to sanitize their hands 603 on entering or exiting a specific space (e.g., a patient's room) include badges 610 (only one shown in FIG. 22A), a monitor or monitors 612a, 612b that provide dual signals at a threshold of the space, such as a doorway 605, and a base station 614. In these embodiments, the wearable badges 610 can prompt a user to clean his or her hands, verify that his or her hands have been cleaned (e.g., sense the presence of alcohol hand sanitizer), and record the activities of the wearer. The monitors 612a, 612b can be mounted above an entrance 613 (an example of a threshold) to a space (e.g., above a doorway leading into a patient's room) emitting at least two signal beams 615, 617 downward as a way to trigger a hand-cleaning process. As explained in more detail below, the badges 610 are configured to recognize that they have crossed a boundary based on rapid transitions in the receipt at the badge of different signal beams. This dual signal beam approach can reduce the likelihood of that badges 610 will unnecessarily switch to a non-sanitized state.

The base station 614 (see FIG. 22B) can collect data from multiple badges and provide an overview of hand-cleaning events.

The monitors 612a, 612b can be mounted above the doorway of a room each to emit a signal-carrying beam 615, 617 (e.g., infrared light) in a downward direction 619. In some embodiments, the monitors 612a, 612b can be adhesively attached to a door frame or wall. In some embodiments, the monitors can be mechanically attached to the door frame or wall.

The monitors can be mounted with first monitors 612a inside the doorway and second monitors 612b outside the doorway. For example, in some implementations, the monitors 612a, 612b can include infrared light emitting diodes (LEDs) which continuously emit infrared light downwards towards a floor 616 in the form of a conical infrared light beam 623 an angle of dispersion $\alpha$ (FIG. 22D) substantially perpendicular to the plane 625 of the doorway of about 60 degrees (e.g., between about 50 and 70 degrees) and at an angle of dispersion $\beta$ (FIG. 22A) substantially parallel to the plane of the doorway of about 60 degrees (e.g., between about 50 and 70 degrees). As can be seen in FIGS. 22C and 22D, this configuration can provide a signal field 627 that is localized in the vicinity of the threshold 629 being monitored. This configuration can provide lateral overlap between the signal beams from adjacent inside monitors in order to provide uninterrupted coverage and between the signals from adjacent outer monitors with limited or no overlap between the signal beams of inside monitors and the signal beams of outside monitors.

Figure 22A:
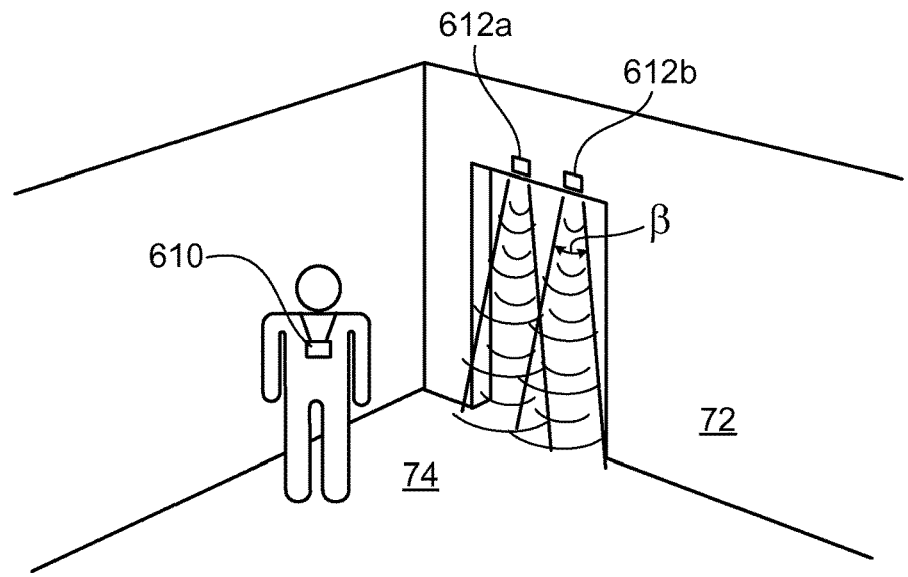
FIGS. 22A-22E are schematic views of a cleanliness monitoring system.
Figure 22B:
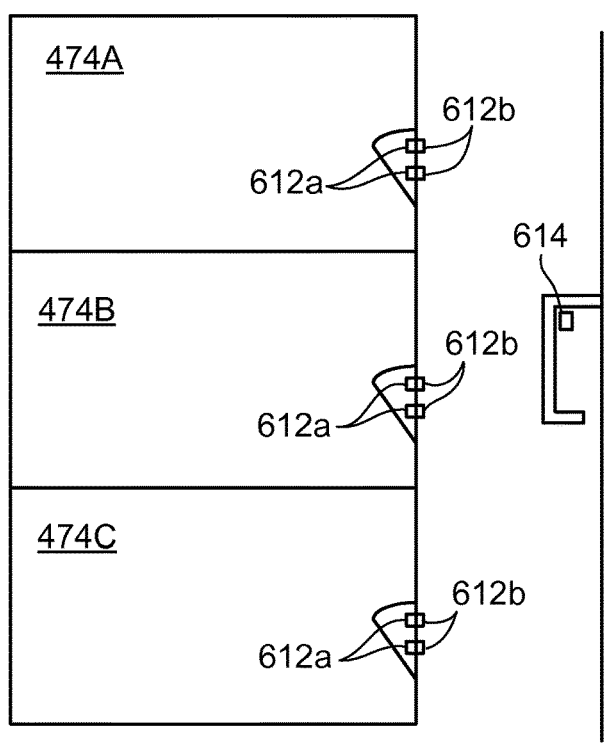
Figure 22C:
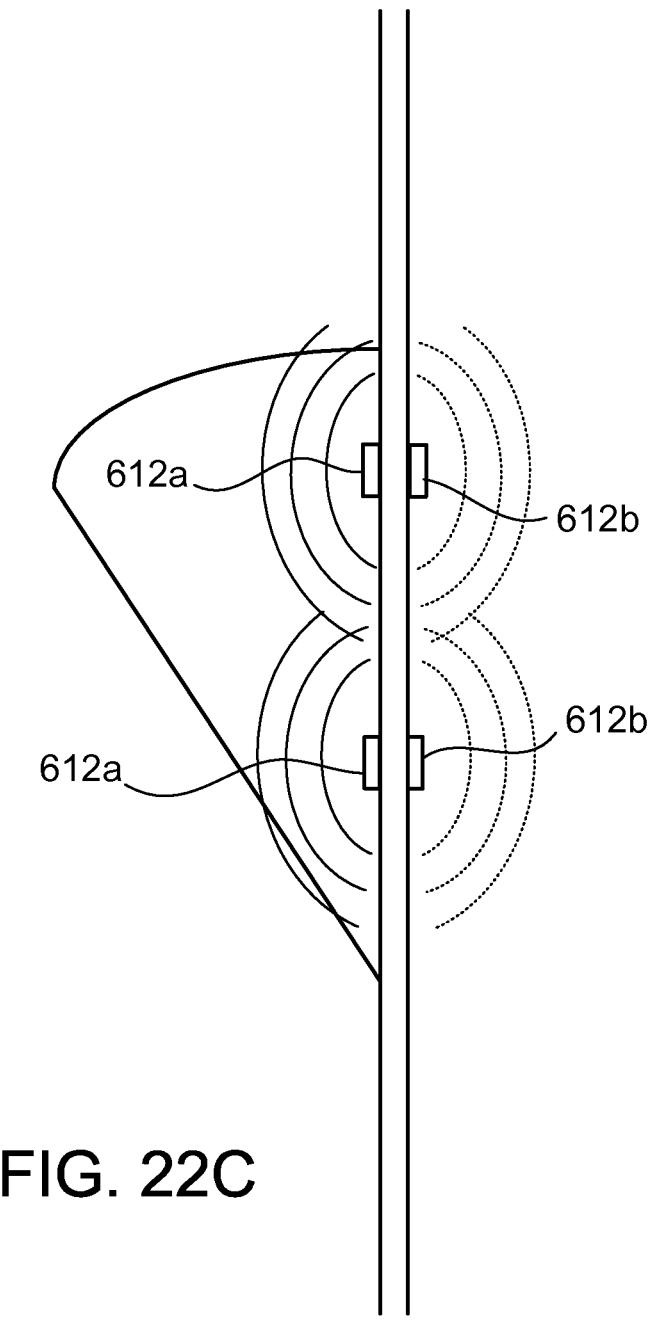
Figure 22D:
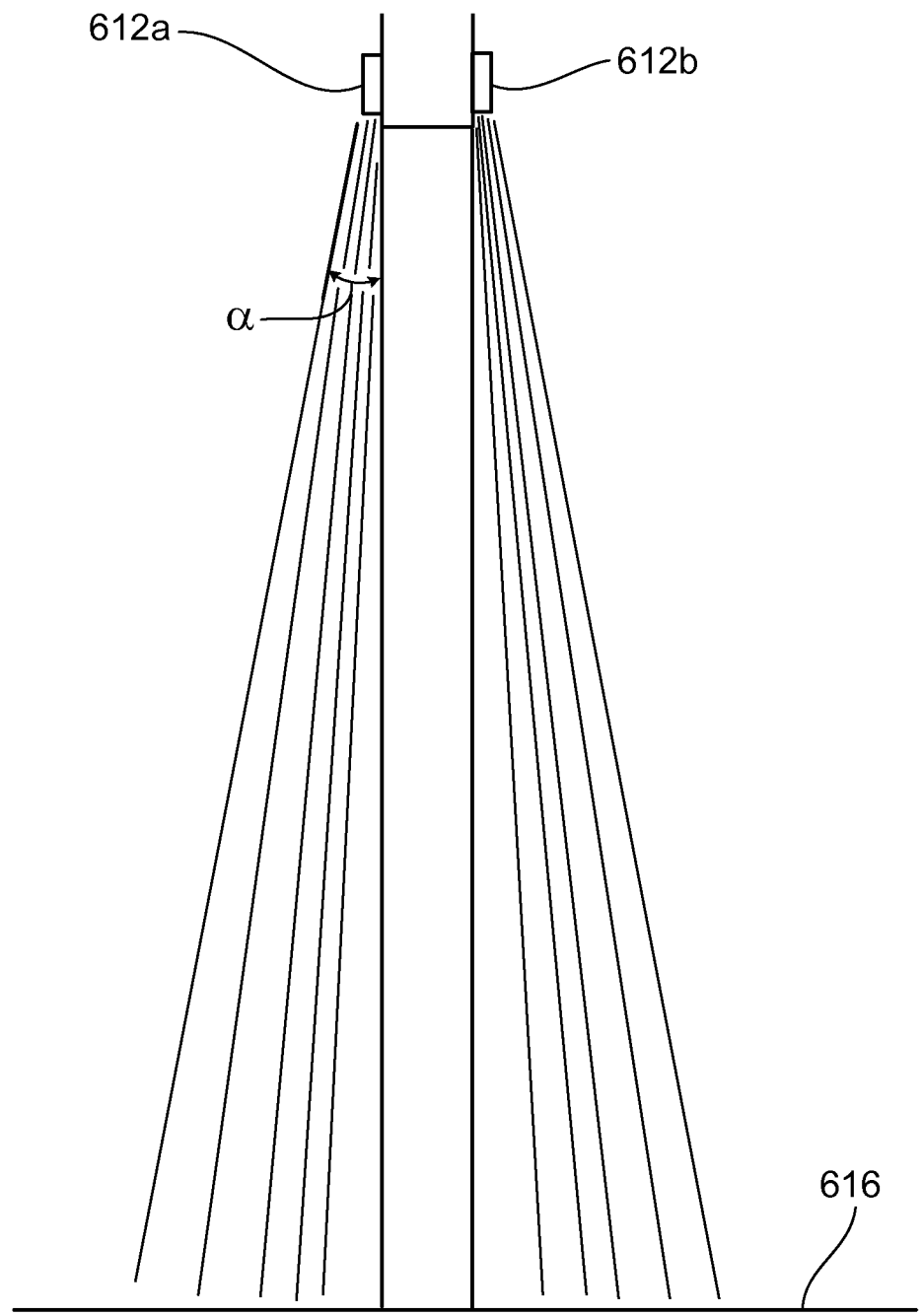
Figure 22E:
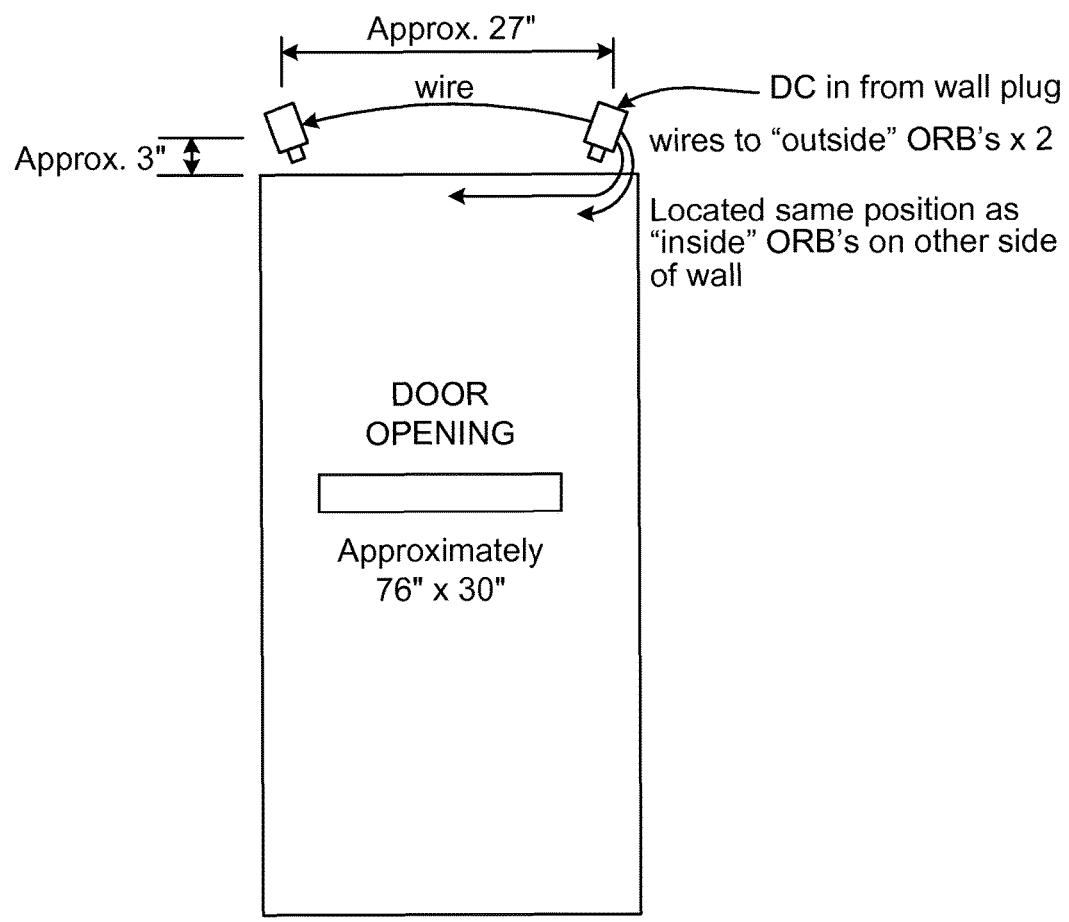

In a test of the illustrated embodiment, the monitors used were mounted as illustrated in FIG. 22E. Two inside monitors 612a were mounted about 24 inches apart (e.g., about 12 inches from the doorway centerline) on the inner upper frames of 30 inch doorways and two outside monitors 612b were mounted at corresponding locations on the outer upper frames of the doorways. The alpha and beta angles of dispersion were about 60 degrees and 60 degrees respectively. This configuration provided lateral overlap between the signals from adjacent inside monitors and between the signals from adjacent outer monitors with limited or no overlap between the signals of inside monitors and the signals of outside monitors.

Figure 28A:
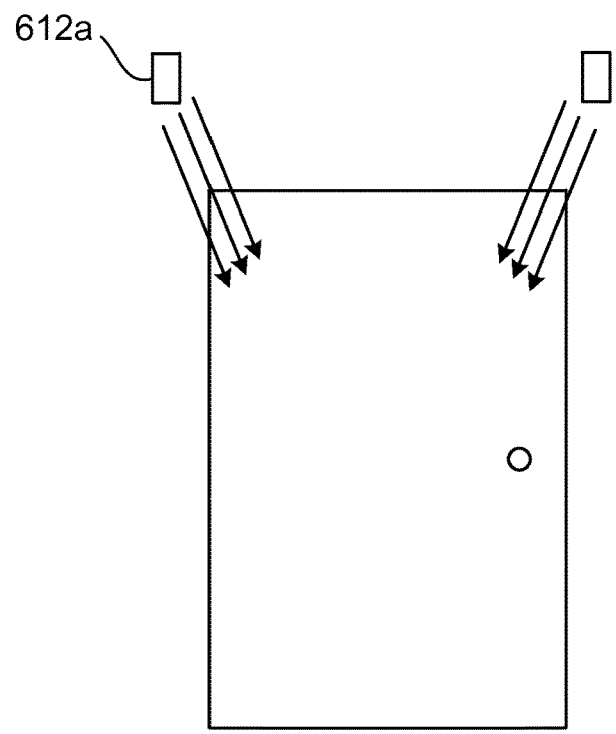
FIGS. 28A-28B are schematic views of the monitors of a cleanliness monitoring system.
Figure 28B:
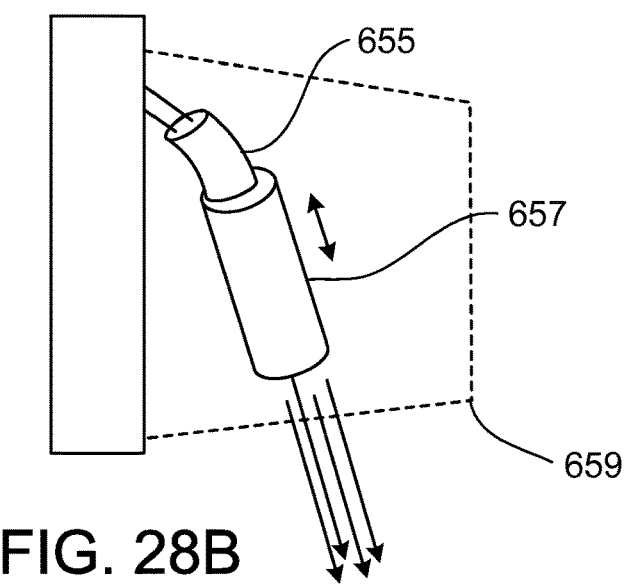

FIGS. 28A-28B illustrate an approach to mounting the monitors 612a. In this approach, the pairs of monitors 612a are mounted above or slightly outside the side edges of the door frame. Each of the monitors 612a can include an infrared light emitting diode 655 disposed in a plastic sleeve 657 (e.g., a cylindrical plastic sleeve) to confine and direct the infrared light. Each of the monitors 612a can also include a cover 659 (e.g., a plastic cover opaque to visible light and translucent to infrared light) that is on the side of the monitor facing the room or hallway. This implementation of monitors 612a can improve the focus and directivity of the infrared light beam, inside and outside of doorways.

Figure 29A:
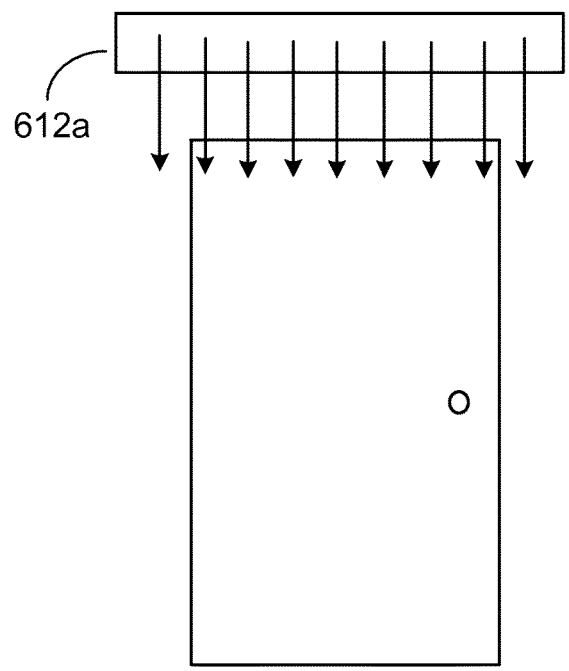
FIGS. 29A-29C are schematic views of the monitors of a cleanliness monitoring system.
Figure 29B:
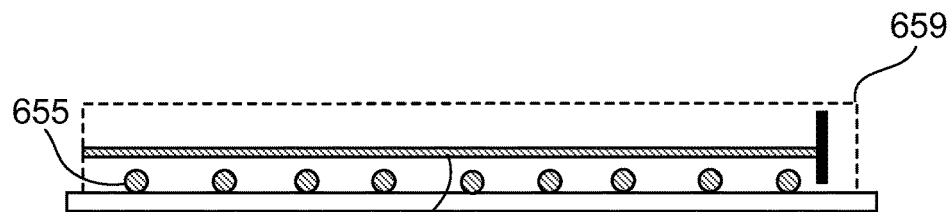
Figure 29C:
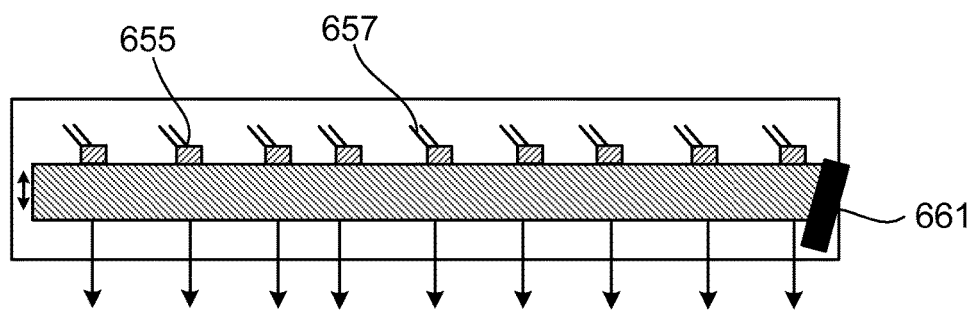
Figure 30:
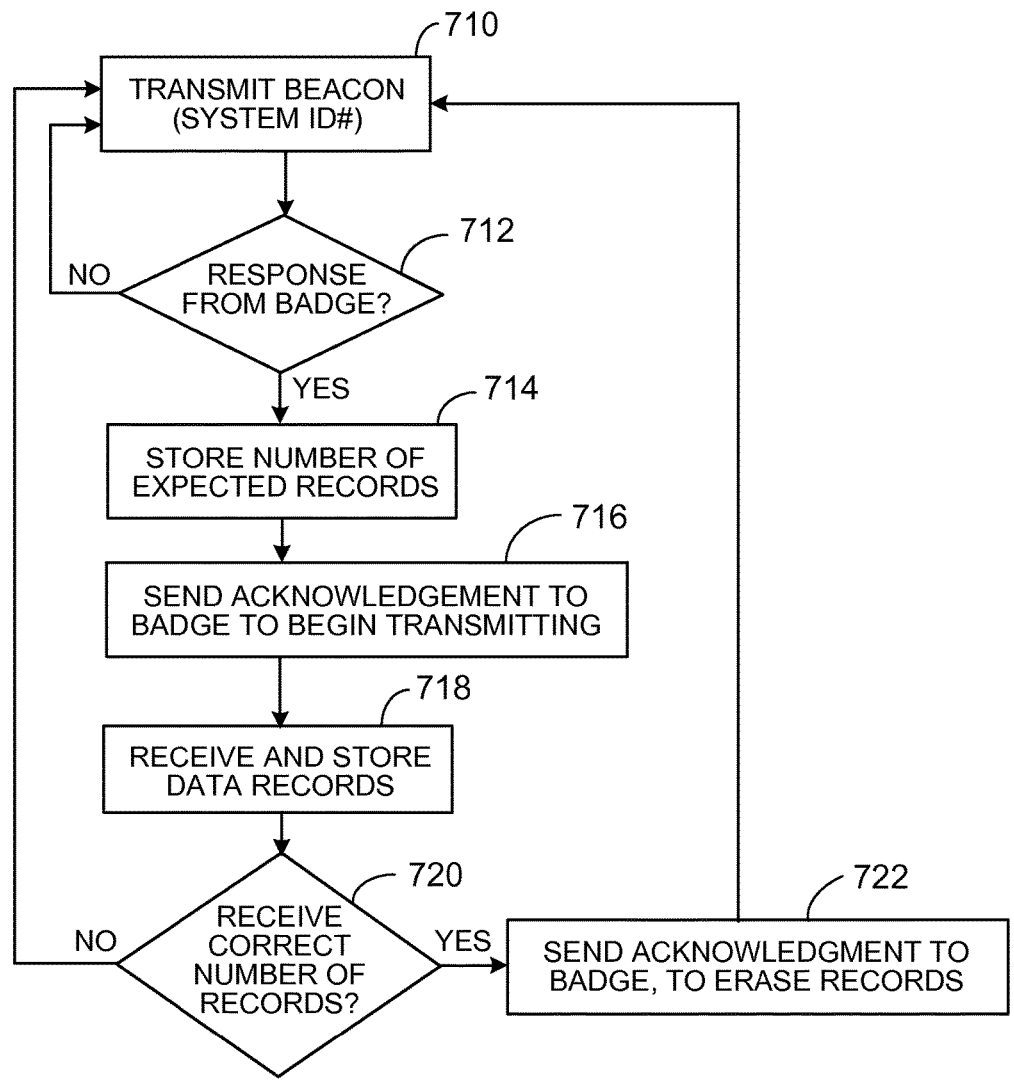
FIG. 30 is a schematic of base station logic.
Figure 31A:
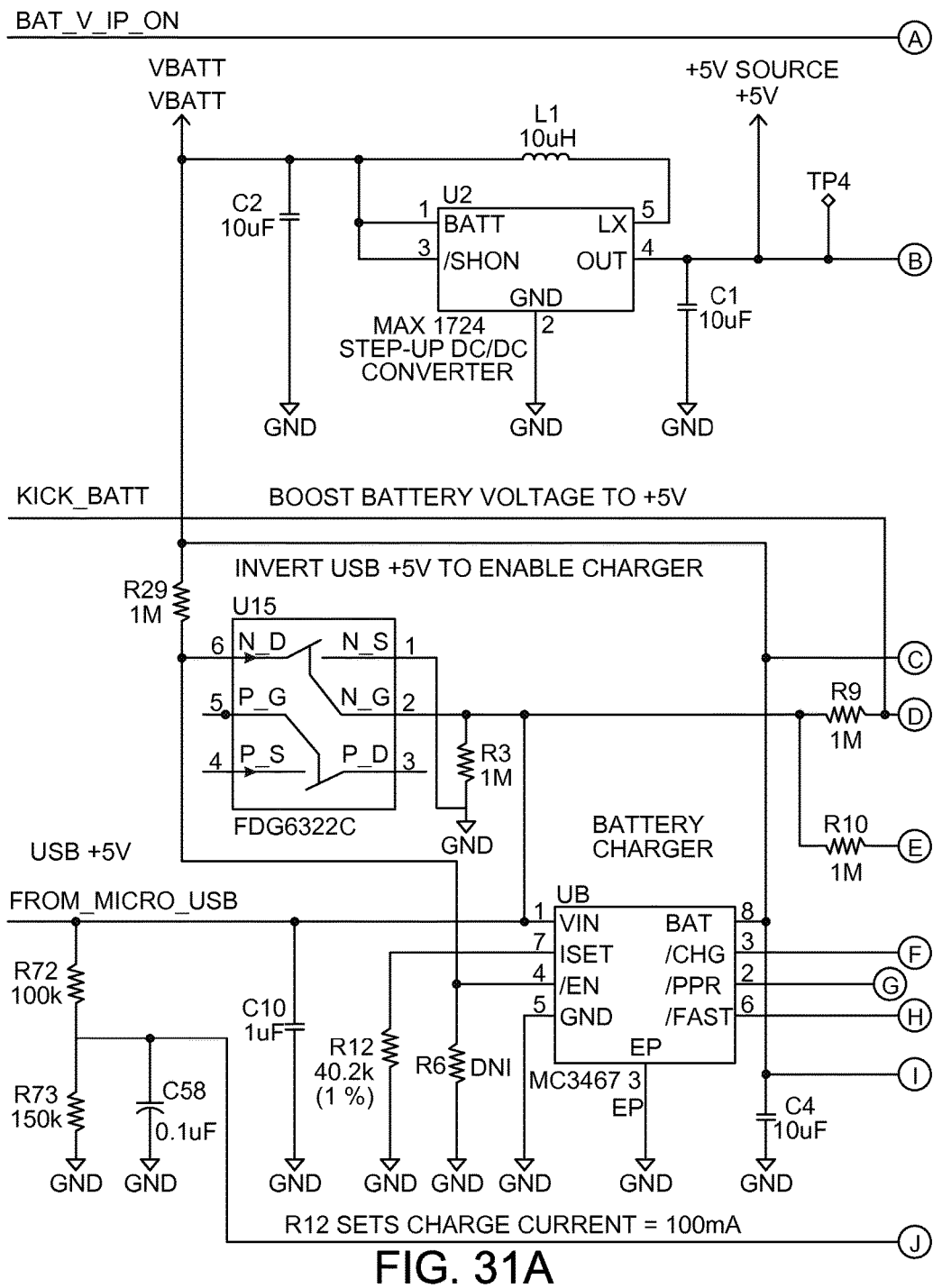
FIGS. 31A-31J are wiring schematics for embodiments of a badge, a monitor, and a base station.
Figure 31A:
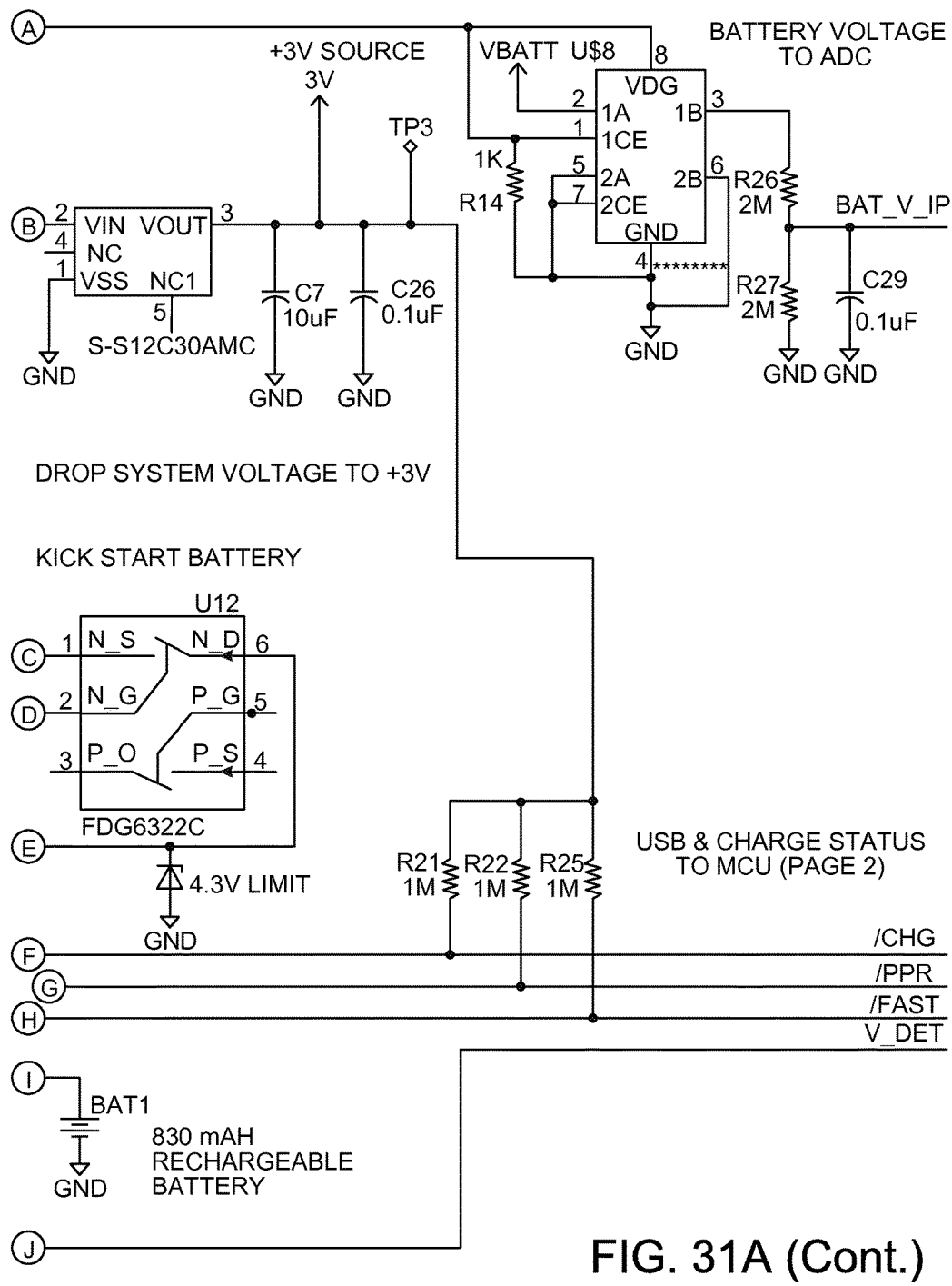
Figure 31B:
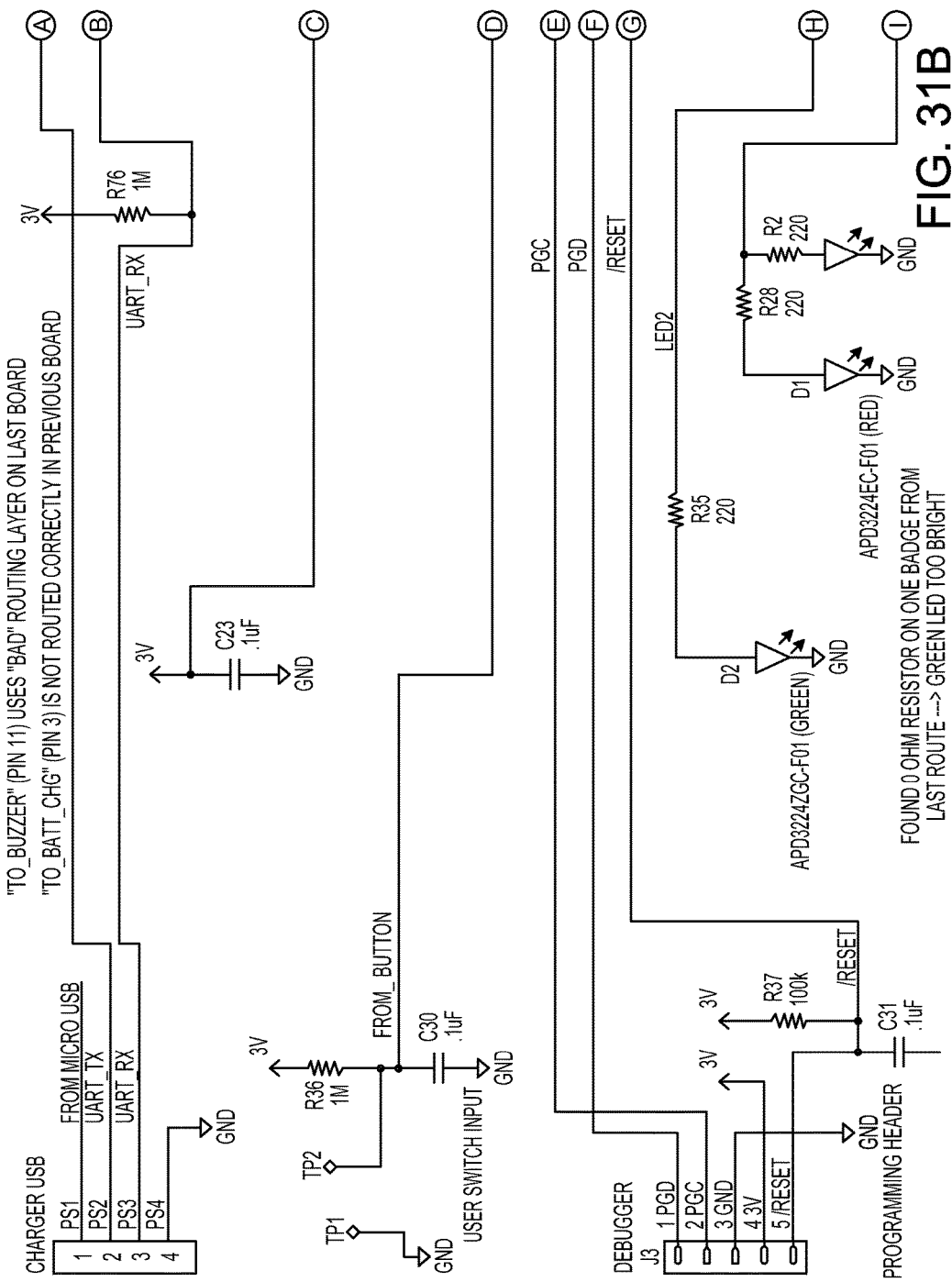
Figure 31C:
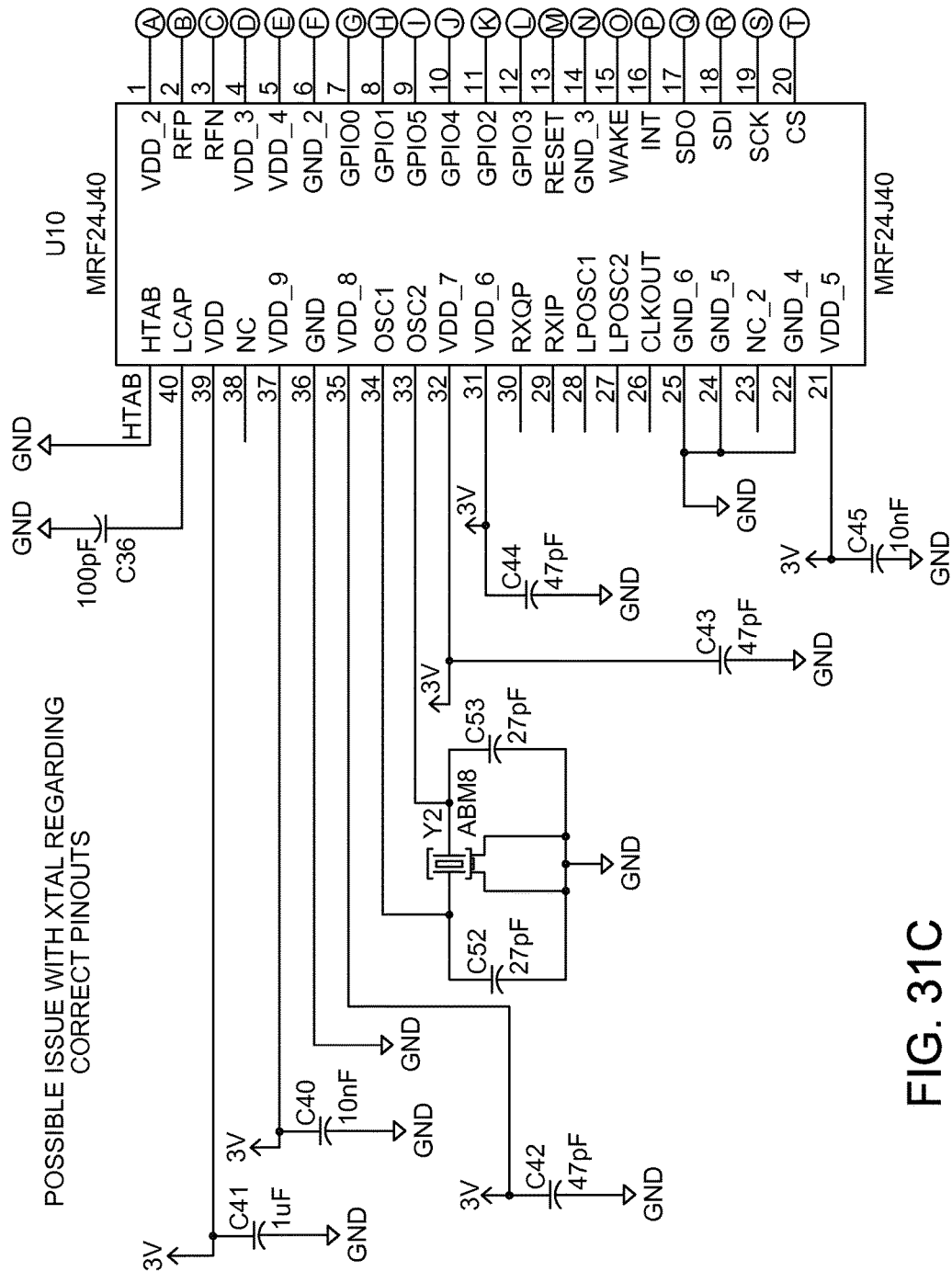
Figure 31C:
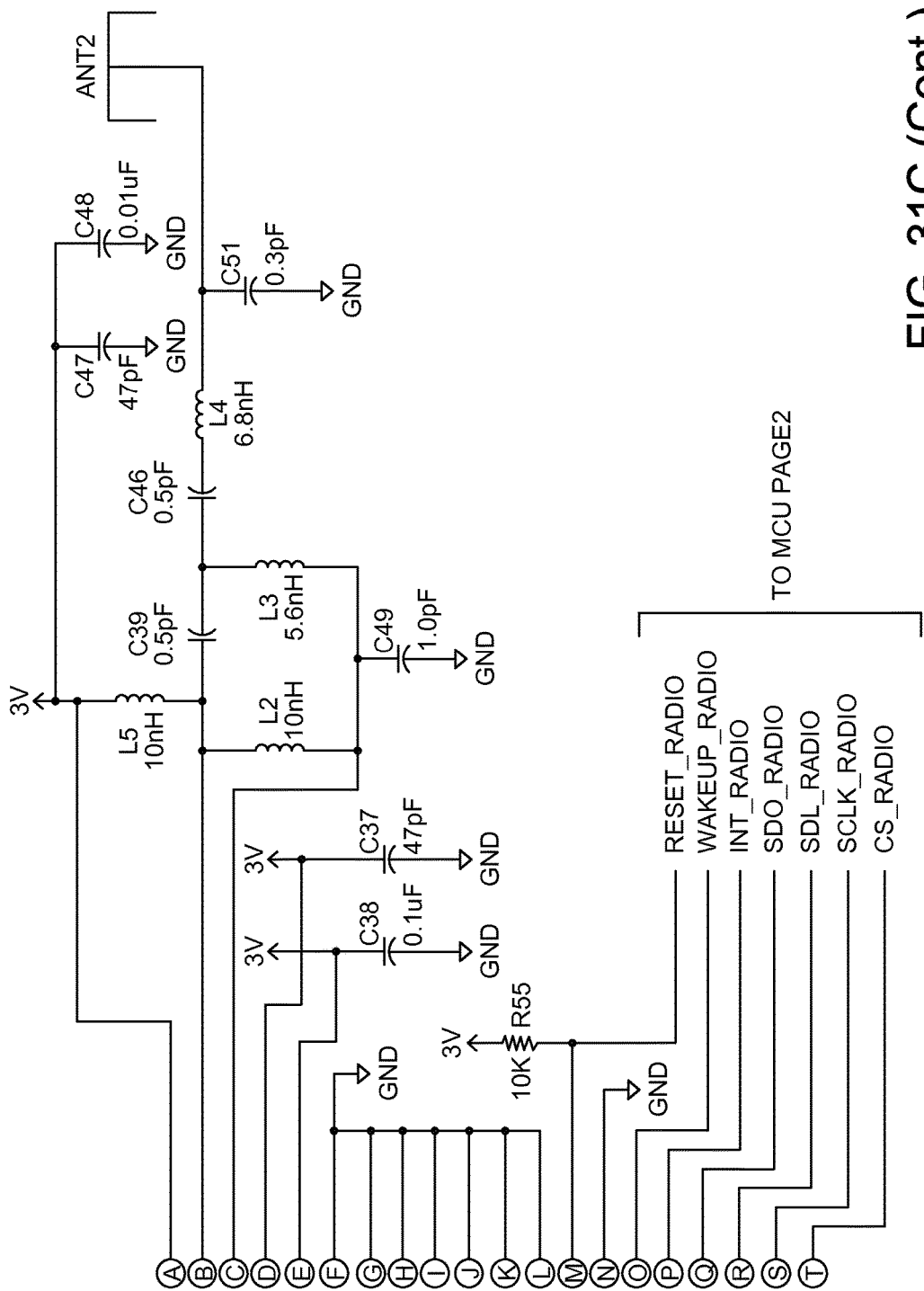
Figure 31D:
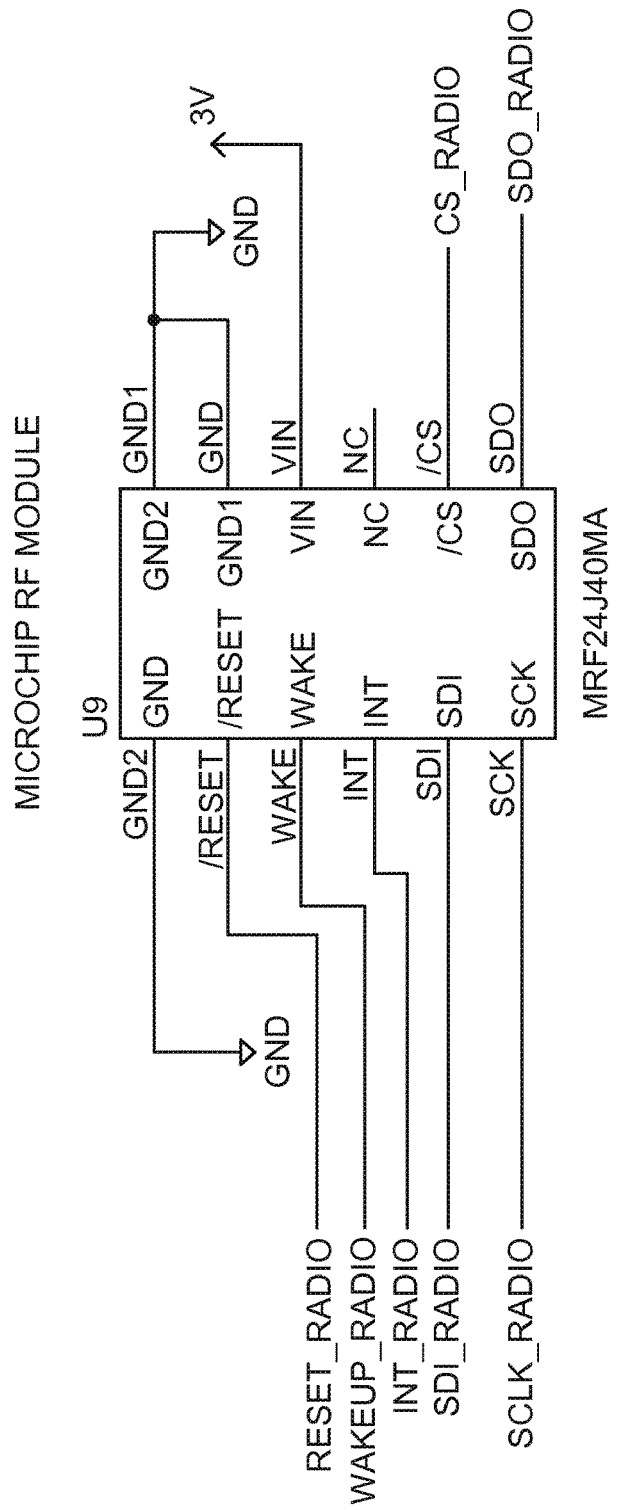
Figure 31E:
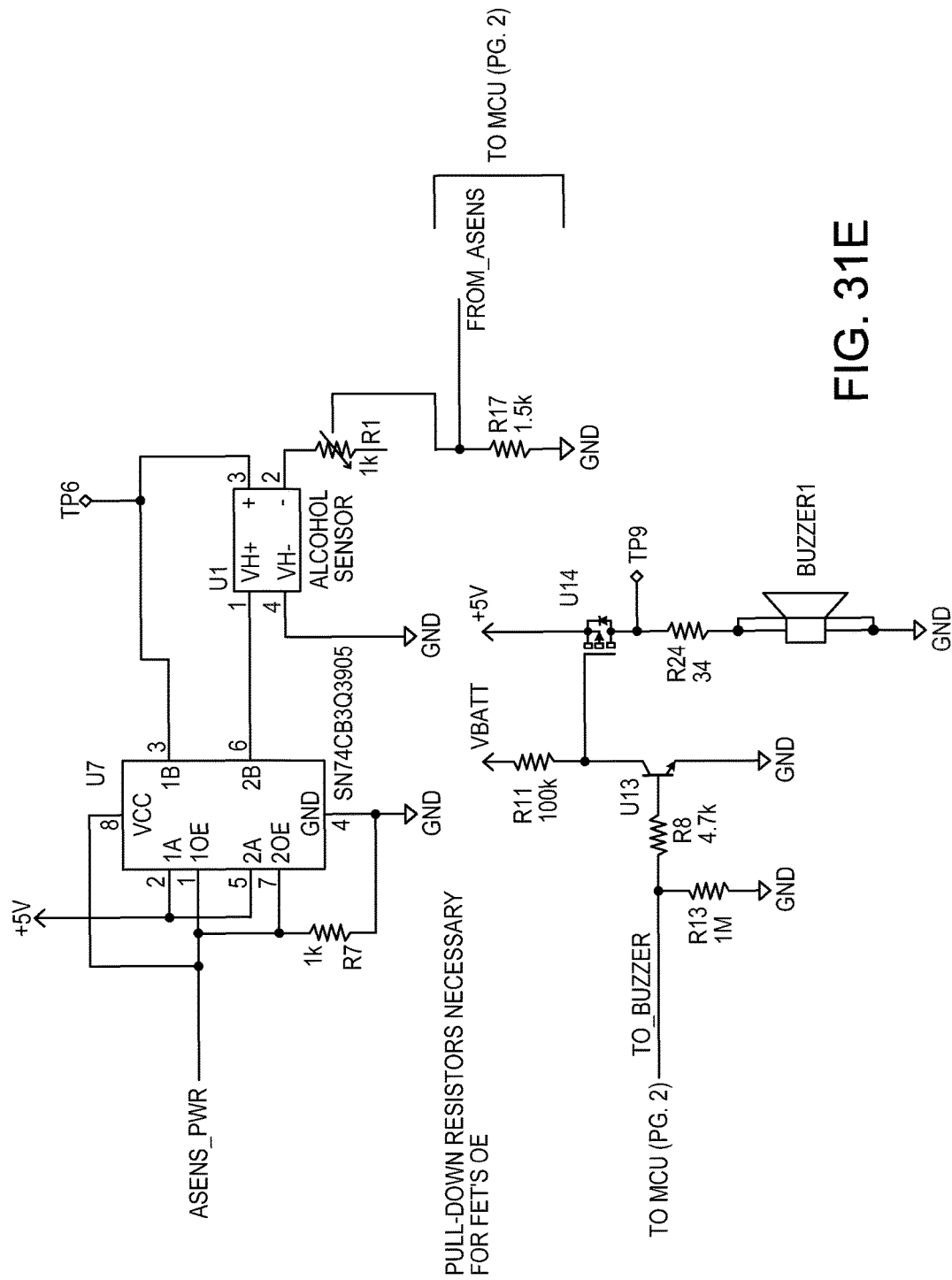
Figure 31F:
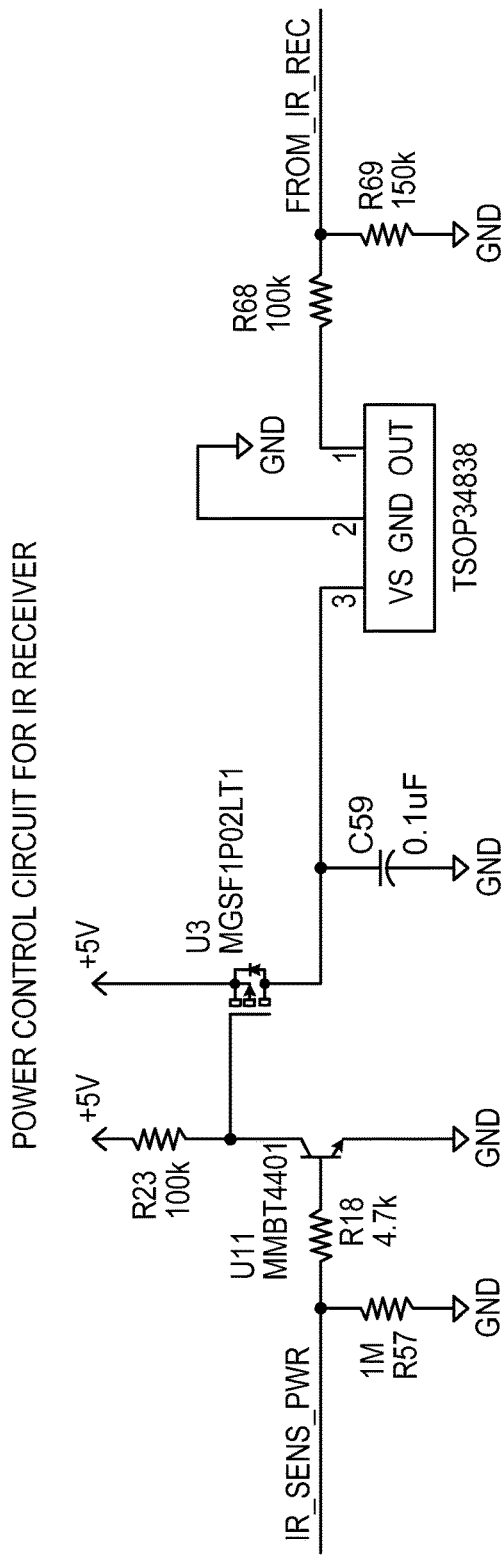
Figure 31G:
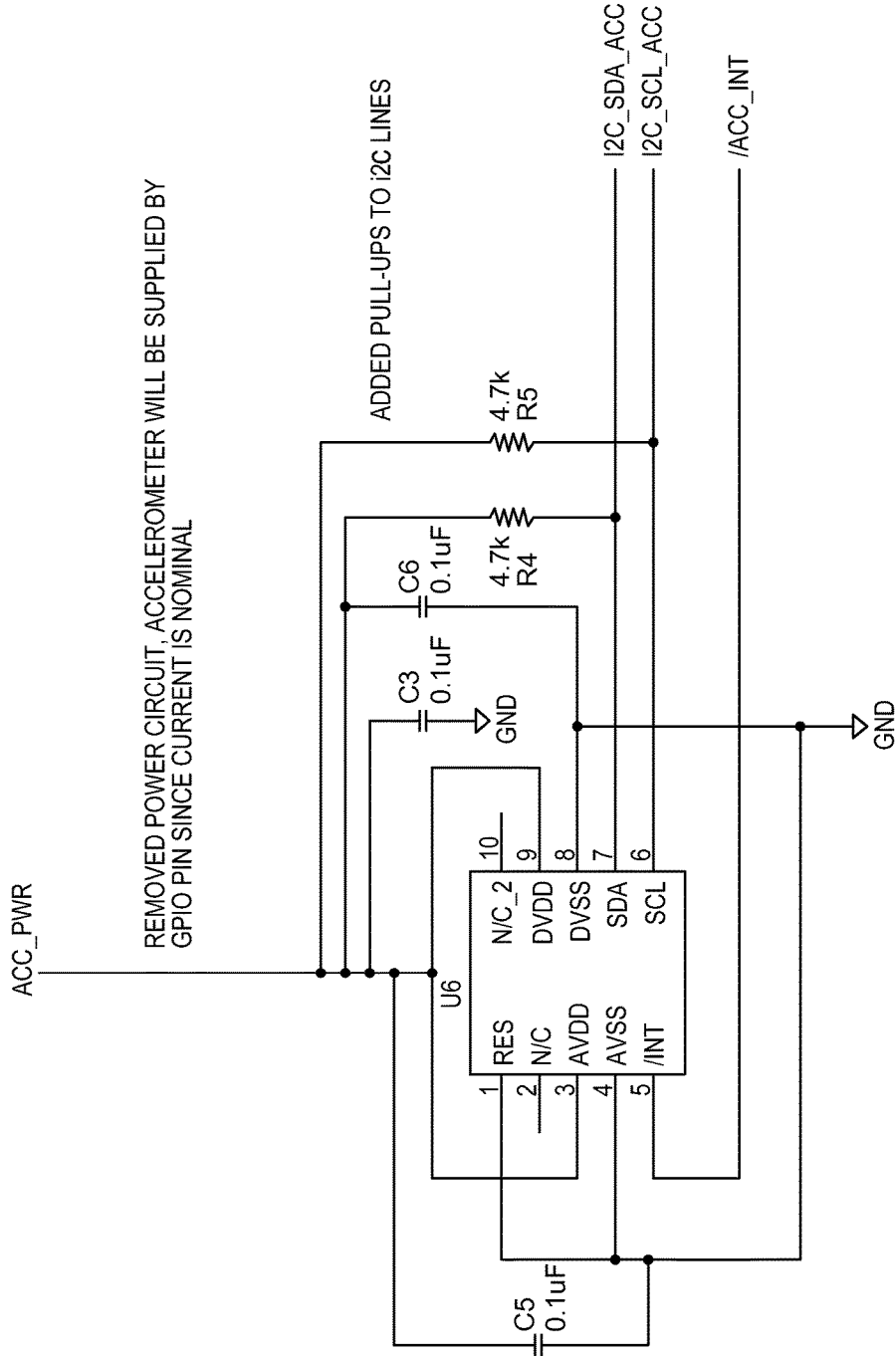
Figure 31H:
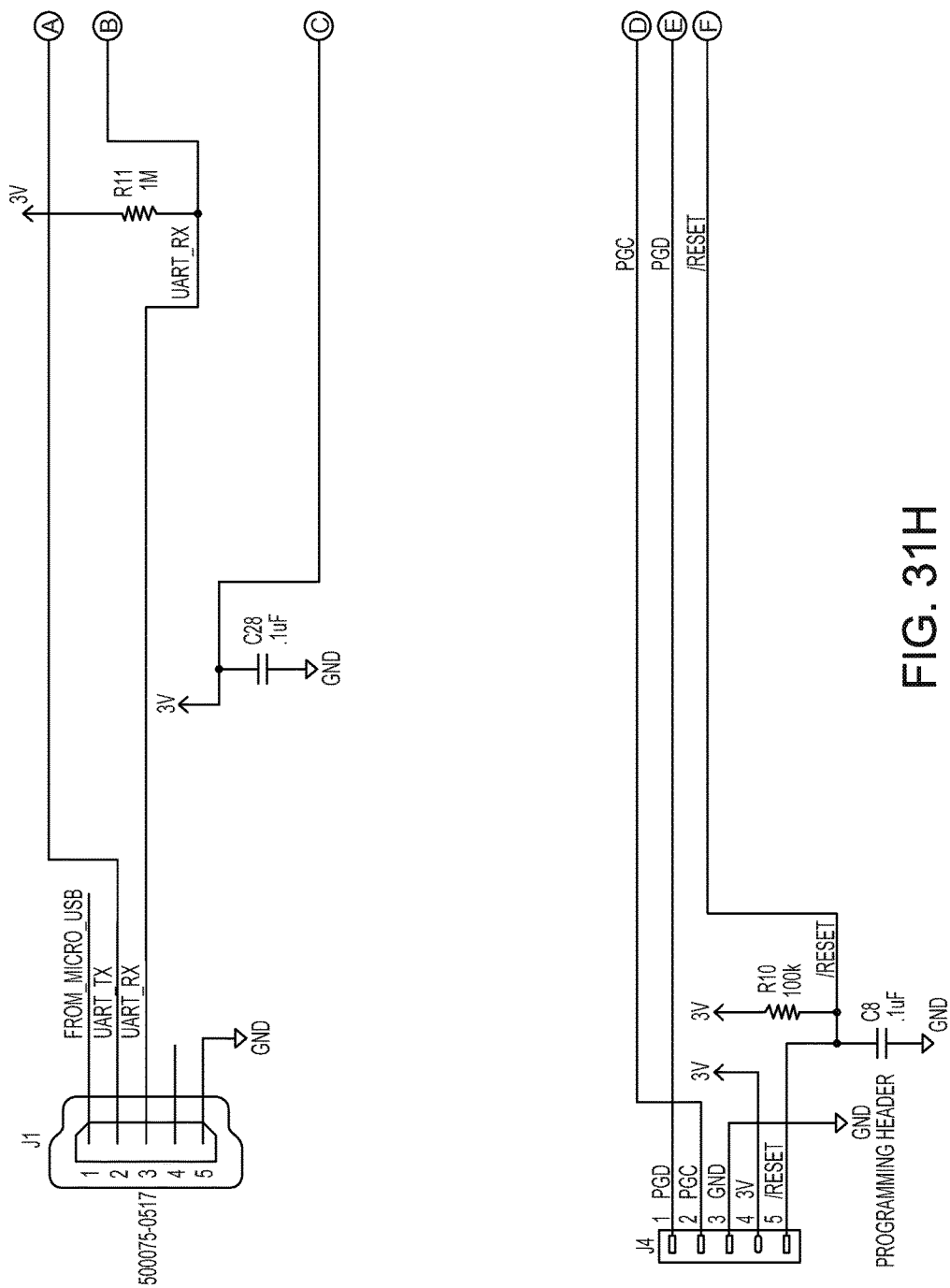
Figure 31H:
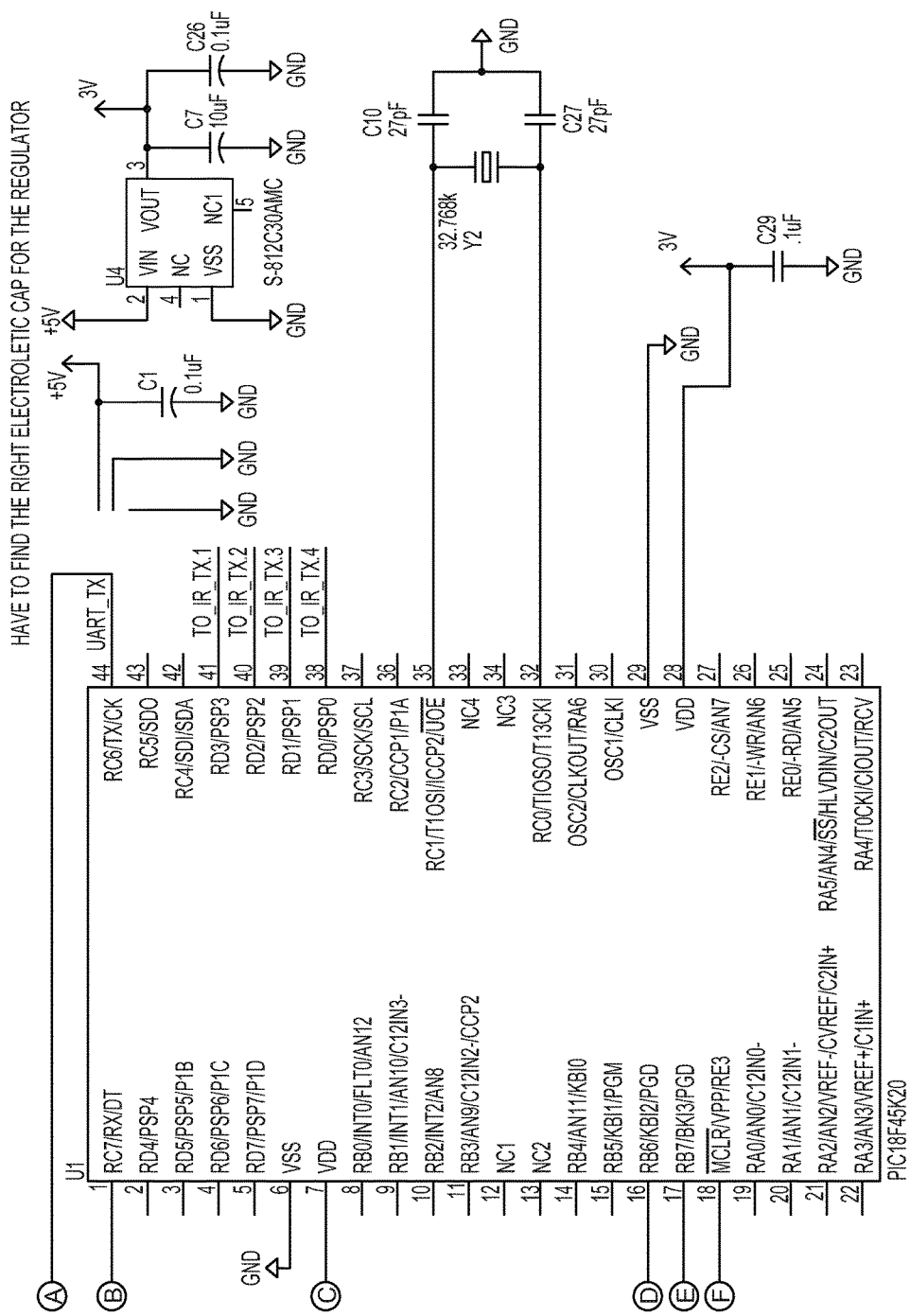
Figure 31I:
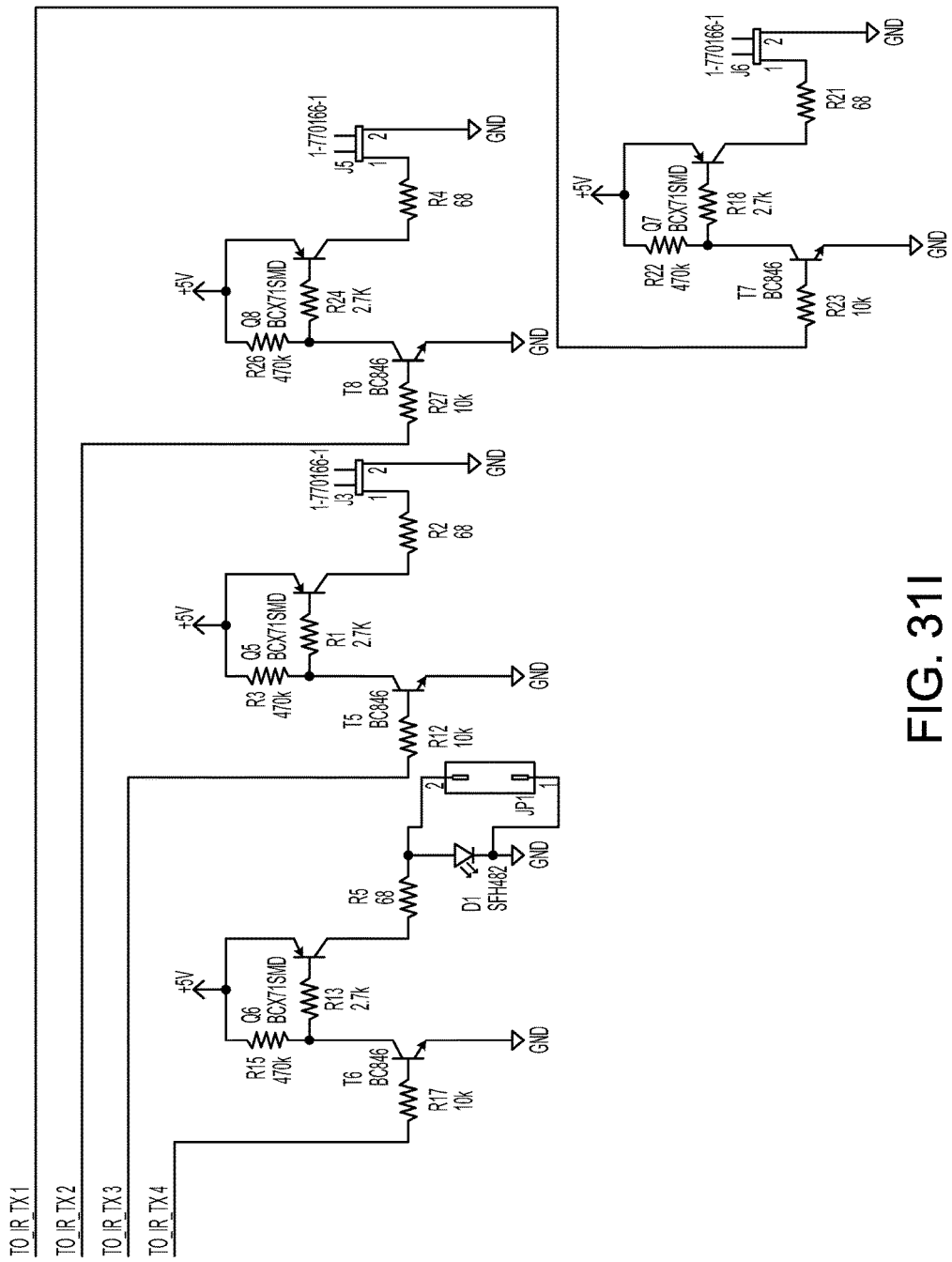
Figure 31J:
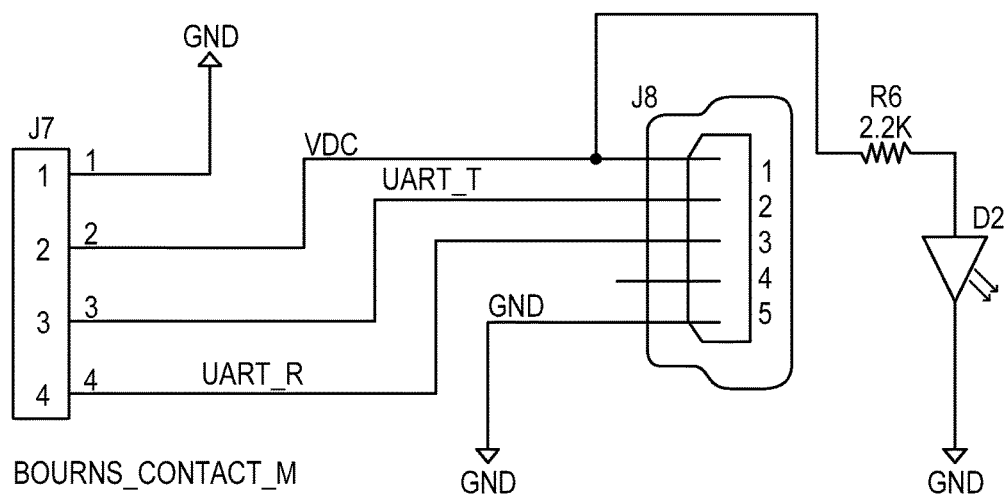

FIGS. 29A-29C illustrate a monitor 612a implemented as a "light curtain." The monitor 612a can include multiple infrared light emitting diodes 655 arranged in a light strip within a cover 659 (e.g., a plastic cover opaque to visible light and translucent to infrared light). A plastic sleeve 657 (e.g., a rectangular shroud on the side of the monitor facing the room or hallway) extends over the multiple infrared light emitting diodes 655 to confine the infrared light emitted by the monitor to the vicinity of the doorway, that is, to confine the infrared light to a space that is typically no more than 36 inches into the room or hallway relative to the door. The sleeve can be attached to a mechanism (e.g., a lever, an adjustable screw mount) operable to control the position of the plastic sleeve relative to the light emitting diodes 655 and, thus, the configuration of the infrared beam emitted by the monitor 612a.

Monitors are available that have a variety of emitter coverage patterns. The system 600 can be designed using monitors that have different emitter coverage patterns and/or different configurations of monitors. For example, larger boundaries (e.g., the threshold between the central aisle and bed spaces of an open bay ward or large double doorways) can be covered by more monitors and/or by monitors with wider emitter coverage patterns arranged to provide the rapid transition between inner and outer signals used to identify the boundary location. For example, in some embodiments, a badge can identify a boundary if the transition between signals occurs in less than 2 seconds (e.g., less than 1 second or less than 0.5 seconds). In some embodiments, a single monitor can be configured to provide both inner and outer signals with limited or no overlap between the inner signals and the outer signals.

The terms "inside," "inner," "outside," and "outer" are used for ease of describing the locations relative to the hallway-room building plan shown in FIG. 22B. Such monitors could be used to identify boundary locations in other settings including, for example, an outdoor boundary line where none of the monitors used are inside a building or a shape defined by the boundary.

The first monitors 612a mounted inside the doorway and second monitors 612b mounted outside the doorway emit different signals (e.g., the infrared beams of different monitors can be modulated to carry different identification signals). As is discussed in more detail below, the badges 610 can identify when the user crosses the threshold being monitored and the user's direction of travel based on the different signals emitted by the first monitors 612A and the second monitors 612B. In some embodiments, each monitor 612 emits a unique signal (e.g., a serial or identification number). In these embodiments, the locations of individual monitors 612 can be pre-stored in a database on the badges 610 and/or at a central monitoring station. In some embodiments, the first monitors 612a emit a first common signal and the second monitors 612B emit a second common signal, for example, a signal that indicates that a given monitor is either an inside monitor or an outside monitor.

Figure 23:
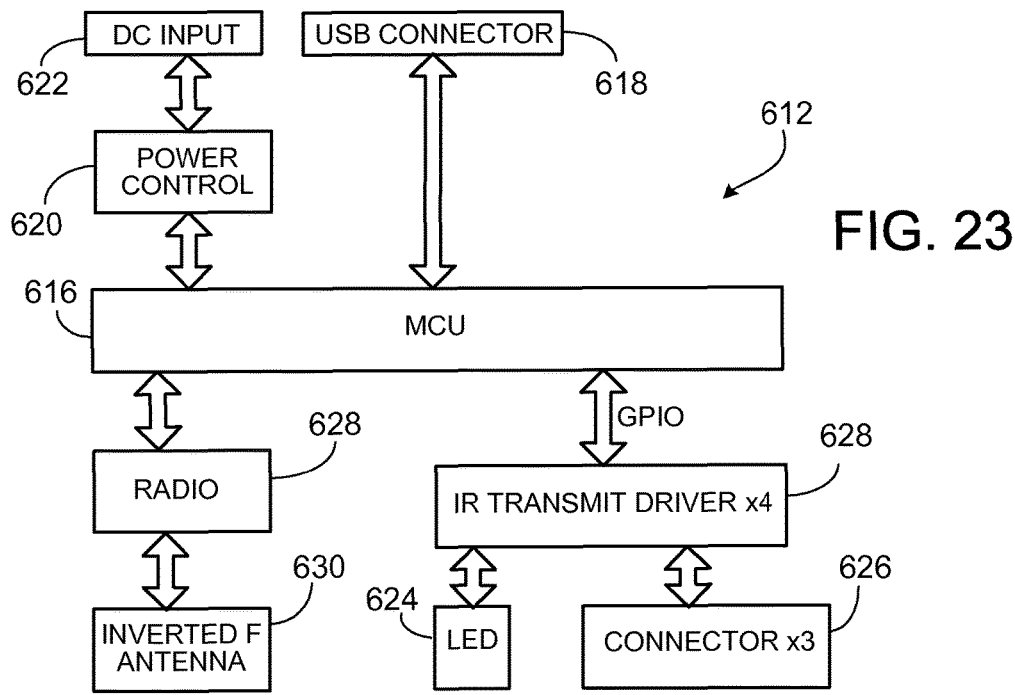
FIG. 23 is a schematic view of a monitor.

In a test of the illustrated embodiment, the monitors 612 were configured to continuously emit a beam of infrared radiation modulated to carry identification signals that were received by any badge within range (e.g., passing through a monitored doorway). As illustrated in FIG. 23, each of the monitors 612 included a PLC chip as a microcontroller unit (MCU) 616 and a USB connector 618 to provide operator access to the MCU (e.g., to set the signal being emitted by the monitor 612). A power control 620 connects the MCU to a power input 622. In the test, the monitors 612 were powered by wall plugs. In some embodiments, the monitors 612 can be powered by other means including, for example, photovoltaic cells and/or batteries. The MCU 616 controlled the infrared signal emitted by infrared a light emitting diode 624 through an infrared transmit driver 626. Connections 626 available for up to three other light emitting diodes were not used.

In this embodiment, the monitors 612 did not utilize any sensors or radiofrequency communications, but acted simply as a trigger to cause badges to record events corresponding to entering or exiting a room. The monitors 612 used in the test included radiofrequency transceivers 628 with antennas 630 to provide additional communication links for radiofrequency communication as needed. Such radiofrequency transceivers can provide high rate data transmission.

Figure 24:
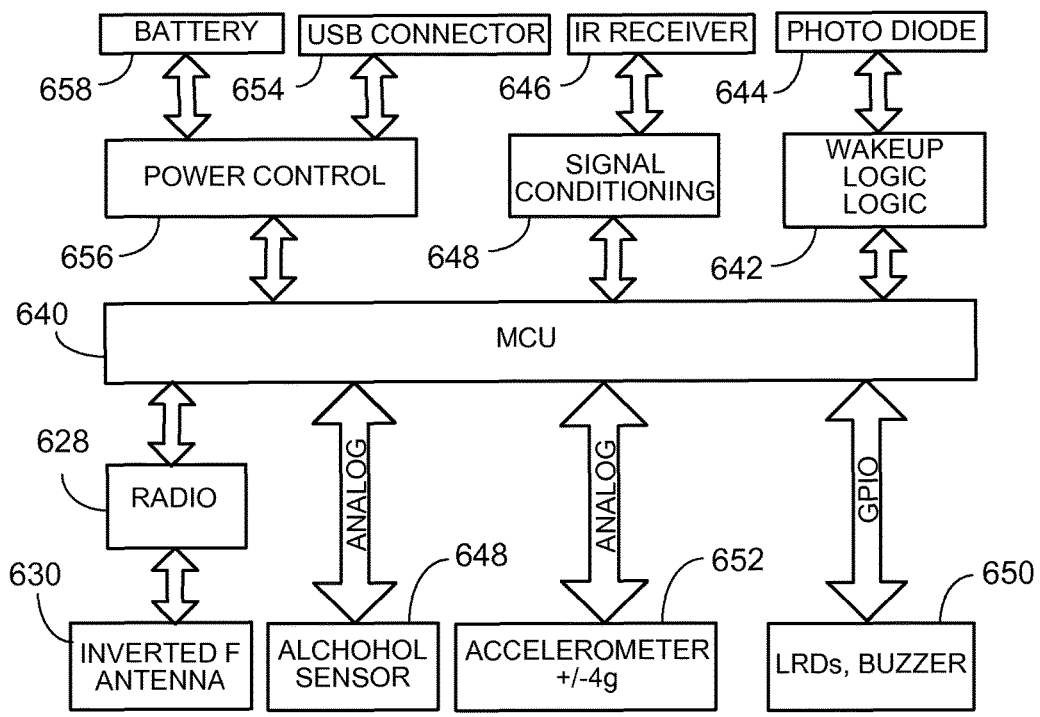
FIG. 24 is a schematic view of a badge.
Figure 25A:
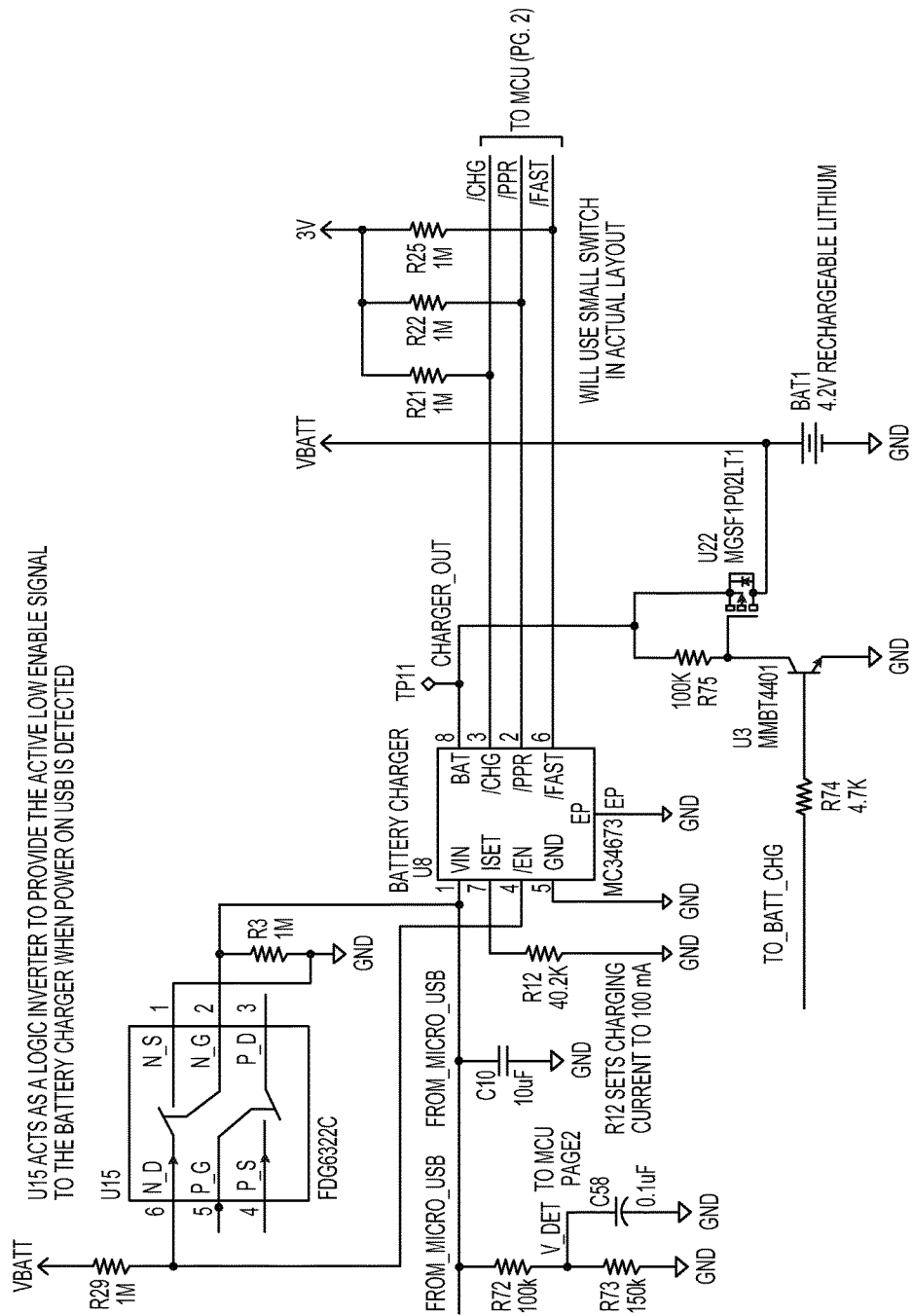
FIGS. 25A-25K are wiring schematics for embodiments of a badge, a monitor, and a base station.
Figure 25B:
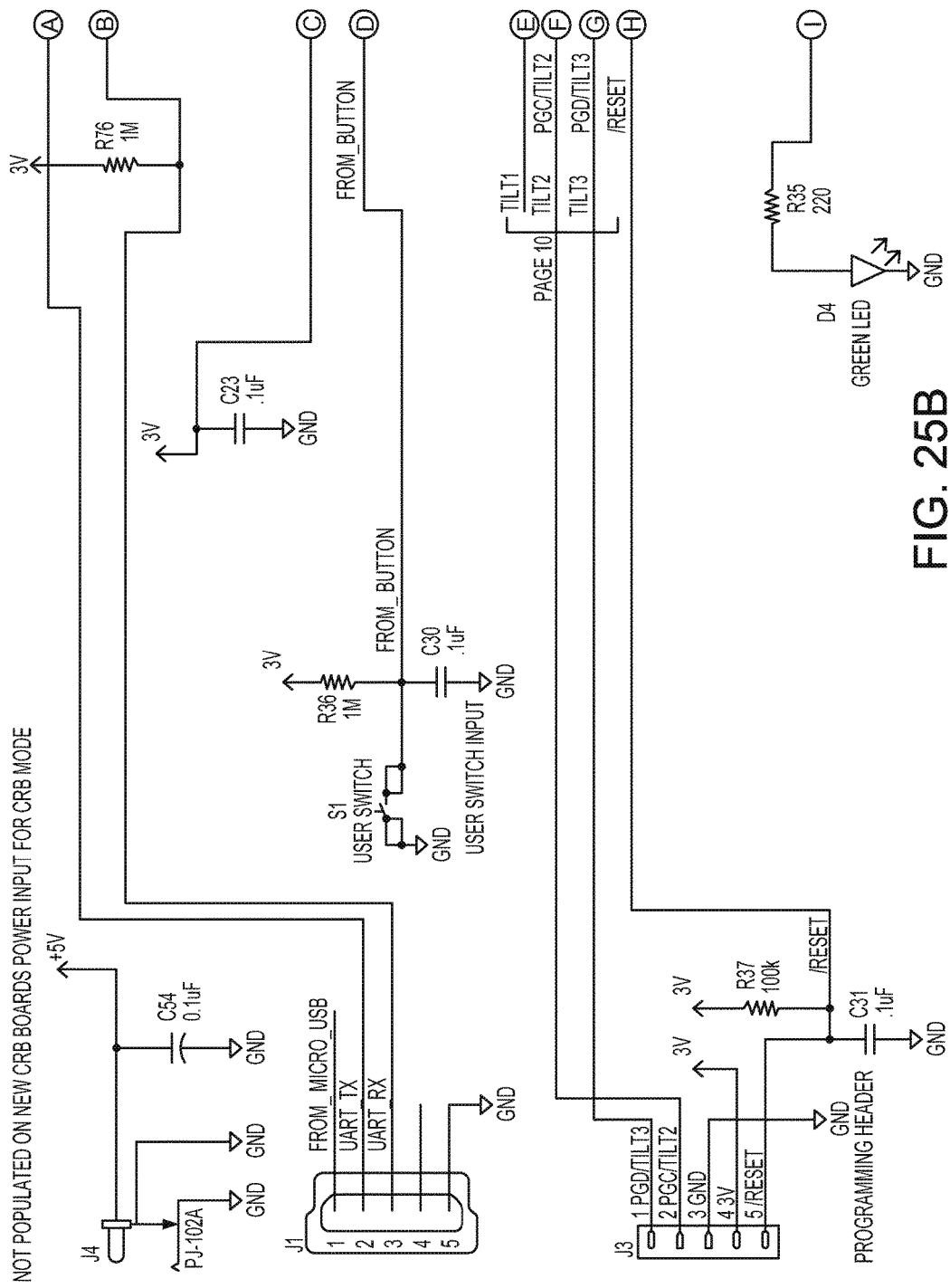
Figure 25B:
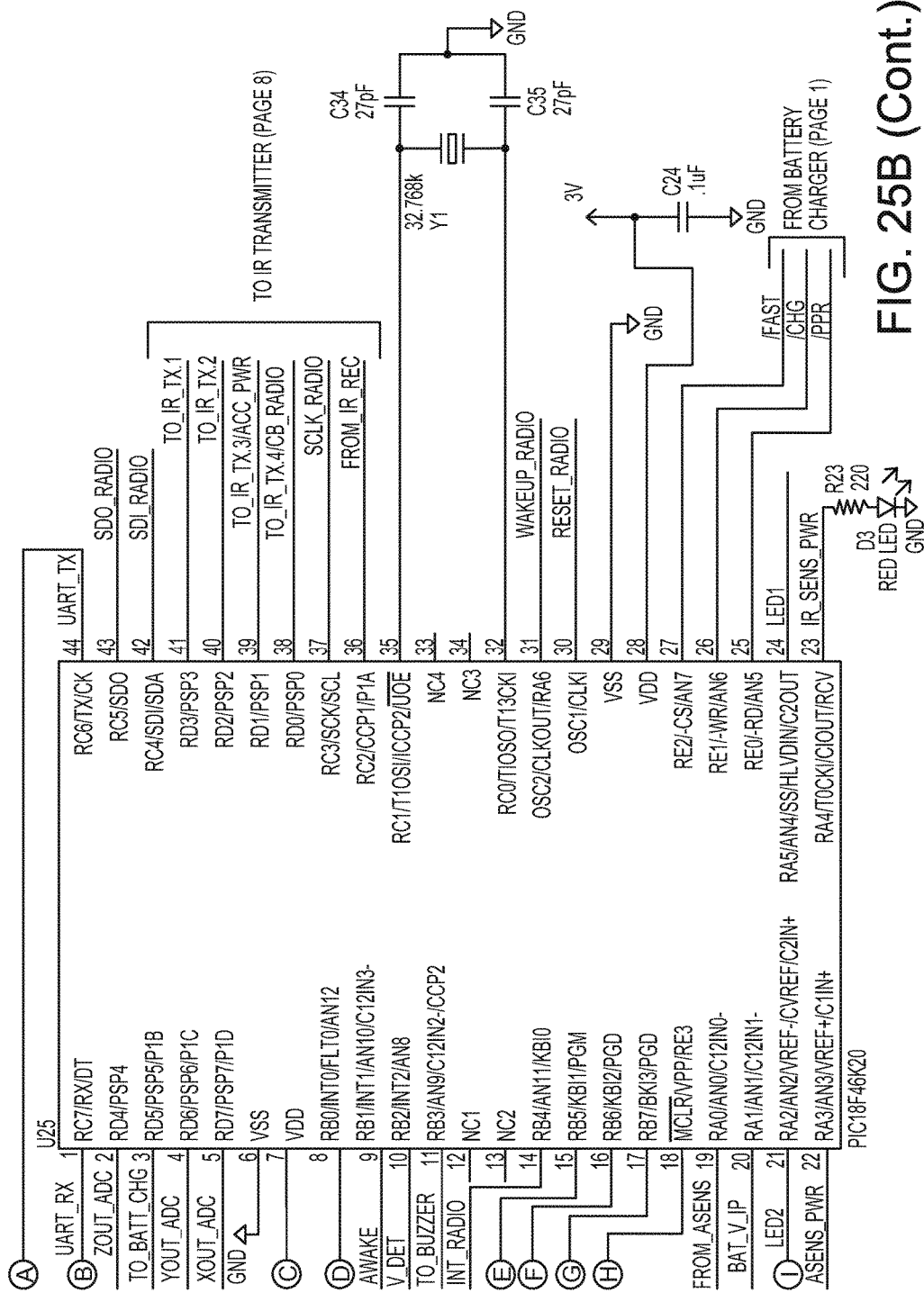
Figure 25C:
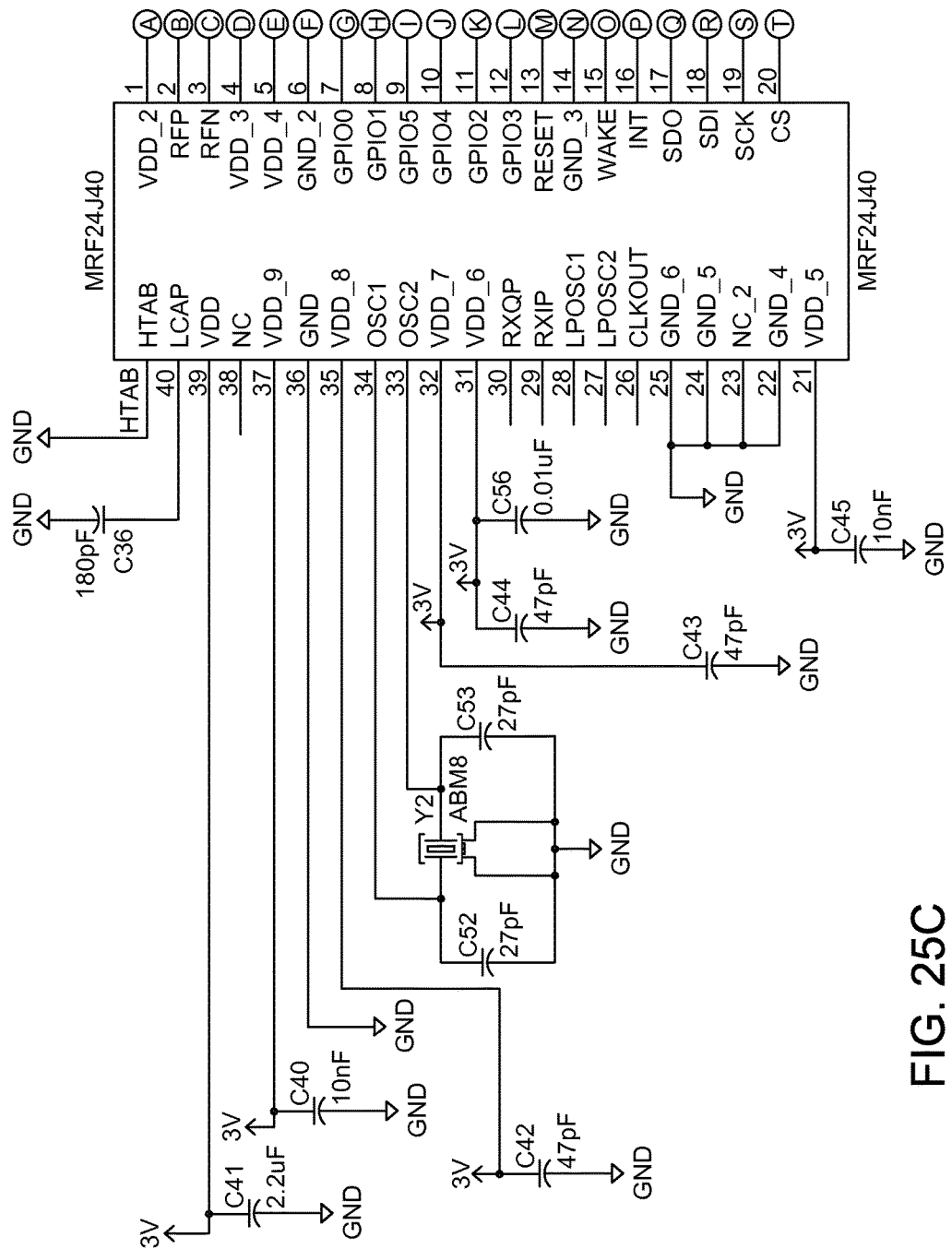
Figure 25C:
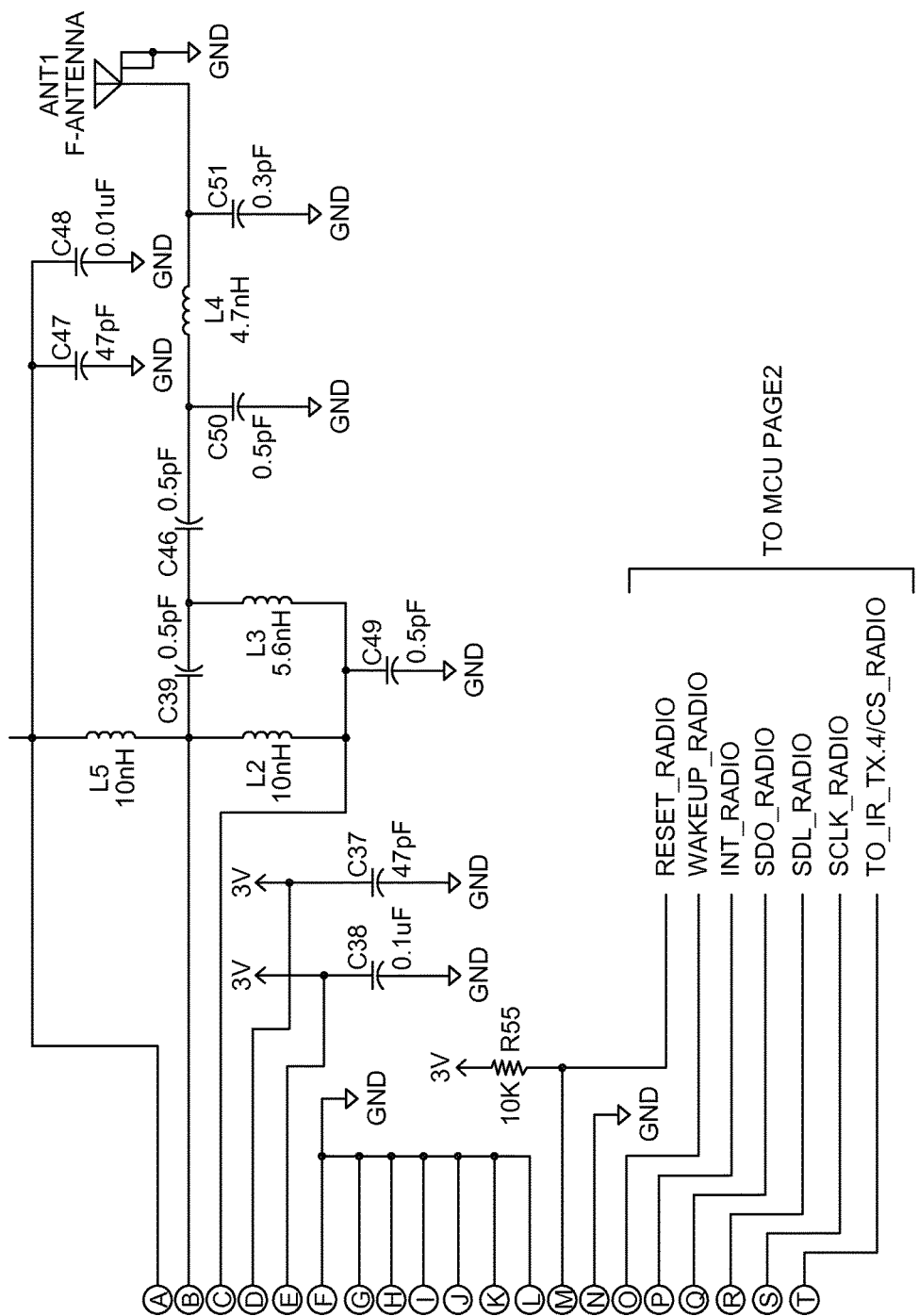
Figure 25D:
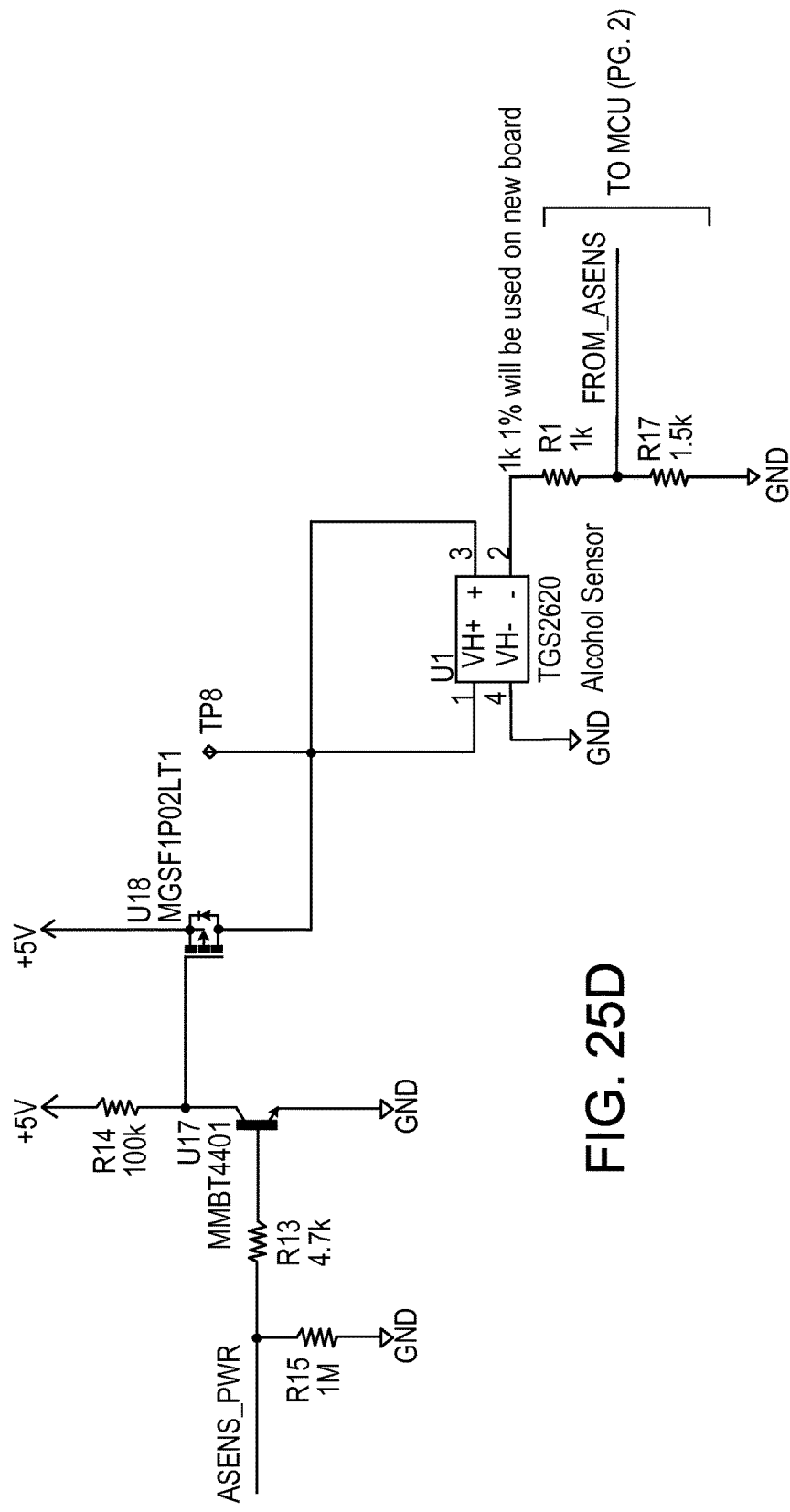
Figure 25E:
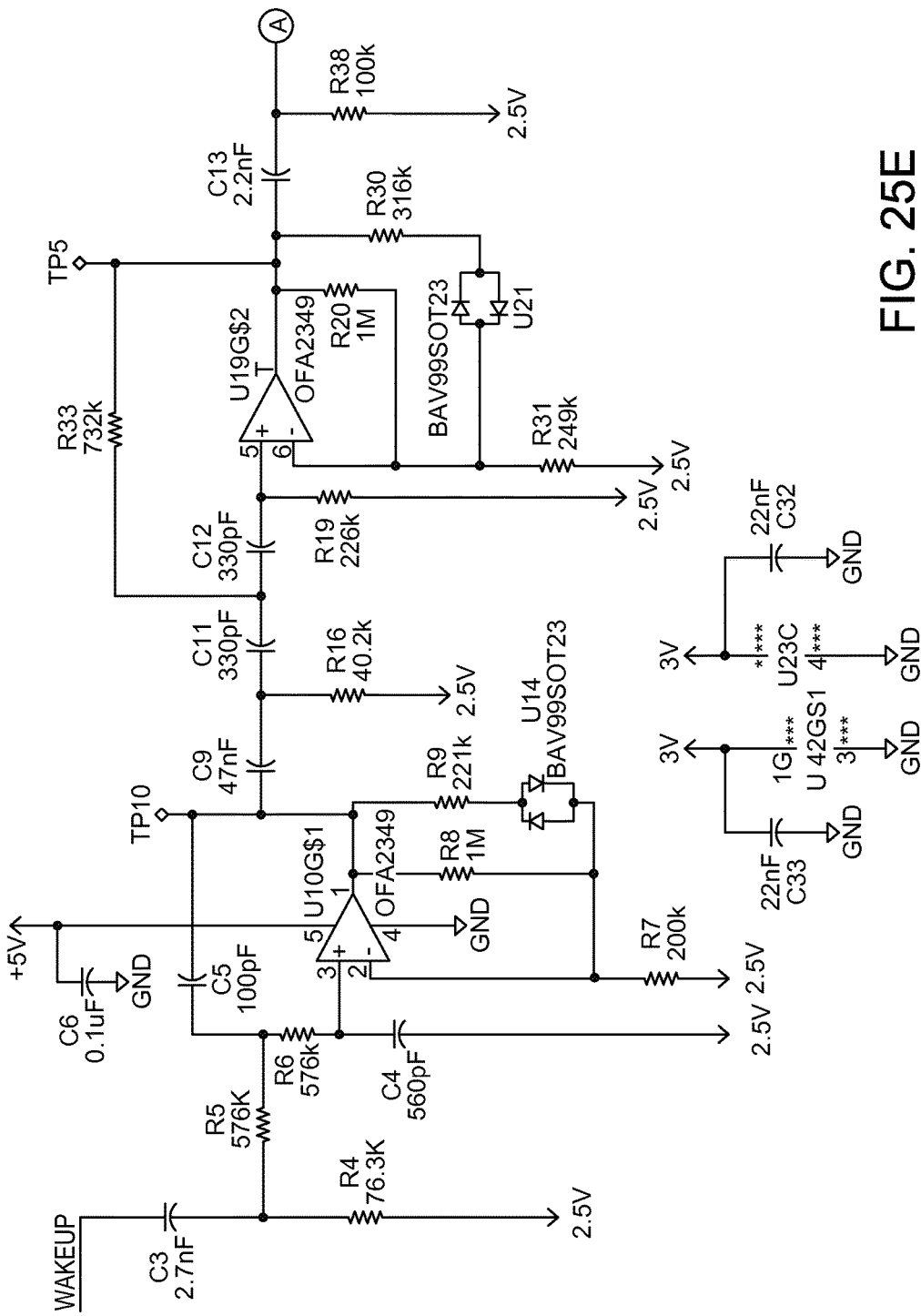
Figure 25E:
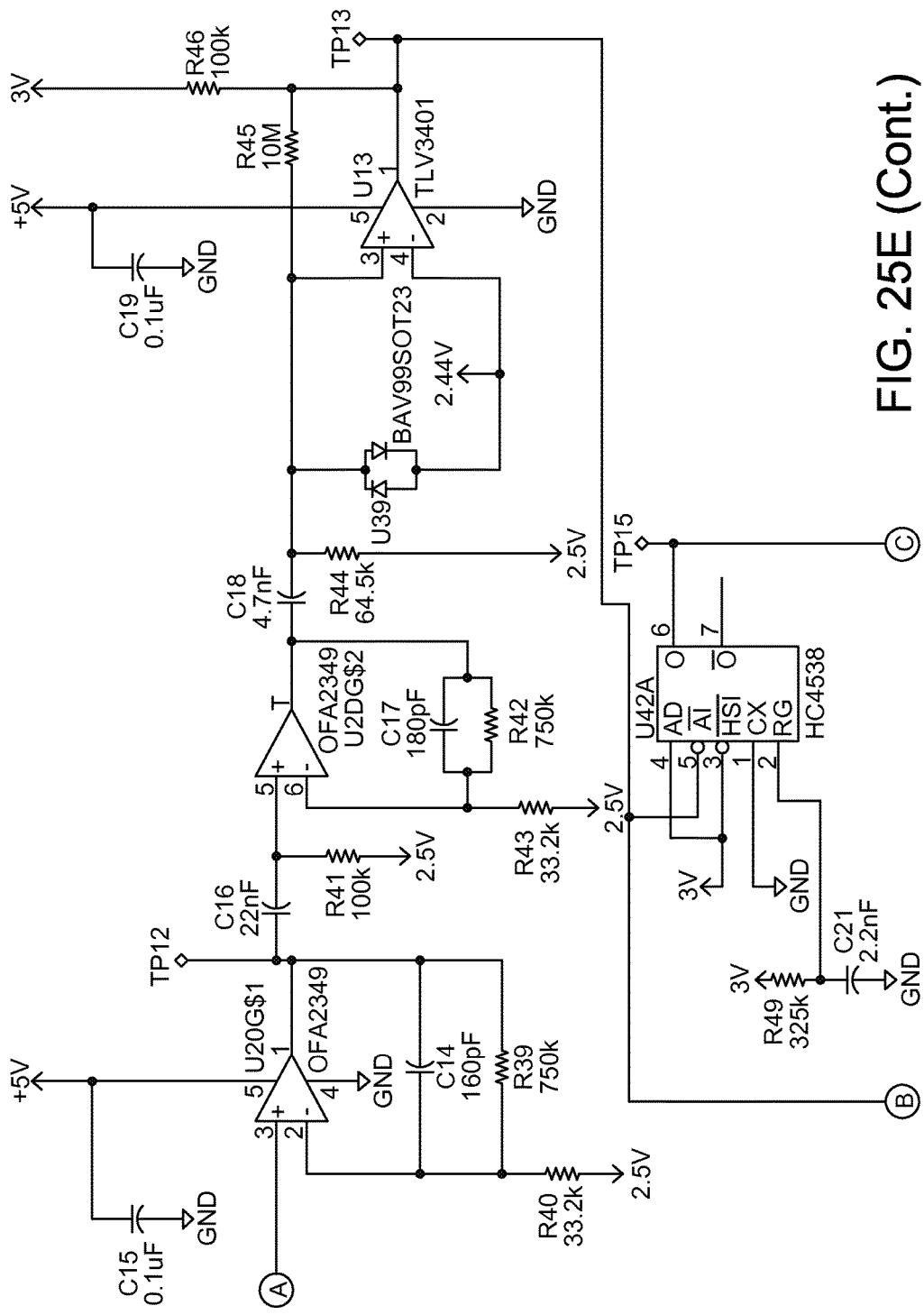
Figure 25E:
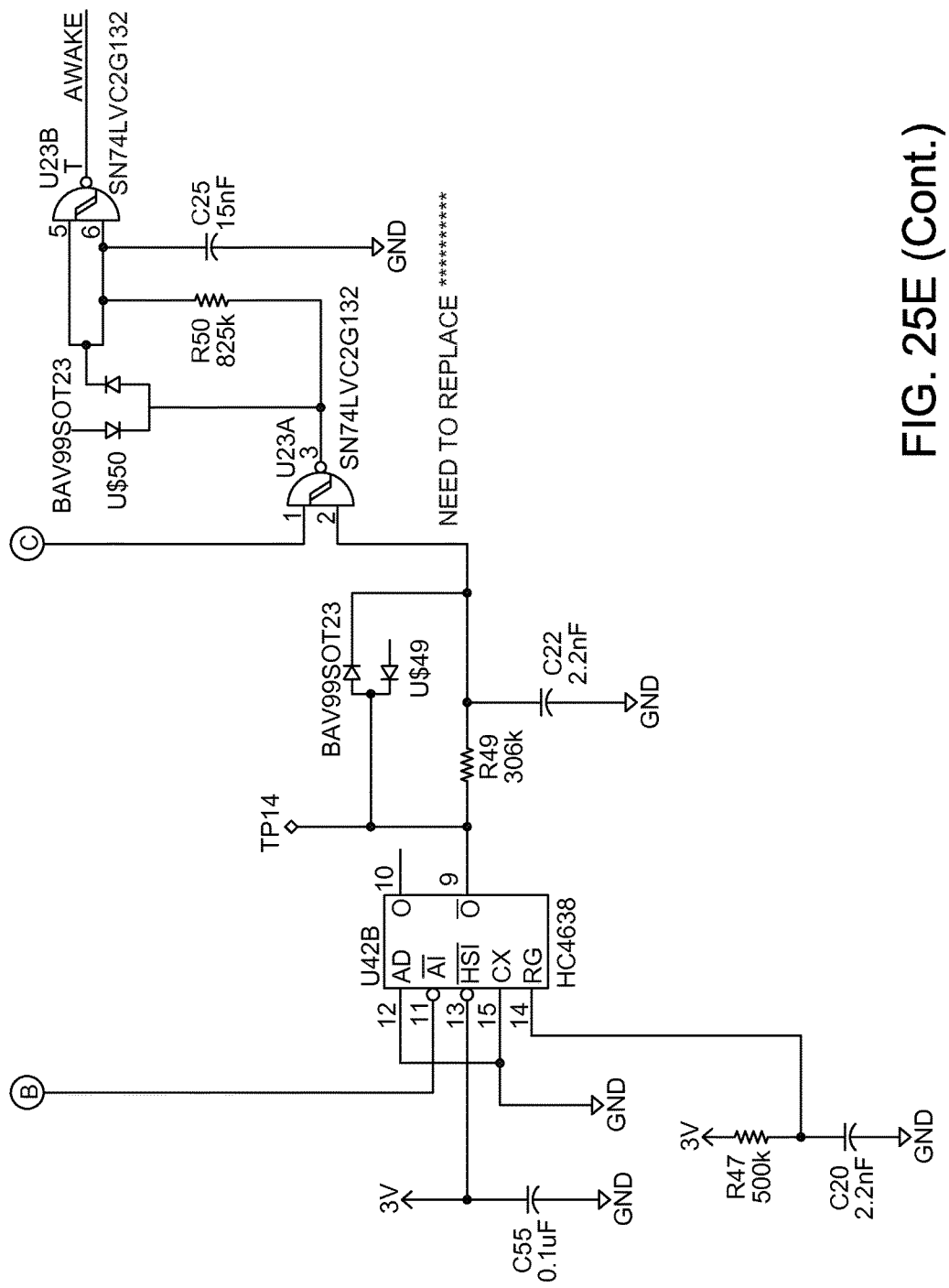
Figure 25F:
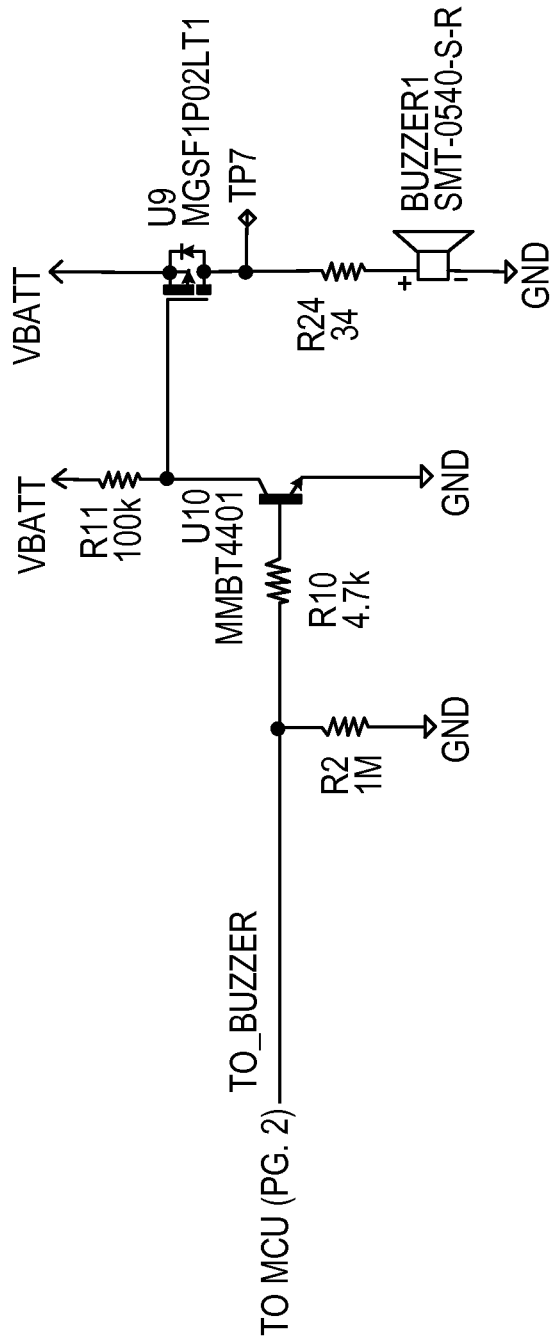
Figure 25G:
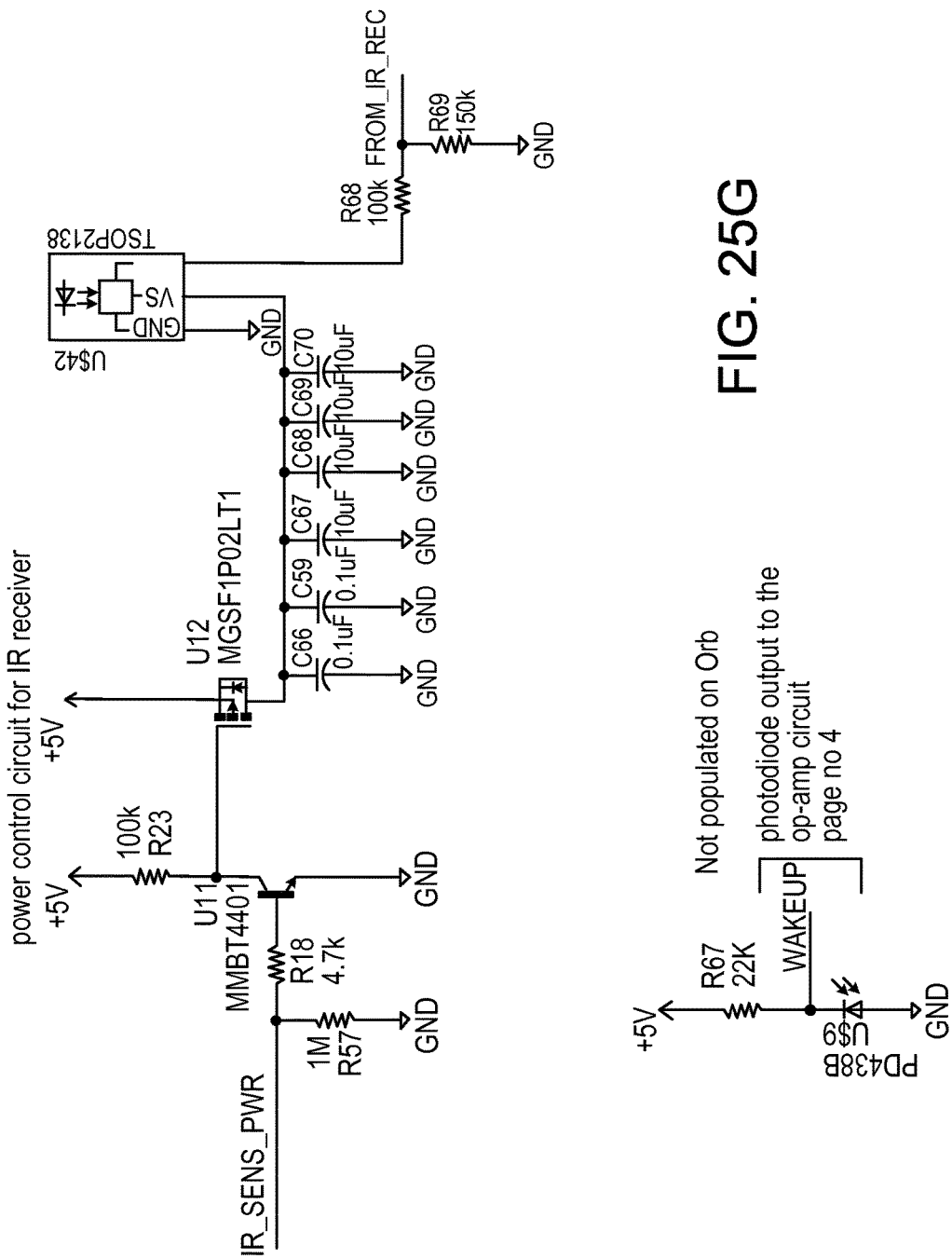
Figure 25H:
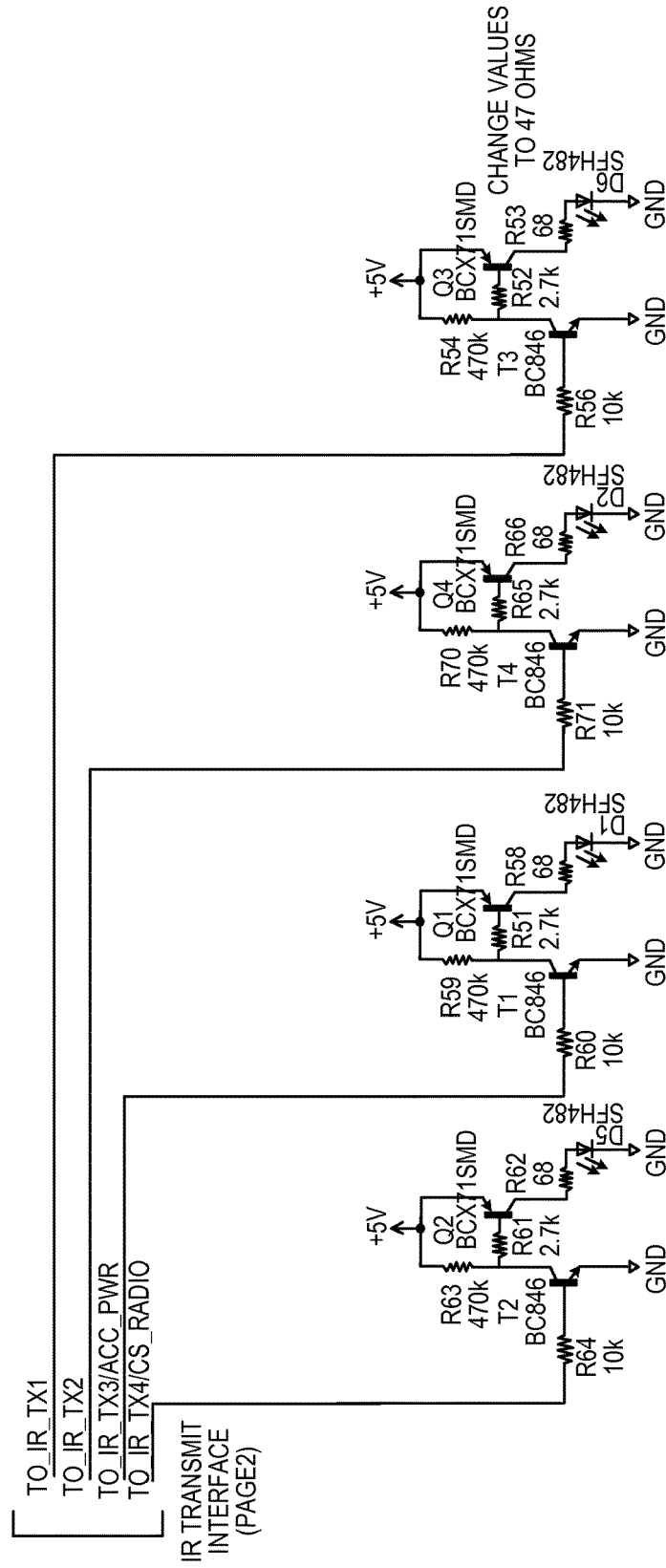
Figure 25I:
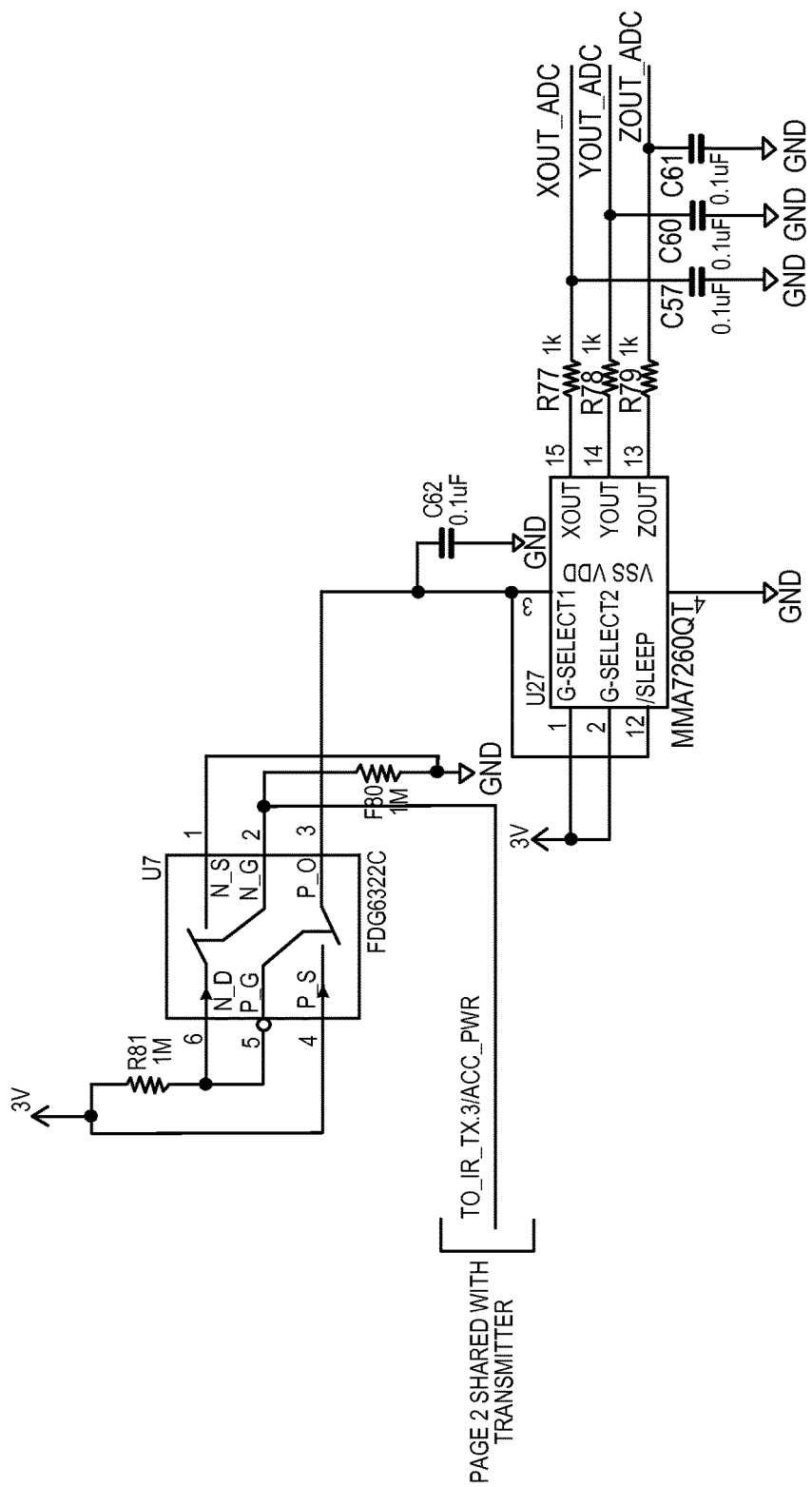
Figure 25J:
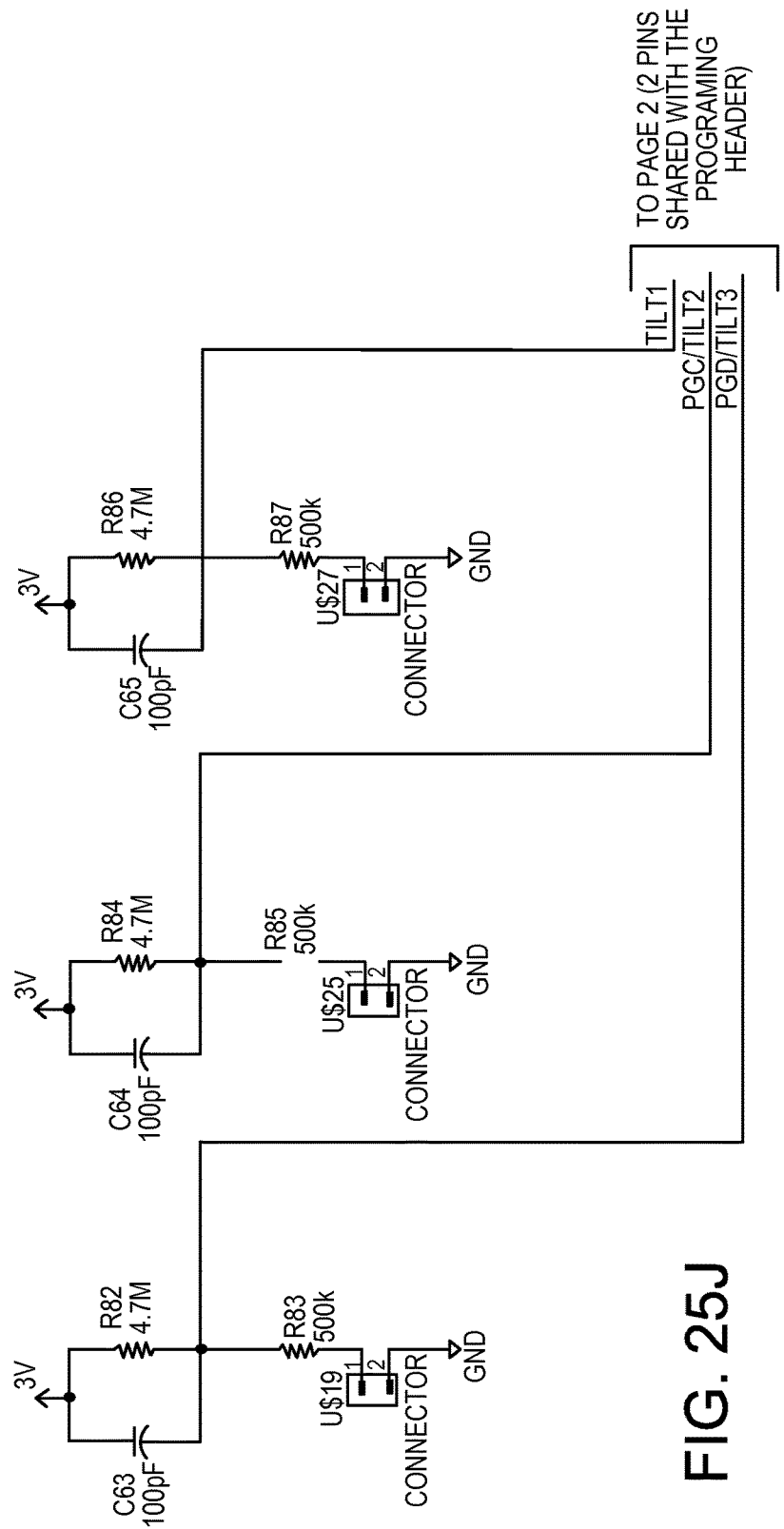
Figure 25K:
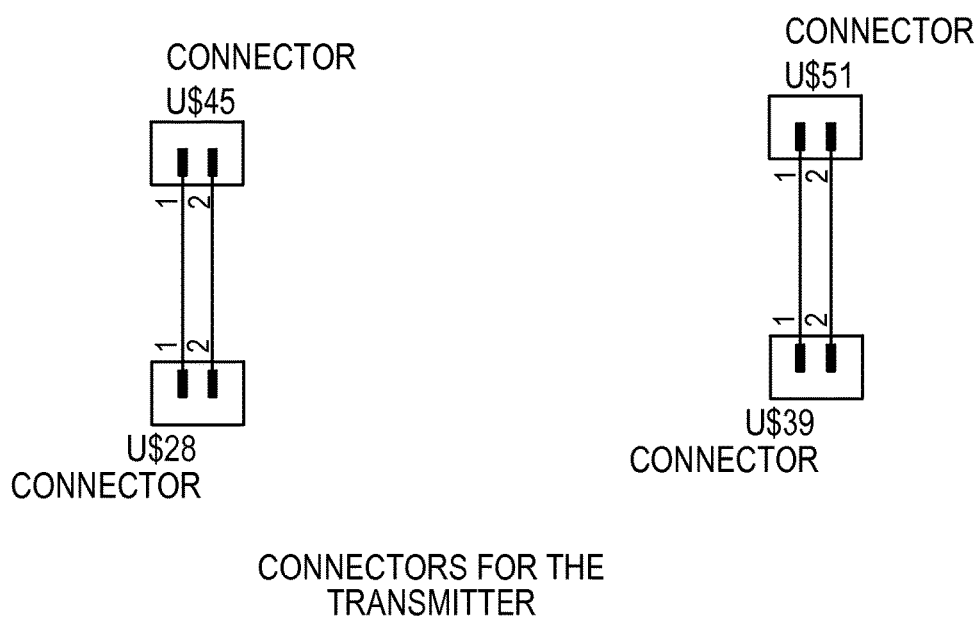
Figure 26:
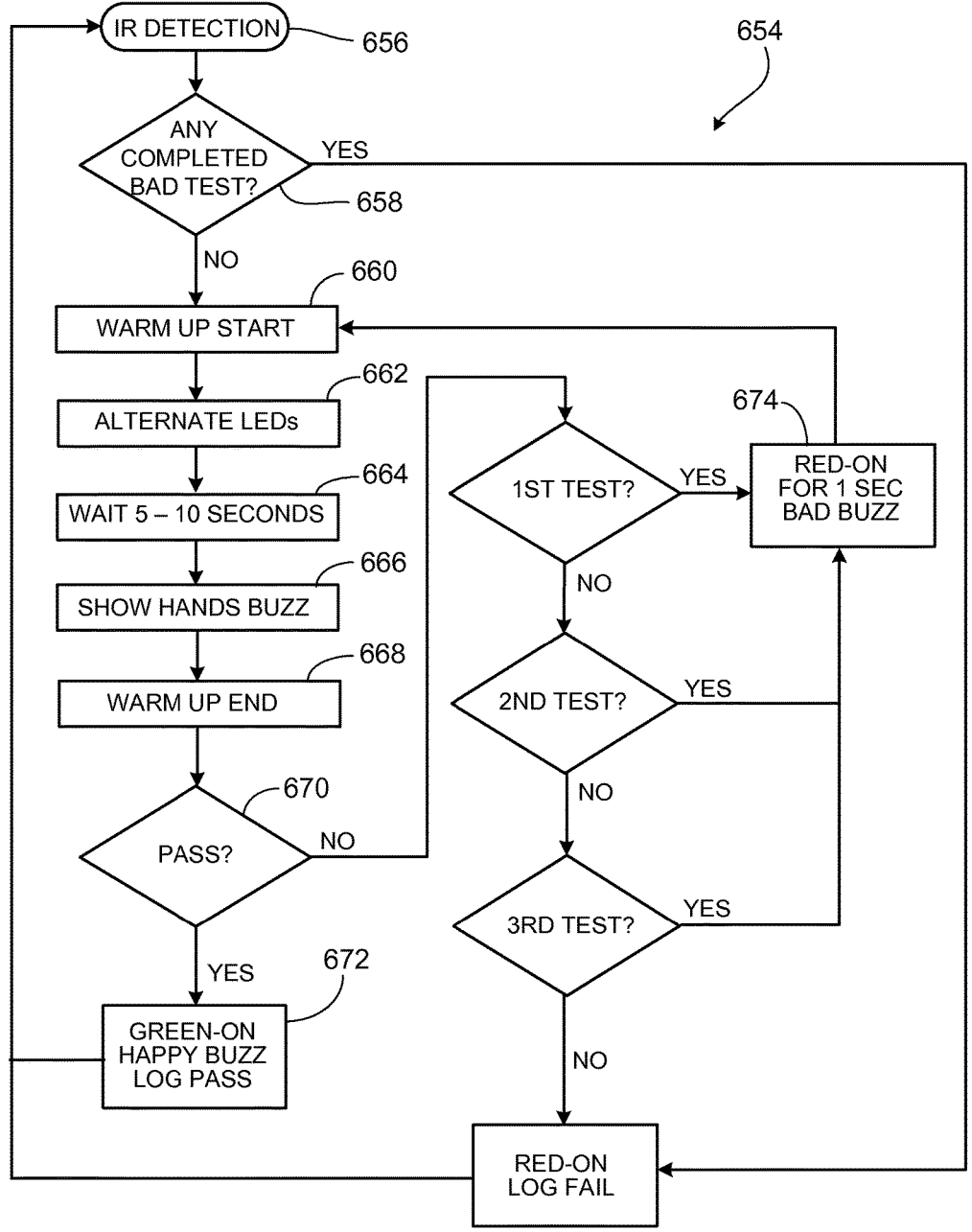
FIG. 26 is a schematic of badge logic.
Figure 27A:
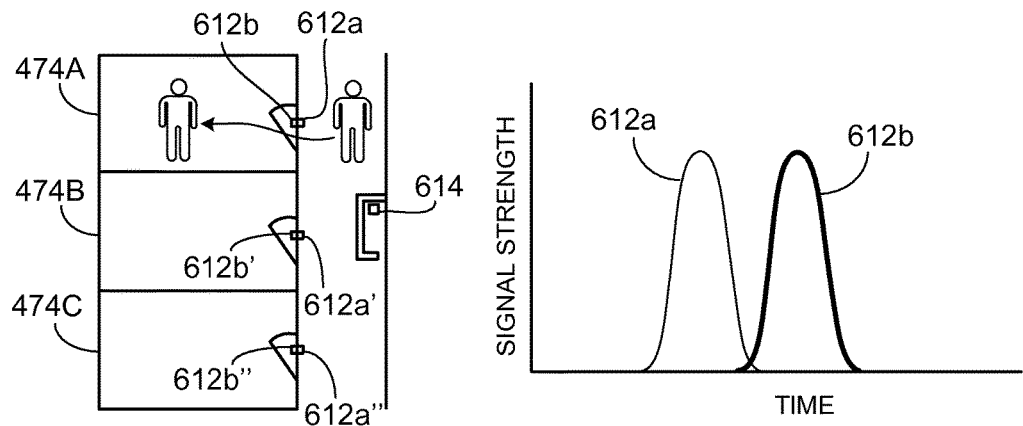
FIGS. 27A-27D illustrate operation of a cleanliness monitoring system.
Figure 27B:
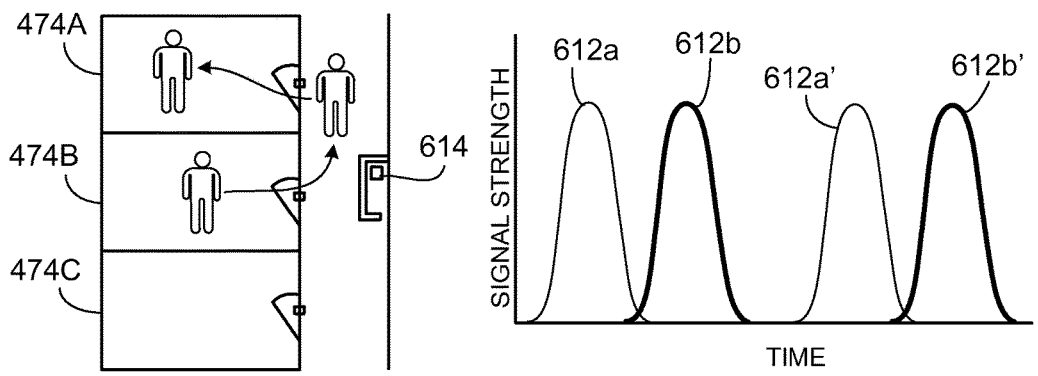
Figure 27C:
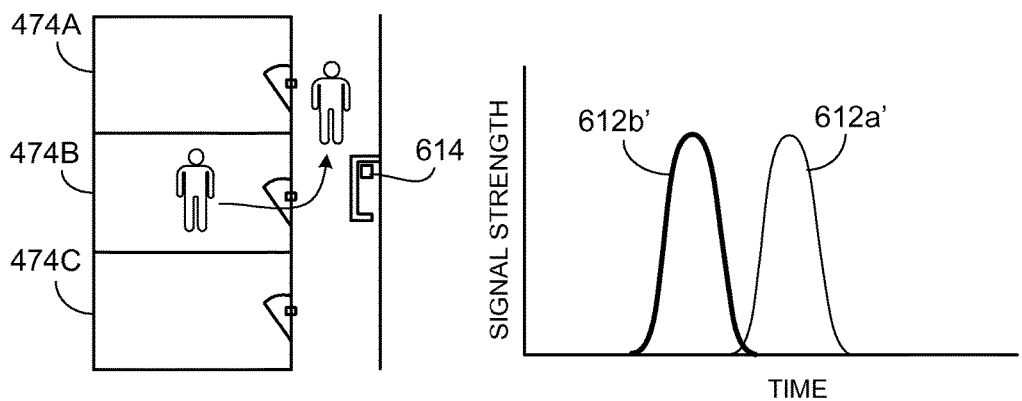
Figure 27D:
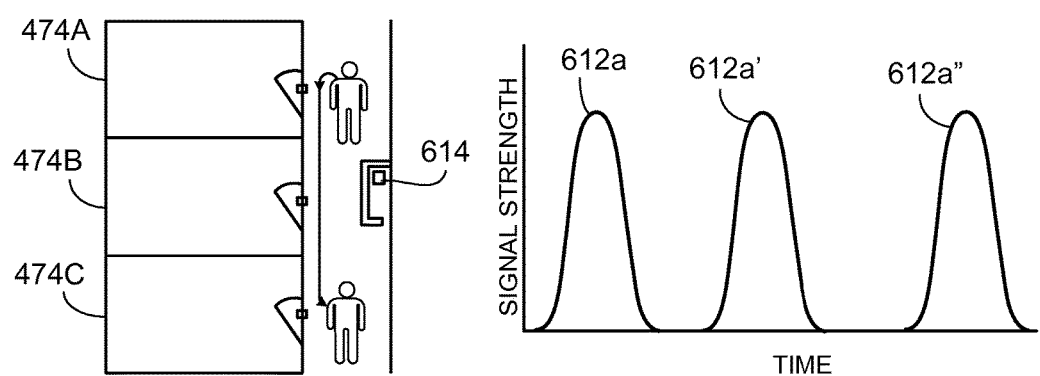

As illustrated in FIGS. 24 and 25, the badges 610 used in the test had multiple functions that were controlled by a microcontroller unit 640 (e.g., a PLC chip and associated software). The badges 610 were generally similar to the badges 410 but did not include a manual triggering button. A wakeup logic application 642 monitored signals from a photodiode 644 activated by infrared light. The badges 610 were configured to continuously monitor their environments using the photodiode, and were activated by the infrared light of the monitors 612. Once activated, the MCU 640 received the infrared-carried signals from the monitor 612 using an infrared receiver 646 and associated signal processing application 648 to determine and store the monitor identification and then initiated a cleanliness test cycle. In the test, the location of the monitor 612 was correlated with its location in a database stored on a central server. In some embodiments, the location database can be stored in onboard memory of the badge 610 rather than or in addition to on the central server.

When the cleanliness test cycle was initiated 7, the badge 610 prompted the user to clean his/her hands, warmed up an onboard alcohol sensor 648, then prompted the user again to place his/her hands near the alcohol sensor 648 using light emitting diodes and/or a speaker 650. At this point, the sensor 648 tested for the presence of alcohol by measuring the increase or decrease in voltage level from a metal oxide alcohol sensor.

The badge 610 communicated the success/failure of the alcohol test to the user via light emitting diodes 650 and sounds, and stored a record of the time, location, and status of the alcohol test in memory capable of holding data about hundreds of testing events. The data was downloaded into the base station reader 614 periodically. The badges used in the test downloaded data using a USB interface port 654 (and associated cable) connected to the MCU 640 through a power control module 656. A battery 658 (e.g., a rechargeable battery) was also connected to the power control module 656.

Although the badges 610 used in the test did not include radio frequency transceivers, some badges include radiofrequency transceivers 628 with antennas 630 to provide an additional communication link in case of any potential need for radiofrequency communication including, for example, when downloading data from the badges. Such radiofrequency transceivers can provide high rate data transmission. In some embodiments, the badges are configured to use an automated wireless download rather than the USB port/cable. In automated wireless download embodiments, when a health care worker passes, for example, a base station 614, his/her badge 610 is triggered to transmit stored test data to the base station 614.

Similarly, although the badges 610 used in the test did not include accelerometers, some badges include accelerometers 652 which can provide the MCU with input for battery saving shutdown scheme.

FIGS. 25A-25K provide a wiring schematic for embodiments of the badges 610, monitors 612, and base stations 614. FIGS. 31A-31J also provide wiring schematics for embodiments of a badge 610 and a base station 614.

The base station 614 can be a PC-based application that includes a USB interface operable to connect to USB ports on the badges 610. The base station reader software organizes the badge data 6101 into a comma delimited text file (.csv file) 6102 which compiles the time 6103, location 6104, badge identifier 6105, and success/failure of each hand cleaning event for multiple badges. The .csv file can then be imported to Excel for sorting/viewing of data. In some embodiments, the badges 610 include an RF transmitter and the base station 614 includes an RF receiver which can be used to transfer data from the badges 610 to the base station 614.

FIGS. 26, 27A-27D, and 30 illustrate the sequence of events that occurs when the un-sanitized mode of a badge 610 is triggered by passage through a doorway or other monitored boundary. Upon powering up, the badge 610 enables its IR detector and the badge microprocessor monitors the badge IR detector, to detect patterns of IR light (sequences of off/on light bursts) which indicate the presence of a monitor. When a monitor is detected, the badge 610 registers the Orb #, System ID #, and the "indoor" or "outdoor" status of the monitor. When the badge detects another monitor and registers the same Orb#/System ID # with the opposite "indoor/outdoor" designation, the badge 610 recognizes a transition event.

A doctor standing in the hall passes through the doorway 475 into room 474A passing under monitor(s) 612*aa* and 612*ab* on the outside 477 of the door frame 479 and then under monitor(s) 612*bb* and 612*bc* on the inside 481 of the door frame 479. The doctor's badge 610 is activated from its listening mode when photodiode 644 (see FIG. 24) receives infrared light from monitor(s) 612*a*. As the doctor passes through the doorway, the infrared receiver 646 of the badge 610 receives an identification signal from monitor(s) 612*a* and then from monitor(s) 612*b*. As monitor 612*a* and monitor 612*b* have the same Orb#/System ID # with the opposite indoor/outdoor designations, the badge 610 recognizes a transition event.

The receipt of sequential infrared signals triggers a hand cleanliness test cycle 654. The badge 610 starts the process of warming up the alcohol sensor 660 and indicates that a test is required (e.g., by alternately flashing the red and green light emitting diodes) 662 and/or by emitting an audible signal (e.g., one or more audible beeps). The microprocessor monitors the voltage output of the tin-oxide sensor to establish a baseline of output for "clean" air, then emits a series of beeps to signal its readiness for an alcohol test to the user. The "test required" signaling continues 664 for about 8 seconds (e.g., between 5-10 seconds) which allows the doctor to wash her hands with, for example, an alcohol based cleaner. The badge 610 then signals 666 (e.g., by a soft buzzing sound and/or a blinking red light emitting diode) that the doctor should apply one of her fingers to or near the alcohol sensor and the warm up cycle ends 668. The MCU then executes a cleanliness check as described above with respect to other embodiments. If there is sufficient alcohol vapor present for a successful test, the badge signals a successful test 672 by, for example, turning off the red light emitting diode, turning on the green light emitting diode, and making a pleasing sound. The badge then resets to listening mode. If there is not sufficient alcohol vapor present for a successful test, the badge signals an unsuccessful test 672 by, for example, flashing the red light emitting diode and making an unpleasant sound. The badge can then return to the start of the warm up cycle 660 for a retest sequence.

Multiple (e.g., up to 3, up to 4, or up to 5) retest sequences are repeated until the badge discontinues testing and the red light emitting diode on the badge is turned on, a failed test is recorded, and the badge returns to listening mode. If, during the initial check 658, the MCU found that a complete failed or bad test had occurred since the badge was activated by passage through the doorway, the red light emitting diode on the badge is turned on, a failed test is recorded, and the badge returns to listening mode without activating the alert signals discussed above (e.g., flashing lights, sounds, vibration). This bypass allows the badge to be silenced without operator intervention or a successful hand washing check under circumstances when other activities are more important than hand washing. For example, if the doctor had entered room 474A during rounds to make a routine check on a patient, her badge would prompt her to wash hands using the signals described above. After she washed her hands and completed a successful cleanliness check, her badge 610 would be set to its sanitized state and would display, for example, a steady green light. However, if the doctor had entered room 474A because the patient had suffered a heart attack, multiple health care workers would likely be entering room 474A in close succession and all of their badges would be triggered to signal the need for hand washing. However, under these circumstances, the need for urgent medical intervention might preempt hand washing. After three tests which would be unsuccessful because the health care workers would not be applying their fingers to or near their badges 610, the badges would stop the possibly distracting signaling.

In either case, when the doctor left room 474A and entered room 474B, her badge would be triggered when she entered the hallway and retriggered when she entered room 474B. After she washed her hands and completed a successful cleanliness check, her badge 610 would be set to its sanitized state and would display, for example, a steady green light. If the doctor entered room 474B without washing her hands and completing a successful cleanliness check in the hall, her badge would record passing through the hallway as a failed cleanliness check.

After the doctor left room 474B and went to a central desk station, her badge would be triggered as she passed through the doorway. Her badge would prompt her to wash hands using the signals described above and, after she washed her hands and completed a successful cleanliness check, her badge 610 would be set to its sanitized state and would display, for example, a steady green light.

Base station 614 could be located at the central desk station. Health care workers such as the doctor could periodically (e.g., at the end of each shift) download data from their badges 610 to the base station (see FIG. 30).

In some embodiments, the badges 610 include an onboard emitter (e.g., RF transmitter) and the base station 614 includes an RF receiver which can be used to transfer data from the badges 610 to the base station 614. For example, the base station 614 can transmit a signal (e.g., an RF beacon signal (802.15.4) every 750 milliseconds or continuously transmit an IR signal) identifying the base station and system ID# (step 710).

The onboard emitters on the badges 610 can be switched from a default inactive state to an active state to transmit information upon receipt of the signal identifying the base station and system ID# (or other external receiving equipment). Badges 610 whose onboard emitters are activated by the base station 614 can respond, for example, by transmitting an acknowledgement signal using 802.15.4 wireless signal protocols. When the base station 614 receives an acknowledgement signal from a badge 610 (step 712), the base station 614 can respond to the badge 610 that the base station 614 is ready to receive data. The badge 610 can authenticate that the base station 614 has the appropriate System ID, then transmit its records.

The base station 614 receives a message indicating the number of records to be transmitted by the badge 610 (step 714), receives data records from the badge 610, and translates the records received from the badge 610 into a format which can be stored (step 718), for example, on a local PC in a text-delimited data file. The base station compares the number of records received to the expected number of records (step 720). If the number of records match, the base station 614 can transmit an acknowledgement to the badge 610 to indicate accurate receipt of data and can return to its beacon mode (step 722). In some embodiments, separate software on the PC is used to pass the data file through network connections to a storage database, either online or within the hospital server network.

The badge 610 can disable its onboard emitter (e.g., RF transmitter), erase its memory, and return to the passive monitoring state after receiving confirmation from the base station 614 that the downloaded number of records have been received.

This approach can limit emissions (e.g., radio frequency emissions) from the badges 610 except when devices are triggered to download information to the external receiving equipment. For example, it can be desirable to limit emissions in the patient care portion of a hospital room.

After downloading her badge 610 (e.g., by USB connection to the base station 614 or RF transmission of data while passing the base station 614), the doctor walks down the hall. Her badge receives signals 612a, 612a', 612a" from monitors on the outside of the doorways of rooms 474A, 474B, 474C. Because the received signals 612a, 612a', 612a" are all "outside" signals, the badge 610 determines that it has not crossed a monitored boundary and does not activate a cleanliness check cycle.

Similar approaches can be used to promote good sanitary practices in other spaces (e.g., open bay wards and nurseries) in which it is desirable that individuals sanitize their hands both on entering and/or exiting the specific space. More generally, similar systems can be used to prompt good hygiene in a healthcare environment, and may also be used in restaurants, cruise ships, and other environments where good hygiene is important.

A wide variety of other implementations are within the scope of the following claims.

For example, the hand washing routines described above can be implemented based on badges identifying hand cleanliness by the presence of alcohol vapors on a user's hands. However, similar logic could be used to trigger hand wash signals for badges which are reset to a sanitized state by other means including, for example, registering the operation of equipment such as a faucet and soap dispenser or by monitoring the time spent in front of a soap-and-water sink with a successful hand-cleaning event determined after a prescribed period of time is spent at the sink.

In another example, some badge embodiments include other battery life extension features. For example, an IR detector on the badge can be disabled during a charging cycle. Onboard emitters (e.g., an RF transceiver) can be disabled until a sensor on the badge detects a "Base Station Orb". The cleanliness sensor (e.g., alcohol sensor) can be disabled until the badge detects a "Room Transition", then the tin-oxide sensor is warmed up with electrical current. The light emitting diodes can be used in "blinking" mode instead of constantly on. When triggered, cleanliness tests are repeated a limited number of times (e.g., four times) in response to failures before being discontinued to save power.

The invention claimed is:

1. A method comprising:
receiving, on a wearable device, a first signal including an identifier associated with a doorway and an outdoor status;
receiving, on the wearable device, a second signal including an identifier associated with the doorway and an indoor status;
evaluating whether the first wearable device is crossing through the doorway;
controlling a cleanliness state of the wearable device based on results of the evaluation;
wherein the wearable device determines the person is entering a space on receiving, on the device worn by the person, the first signal associated with the doorway of the space and an outdoor status and then receiving, on the device worn by the person, the second signal associated with the doorway of the space and an indoor status; and controls the cleanliness state of the wearable device to an un-sanitized state if the person is entering the space.

2. The method of claim 1, wherein evaluating whether the wearable device is entering or leaving a location associated with the doorway comprises comparing the first signal with the second signal.

3. The method of claim 2, comprising evaluating whether the wearable device is entering a location associated with the doorway if the first signal is received before the second signal.

4. The method of claim 3, wherein controlling the cleanliness state comprises controlling the wearable device to an un-sanitized state if the second signal is received after the second signal.

5. The method of claim 2, comprising evaluating whether the wearable device is leaving a location associated with the doorway if the second signal is received before the first signal.

6. The method of claim 2, wherein the first signal is transmitted by a first monitor and the second signal is transmitted by a second monitor different from the first monitor.

7. The method of claim 1, wherein receiving the first signal comprises receiving an infrared signal.

8. A method in which a device worn by a person can determine from received wireless communications whether the person is entering a space or exiting the space and controlling a cleanliness state of the wearable device based on whether the person is entering the space or exiting the space,
wherein the device
determines the person is exiting the space on receiving, on the device worn by the person, a first signal representative of a doorway of the space and an indoor status and then receiving, on the device worn by the person, a second signal representative of the doorway of the space and an outdoor status;

determines the person is entering the space on receiving, on the device worn by the person, a first signal representative of a doorway of the space and an outdoor status and then receiving, on the device worn by the person, a second signal representative of the doorway of the space and an indoor status; and controls the cleanliness state of the wearable device to an unsanitized state if the person is entering the space; and controls the cleanliness state of the wearable device based on the determination.

9. The method of claim 8, wherein receiving the signal comprises receiving an infrared signal.

10. The method of claim 8, wherein receiving the signal comprises receiving an infrared signal.

* * * * *